(12) United States Patent
Albaek et al.

(10) Patent No.: US 11,248,019 B2
(45) Date of Patent: Feb. 15, 2022

(54) TRITYL-MONO-GALNAC COMPOUNDS AND THEIR USE

(71) Applicant: Hoffmann-La Roche Inc., Little Falls, NJ (US)

(72) Inventors: Nanna Albaek, Hørsholm (DK); Jacob Ravn, Hørsholm (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 276 days.

(21) Appl. No.: 16/093,347

(22) PCT Filed: Apr. 18, 2017

(86) PCT No.: PCT/EP2017/059080
§ 371 (c)(1),
(2) Date: Oct. 12, 2018

(87) PCT Pub. No.: WO2017/178656
PCT Pub. Date: Oct. 19, 2017

(65) Prior Publication Data
US 2019/0144488 A1    May 16, 2019

(30) Foreign Application Priority Data

Apr. 14, 2016 (EP) .................................... 16165303

(51) Int. Cl.
| | | |
|---|---|---|
| C07H 21/00 | (2006.01) | |
| A61K 47/54 | (2017.01) | |
| C07H 15/18 | (2006.01) | |

(52) U.S. Cl.
CPC ........... *C07H 21/00* (2013.01); *A61K 47/548* (2017.08); *A61K 47/549* (2017.08); *C07H 15/18* (2013.01); *Y02P 20/55* (2015.11)

(58) Field of Classification Search
None
See application file for complete search history.

(56) References Cited

FOREIGN PATENT DOCUMENTS

| WO | WO 98/39352 | 9/1998 |
|---|---|---|
| WO | WO 99/14226 | 3/1999 |
| WO | WO 00/47599 | 8/2000 |
| WO | WO 00/66604 | 11/2000 |
| WO | WO 01/23613 | 4/2001 |
| WO | WO 2002/094185 | 11/2002 |
| WO | WO 2004/046160 | 6/2004 |
| WO | WO 2014/179620 | 11/2006 |
| WO | WO 2007/031091 | 3/2007 |
| WO | WO 2007/090071 | 9/2007 |
| WO | WO 2007/134181 | 11/2007 |
| WO | WO 2007/146511 | 12/2007 |
| WO | WO 2008/113832 | 9/2008 |
| WO | WO 2008/131419 | 10/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/073809 | 6/2009 |
| WO | WO 2009/090182 | 7/2009 |
| WO | WO 2009/124238 | 10/2009 |
| WO | 2010/039548 A2 | 4/2010 |
| WO | WO 2010/036698 | 4/2010 |
| WO | WO 2010/077578 | 7/2010 |
| WO | WO 2011/017521 | 2/2011 |
| WO | WO 2011/104169 | 9/2011 |
| WO | WO 2012/083046 | 6/2012 |
| WO | WO 2013/036868 | 3/2013 |
| WO | WO 2013/154798 | 10/2013 |
| WO | WO 2014/076195 | 5/2014 |
| WO | WO 2014/118267 | 8/2014 |
| WO | WO 2015/006740 | 1/2015 |
| WO | WO 2015/071388 | 5/2015 |
| WO | WO 2011/156202 | 12/2015 |

(Continued)

OTHER PUBLICATIONS

Matulic-Adamic et al., Bioconjugate Chemistry, 2002, 13(5), pp. 1071-1078. (Year: 2002).*

(Continued)

*Primary Examiner* — Traviss C McIntosh, III
(74) *Attorney, Agent, or Firm* — Smith Gambrell & Russell LLP

(57) ABSTRACT

This invention generally relates to the field of phosphoramidite derivatives. In particular, the invention relates to N-Acetylgalactosamine (GalNAc) compounds, in particular phosphoramidite or phosphonoamidite molecules of formula (I) with only one GalNAc moiety (formula II) and to conjugates of nucleic acid molecules with such N-Acetylgalactosamine containing molecules. Also provided are methods for preparation of these molecules and possible uses thereof, in particular in medicine. Wherein $R^1$ is H or $C_{1-6}$alkyl; $R^2$ is a triphenylmethyl-based hydroxyl protecting group $R^3$ is a phosphorus-containing group, particularly a phosphoramidite or a phosphonoamidite group, and K is represented by the general formula (II).

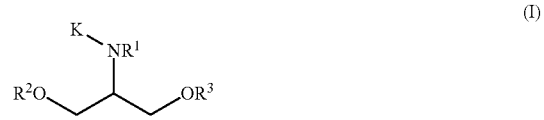

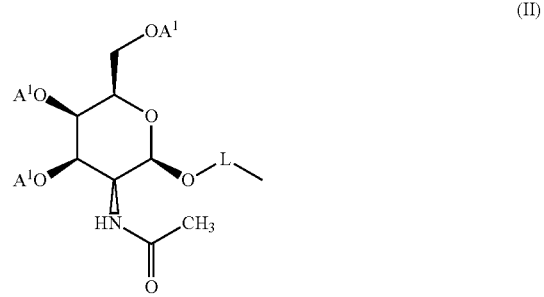

11 Claims, 3 Drawing Sheets
Specification includes a Sequence Listing.

(56) References Cited

FOREIGN PATENT DOCUMENTS

| WO | WO 2016/055601 | 4/2016 |
| WO | WO 2015/105083 | 3/2017 |
| WO | WO 2017/178656 | 10/2017 |
| WO | WO 2005/023995 | 3/2018 |

OTHER PUBLICATIONS

Bergstrom et al., "Unnatural nucleosides with unusual base pairing properties," Current Protocols in Nucleic Acid Chemistry, Jun. 1, 2009, 37(1):1.4.1-1.4.32.

Biosyn.com/' [online], "Oligo Modified Linker Attachment Chemistry," Jun. 12, 2017(retrieved Jun. 12, 2017), XP055380660, retrieved from the Internet: https://www.biosyn.com/oligo-modified-linker-attachment-chemsitry. aspx.

Deleavey and Damha, "Designing chemically modified oligonucleotides for targeted gene silencing," Chemistry & Biology, Aug. 24, 2012, 19(8):937-954.

Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular BioSystems, Molecular BioSystems, Aug. 2009, 5(8):838-843.

Freier et al., "The ups and downs of nucleic acid duplex stability: structure-stability studies on chemically-modified DNA:RNA duplexes," Nucleic Acid Research, Nov. 15, 1997, 25(22):4429-4443.

Hansen et al., "Entropy titration. A calorimetric method for the determination of $\Delta G°(K)$, $\Delta H°$ and $\Delta S°$," Chemical Communications, 1965, 3:36-38.

Holdgate et al., "Measurements of binding thermodynamics in drug discovery," Drug Discovery Today, Nov. 15, 2005, 10(22):1543-1550.

Hirao et al., "Natural versus artificial creation of base pairs in DNA: origin of nucleobases from the perspectives of unnatural base pair studies," Accounts of Chemical Research, Dec. 18, 2012, 45(12):2055-2065.

Langer, "New methods of drug delivery," Science, Sep. 28, 1990, 249(4976):1527-33.

Mangos et al., "Efficient RNase H-directed cleavage of RNA promoted by antisense DNA or 2'F-ANA constructs containing acyclic nucleotide inserts," Journal of American Chemical Society, Jan. 22, 2003, 125(3):654-661.

Matulic-Adamic et al., "Synthesis of N-acetyl-D-galactosamine and folic acid conjugated ribozymes," Bioconjugate Chemistry., Sep. 2002, 13(5):1071-1078.

McTigue et al., "Sequence-dependent thermodynamic parameters for locked nucleic acid (LNA)-DNA duplex formation," Biochemistry, May 11, 2004, 43(18):5388-5405.

Mergny and Lacroix, "Analysis of thermal melting curves," Oligonucleotides, 2003, 13(6):515-537.

Mitsuoka et al., "A bridged nucleic acid, 2',4'-BNA COC: synthesis of fully modified oligonucleotides bearing thymine, 5-methylcytosine, adenine and guanine 2',4'-BNA COC monomers and RNA-selective nucleic-acid recognition," Nucleic Acids Research, Mar. 2009, 37(4):1225-1238.

Morita et al., "2'-O,4'-C-ethylene-bridged nucleic acids (ENA): highly nuclease-resistant and thermodynamically stable oligonucleotides for antisense drug," Bioorganic & Medicinal Chemistry Letters, Jan. 7, 2002, 12(1):73-76.

Putnam and Bashkin, "Synthesis and evaluation of RNA transesterification efficiency using stereospecific serinol-terpyridine conjugates," Nucleosides Nucleotides Nucleic Acids, 2005, 24(9):1309-1323.

Rajeev et al., "Hepatocyte-specific delivery of siRNAs conjugated to novel non-nucleosidic trivalent N-acetylgalactosamine elicits robust gene silencing in vivo," ChemBioChem, Apr. 13, 2015, 16(6):903-908.

Remington's Pharmaceutical Sciences, Mack Publishing Company, Philadelphia, Pa., 17th ed., 1985, 21 pages.

Rensen et al., "Determination of the upper size limit for uptake and processing of ligands by the asialoglycoprotein receptor on hepatocytes in vitro and in vivo," Journal of Biological Chemistry, Oct. 5, 2001, 276(40):37577-37584.

Rukov et al., "Dissecting the target specificity of RNase H recruiting oligonucleotides using massively parallel reporter analysis of short RNA motifs," Nucleic Acids Research, Sep. 30, 2015, 43(17):8476-8487.

SantaLucia, "A unified view of polymer, dumbbell, and oligonucleotide DNA nearest-neighbor thermodynamics," Proc Natl Acad Sci USA, Feb. 17, 1998, 95(4): 1460-1465.

Seth et al., "Synthesis and biophysical evaluation of 2',4'-constrained 2'O-methoxyethyl and 2',4'-constrained 2'O-ethyl nucleic acid analogues," Journal of Organic Chemistry, Mar. 5, 2010, 75(5):1569-1581.

Straarup et al., "Short locked nucleic acid antisense oligonucleotides potently reduce apolipoprotein B mRNA and serum cholesterol in mice and non-human primates," Nucleic Acids Research, Nov. 2010, 38(20):7100-7111.

Sugimoto, "Thermodynamic parameters to predict stability of RNA/DNA hybrid duplexes," Biochemistiy, Sep. 5, 1995, 34(35):11211-11216.

Uhlmann, "Recent advances in the medicinal chemistry of antisense oligonucleotides," Current Opinion in Drug Discovery Development, Mar. 2000, 3(2):203-213.

Yamamoto et al., "Serial incorporation of a monovalent GalNAc phosphoramidite unit into hepatocyte-targeting antisense oligonucleotides," Bioorganic & Medicinal Chemistry, Jan. 1, 2016 24(1):26-32.

Vester et al., "Chemically modified oligonucleotides with efficient RNase H response," Bioorganic & Medical Chemistry Letters, Apr. 1, 2008, 18(7):2296-2300.

International Search Report and Written Opinion in Application No. PCT/EP2017/059080, dated Jun. 23, 2017, 14 pages.

* cited by examiner

SEQUENCE LISTING

```
<160> NUMBER OF SEQ ID NOS: 3

<210> SEQ ID NO 1
<211> LENGTH: 13
<212> TYPE: DNA
<213> ORGANISM: Artificial Sequence
<220> FEATURE:
<223> OTHER INFORMATION: oligionucleotide sequence

<400> SEQUENCE: 1
gcattggtat tca                                                      13

<210> SEQ ID NO 2
<211> LENGTH: 15
<212> TYPE: DNA
<213> ORGANISM: Artificial Sequence
```

```
<220> FEATURE:
<223> OTHER INFORMATION: oligonucleotide sequence

<400> SEQUENCE: 2
cagcattggt attca                                                    15

<210> SEQ ID NO 3
<211> LENGTH: 15
<212> TYPE: DNA
<213> ORGANISM: Artificial Sequence
<220> FEATURE:
<223> OTHER INFORMATION: oligonucleotide sequence

<400> SEQUENCE: 3
gcattggtat tcaca                                                    15
```

TRITYL-MONO-GALNAC COMPOUNDS AND THEIR USE

CLAIM OF PRIORITY

This application is a national stage application under 35 U.S.C. § 371 of PCT Application No. PCT/EP2017/059080 filed Apr. 18, 2017, which claims priority to European Patent Application No. 16165303.5, filed Apr. 14, 2016, of which each of these applications are hereby incorporated by reference in their entirety.

FIELD OF THE INVENTION

This invention generally relates to the field of phosphoramidite derivatives. In particular, the invention relates to N-Acetylgalactosamine (GalNAc) compounds, in particular phosphoramidite or phosphonoamidite compounds with a single GalNAc moiety and to conjugates of nucleic acid molecules with such N-Acetylgalactosamine containing molecules. Also provided are methods for preparation of these molecules and possible uses thereof, in particular in medicine.

BACKGROUND OF THE INVENTION

In recent years, approaches have been developed to use nucleic acid molecules in therapy. To favorably influence pharmaceutically relevant properties, the nucleic acid molecules have been conjugated to certain ligands such as peptides, lipids, sterols, and carbohydrates. Nucleic acid conjugates have been extensively evaluated for use in siRNAs, where they are considered essential in order to obtain sufficient in vivo potency. For example, by attachment of a conjugate moiety containing terminal galactose or a derivative thereof to the nucleic acid, thereby targeting the nucleic acid molecule to hepatocytes via binding to the asialoglycoprotein receptor (ASGPR).

The use of conjugate moieties binding to the asialoglycoprotein receptor (ASGPR) to deliver therapeutic double stranded nucleic acid molecules, such as siRNAs, to hepatocytes in the liver has been described in for example WO 2008/131419, WO2009/073809 and WO2011/104169. More recently therapeutic single stranded nucleic acid molecules, such as antisense oligonucleotides, have also been shown to benefit from conjugation to the asialoglycoprotein receptor (ASGPR) targeting moieties, see for example WO2014/118267 and WO 2014/179620.

The asialoglycoprotein receptor (ASGPR) targeting moiety, e.g. a moiety containing N-acetyl-galactoseamine (GalNAc), and the nucleic acid molecule are often produced separately and conjugated afterwards, alternatively the conjugate moiety is attached to the nucleic acid molecule using a custom made on a solid support. There are few disclosures where the GalNAc containing moiety has been incorporated into the nucleic acid molecule in conjunction with the solid phase synthesis of the nucleic acid molecule.

WO 2002/094185 and Matulic-Adamic et al. 2002 (Bioconjugate Chemistry Vol 13(5), pp. 1071-1078), describe solid-phase synthesis of GalNAc conjugates useful for targeting ribozymes to the ASGP receptor as well as synthesis of GalNAc phophoramidites to be used in the conjugation. WO 2015/006740 and Rajeev et al. 2015 (ChemBioChem Vol 16, pp. 903-908), describe solid-phase synthesis of trivalent GalNAc conjugates to the 3' end of a siRNA sense strand using monovalent GalNAc units.

Yamamoto et al. 2016 (Bioorganic & Medicinal Chemistry Vol 24(1), pp. 26-32) describe solid-phase synthesis of monovalent, trivalent and pentavalent GalNAc conjugates to the 3' and 5' end of an LNA antisense oligonucleotide using monovalent GalNAc units. There are indications that some of the molecules introduce hepatotoxicity.

Conventionally, libraries of nucleic acid molecules are screened without conjugation (naked) due to the labour of adding conjugates to each member of the library potentially constituting hundreds of nucleic acid molecules. Conjugation is then conducted once a handful of potent molecules have been selected. It is however known that conjugation can change the potency of a molecule, see for example WO 2015/071388, consequently this approach may lead to deselection of potentially potent molecules.

OBJECTIVE OF THE INVENTION

It was an object of the invention to provide novel conjugate moieties which are easy to produce and purify and which possess flexibility in terms of design. This is particularly relevant when producing screening libraries of therapeutic nucleic acid molecules. Furthermore the nucleic acid conjugates obtained using the novel mono-GalNAc conjugate moieties do not cause hepatotoxicity.

The present inventors have now discovered that the synthesis of carbohydrate nucleic acid conjugates is greatly facilitated by using novel mono-GalNAc compounds, in particular phosphoramidites or phosphonoamidites. These compounds contain a single GalNAc moiety with a linker and a triyl-based hydroxyl protecting group, such as 4,4'-dimethoxytrityl (DMT). This enables the flexible incorporation of multiple or just one GalNAc moiety to either the 5'- or 3'-terminal end (or both ends) of a nucleic acid molecule, in particular an antisense oligonucleotide or siRNA, using solid phase phosphoramidite chemistry and standard supports. The nucleic acid conjugates obtained using the trityl-mono-GalNAc phosphoramidites always contain a trityl group, e.g. triphenylmethyl, methoxytrityl or dimethoxytrityl, at the 5' end of the molecule. This allows for post synthesis purification similar to that of non-conjugated nucleic acid molecules, e.g. on a cartridge. This is especially valuable for making small scale (many compounds in small amounts) libraries of GalNAc conjugated nucleic acid molecules for in vitro screening. It is possibly also an advantage for larger scale synthesis (few compounds in large amounts) of GalNAc-oligonucleotides because post conjugation of a separately produced GalNAc cluster is avoided (see for example EP application No. 15194811.4).

With the current invention only the trityl-mono-GalNAc phosphoramidite needs to be sourced, which is generated in fewer steps than the currently used trivalent GalNAc clusters.

Data has shown that it is possible to achieve comparable activity on mRNA knockdown with trivalent constructs obtained by incorporating the DMT-mono-GalNAc phosphoramidite in the nucleotide synthesis when compared with a trivalent GalNAc cluster.

SUMMARY OF THE INVENTION

In one aspect, the present invention relates to mono-N-acetylgalactosamine (GalNAc) compounds, e.g. phosphoramidites or phosphonoamidites.

In a further aspect, the present invention relates to GalNAc-biomolecule conjugates, particularly GalNAc-nucleic acid conjugates, i.e. molecules comprising one or more (e.g.

a plurality of) GalNAc conjugate moieties which have been covalently bound to a biomolecule, particularly a nucleic acid molecule using phosphoramidite chemistry. By serially connecting mono-GalNAc compounds (conjugate moieties) to a given biomolecule, it is possible to generate a cluster comprising 2, 3 or more GalNAc conjugate moieties. Preferably, three mono-GalNAc compounds have been incorporated into either the 3' end or the 5' end of the nucleic acid molecule.

In a further aspect, the present invention relates to a manufacturing process of trityl-mono-GalNAc compounds, e.g. phosphoramidites or phosphonoamidites.

In yet a further aspect, the invention relates to uses of the described novel trityl-mono-GalNAc compounds.

According to a further aspect, the invention provides medical uses of the compounds according to the invention, in particular of GalNAc-nucleic acid conjugates.

Also provided are methods of treatment comprising administration of compounds according to the invention in a therapeutically or diagnostically effective amount, in particular of GalNAc-nucleic acid conjugates, to a subject in need thereof.

DEFINITIONS

Biomolecule

Figure 1:
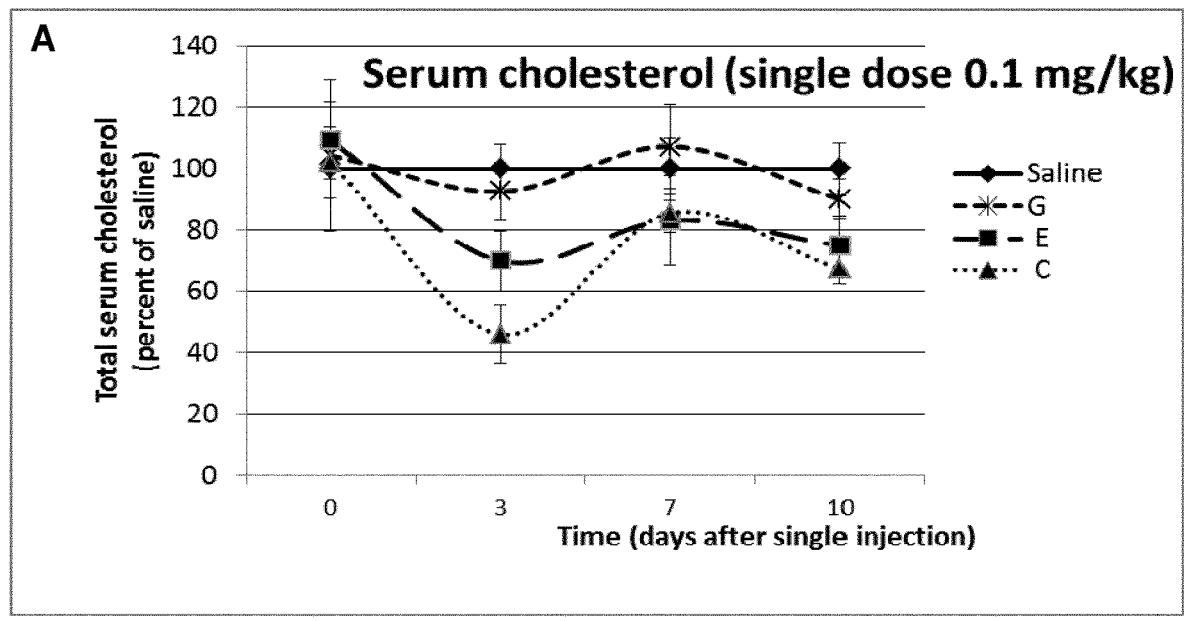
FIG. 1: Total serum cholesterol in mice 10 days after injection of different oligonucleotide conjugates (a) single dose 0.1 mg/kg and (b) single dose 0.25 mg/kg.
Figure 1:
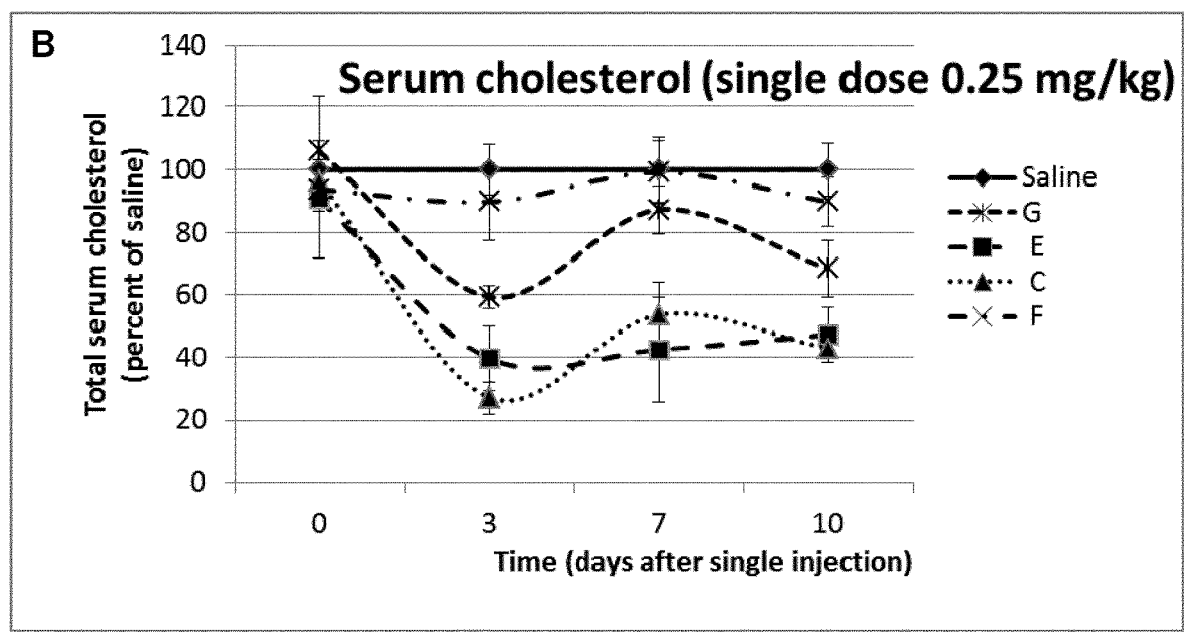

A biomolecule in the context of the present invention is a molecule composed of sugars, lipids, peptides, proteins or nucleic acids or combinations of these substances. Biomolecules can either be isolated from a variety of natural sources—human, animal, or microorganism—or may be produced by fermentation or synthetically. Examples of biomolecules are nucleic acids, in particular antisense oligonucleotides, siRNA molecules or ribozymes; peptides or larger proteins such as antibodies or fragments thereof; hormones; steroids; vitamins; polysaccharides such as hyaluronic acid. Biomolecules are suitable as pharmaceutical drugs, and in the contexts of the present invention in particular suitable for treatments of diseases in the liver.

Conjugate

The term conjugate as used herein refers to a biomolecule (region A or first region) which is covalently linked to a non-nucleotide moiety (conjugate moiety or region C or third region).

Specific conjugates of the invention are nucleic acid conjugates where a nucleic acid molecule (region A or first region), e.g. an oligonucleotide or siRNA, is covalently linked to a non-nucleotide moiety (conjugate moiety or region C or third region), such as a GalNAc conjugate moiety of the present invention. In the present invention the oligonucleotide conjugate is achieved by incorporating one or more mono-GalNAc conjugate moieties of the present invention at the beginning or end of the oligonucleotide synthesis.

Nucleic Acid Molecule

The term "nucleic acid molecule" as used herein is defined as it is generally understood by the skilled person as a molecule comprising two or more covalently linked nucleosides such as DNA (deoxyribonucleic acid), RNA (ribonucleic acid) or modified nucleosides. Nucleic acid molecules can either be single stranded or double stranded, or they can form various substructures like hairpins.

The nucleic acid molecule can be DNA, RNA or may comprise a nucleotide sequence which comprises both DNA and/or RNA nucleosides and modified nucleosides. In particular modified nucleic acid molecules that modulate RNA within a cell are desired. The modulation can for example be facilitating degradation of mRNA, blockage of mRNA transcription, repair of splice sites, prevention of splicing or blockage of micro RNA.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded. In some embodiments, the antisense oligonucleotide does not comprise RNA (units). It is preferred that the compound according to the invention is a linear molecule or is synthesised as a linear molecule. Antisense oligonucleotides are generally between 7 and 50 nucleotides in length, such as 10 to 30 nucleotides in length. In some embodiments, the antisense oligonucleotides comprise or consist of a contiguous nucleotide sequence of a total of from 10-22, such as 10-16, such as 10-14, such as 11-20, such as 12-18, such as 12-16, such as 13-17, or such as 10, 11, 12, 13, 14, 15, 16, 17, 18, 19, 20, 21, 22, 23, 24, 25, 26, 27, 28, 29 or 30 contiguous nucleotides in length.

Interfering RNA (RNAi),

The term "interfering RNA" or "short interfering RNA" or "silencing RNA", is as used herein is defined as double-stranded RNA-like molecules, typically between 15 and 50 nucleotides, such as 20 to 30 nucleotides in length. RNAi polynucleotides may be selected from the group comprising: siRNA, microRNA, double-strand RNA (dsRNA), short hairpin RNA (shRNA), and expression cassettes encoding RNA capable of inducing RNA interference.

An siRNA may be composed of two annealed polynucleotides or a single polynucleotide that forms a hairpin structure. An siRNA molecule of the invention comprises a sense region and an antisense region. The antisense region having a nucleotide sequence identical (perfectly complementary) or nearly identical (partially complementary) to a target nucleic acid.

RNAi molecules is essentially a synthetic, man-made molecule, and operates within the RNA interference (RNAi) pathway, where it interferes with a target nucleic acid with complementary nucleotide sequences by degrading mRNA after transcription, resulting in no translation. The siRNA interacts via a protein complex called Dicer, which dices up siRNA into smaller fragments. One strand of these fragments, in most cases the antisense strand, is loaded into another protein complex called the RNA-induced Silencing Complex (RISC). The strand bound by RISC then links the complex to the target nucleic acid by base pairing. The target nucleic acid is cleaved and destroyed so no protein can be synthesized.

Contiguous Nucleotide Sequence

The term "contiguous nucleotide sequence" refers to the region of the nucleic acid molecule which is complementary to the target nucleic acid. In some embodiments all the nucleotides of the nucleic acid molecule constitute the contiguous nucleotide sequence. In some embodiments the nucleic acid molecule comprises the contiguous nucleotide sequence and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of nucleic acid molecules, such as single stranded oligonucleotides, double stranded nucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers". It will be recognised that when referring to a sequence of nucleotides or monomers, what is referred to is the sequence of bases, such as A, T, G, C or U or analogues thereof.

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers".

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the nucleic acid molecule compared to a phosphodiester linkage. For naturally occurring nucleic acid molecules, the internucleoside linkage includes phosphate groups creating a phosphodiester bond between adjacent nucleosides. Modified internucleoside linkages are particularly useful in stabilizing nucleic acid molecules, in particular nucleic acid molecules, for in vivo use, and may serve to protect against nuclease cleavage at regions of DNA or RNA nucleosides in the nucleic acid molecule, for example within the gap region of a gapmer oligonucleotide, as well as in regions of modified nucleosides.

In an embodiment, the nucleic acid molecule comprises one or more internucleoside linkages modified from the natural phosphodiester to a linkage that is for example more resistant to nuclease attack. Nuclease resistance may be determined by incubating the nucleic acid molecule in blood serum or by using a nuclease resistance assay (e.g. snake venom phosphodiesterase (SVPD)), both are well known in the art. Internucleoside linkages which are capable of enhancing the nuclease resistance of a nucleic acid molecule are referred to as nuclease resistant internucleoside linkages. In some embodiments at least 50% of the internucleoside linkages in the nucleic acid molecule, or contiguous nucleotide sequence thereof, are modified, such as at least 60%, such as at least 70%, such as at least 80 or such as at least 90% of the internucleoside linkages in the nucleic acid molecule, or contiguous nucleotide sequence thereof, are modified. In some embodiments all of the internucleoside linkages of the nucleic acid molecule, or contiguous nucleotide sequence thereof, are modified. It will be recognized that, in some embodiments the nucleosides which link the nucleic acid molecule to a non-nucleotide functional group, such as a conjugate, may be phosphodiester. In some embodiments all of the internucleoside linkages of the nucleic acid molecule, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In some embodiments at least 50% of the internucleoside linkages in the nucleic acid molecule, or contiguous nucleotide sequence thereof, are phosphorothioate, such as at least 60%, such as at least 70%, such as at least 80 or such as at least 90% of the internucleoside linkages in the nucleic acid molecule, or contiguous nucleotide sequence thereof, are phosphorothioate. In some embodiments all of the internucleoside linkages of the nucleic acid molecule, or contiguous nucleotide sequence thereof, are phosphorothioate.

In some embodiments, the nucleic acid molecule comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—

—O—, —S—P(S)₂—O—, —O—P(O)₂—S—, —O—P(O, S)—S—, —S—P(O)₂—S—, —O—PO(R^H)—O—, O—PO (OCH₃)—O—, —O—PO(NR^H)—O—, —O—PO (OCH₂CH₂S—R)—O—, —O—PO(BH₃)—O—, —O—PO (NHR^H)—O—, —O—P(O)₂—NR^H—, —NR^H—P(O)₂—O—, —NR^H—CO—O—, —NR^H—CO—NR^H—, and/or the internucleoside linker may be selected form the group consisting of: —O—CO—O—, —O—CO—NR^H—, —NR^H—CO—CH₂—, —O—CH₂—CO—NR^H—, —O—CH₂—CH₂—NR^H—, CO—NR^H—CH₂—, —CH₂—NR^H CO—, —O—CH₂—CH₂—S—, —S—CH₂—CH₂—O—, —S—CH₂—CH₂—S—, —CH₂—SO₂—CH₂—, —CH₂—CO—NR^H—, —O—CH₂—CH₂—NR^H—CO—, —CH₂—NCH₃—O—CH₂—, where R^H is selected from hydrogen and C1-4-alkyl.

Nuclease resistant linkages, such as phosphorothioate linkages (PS linkages), are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particular in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the nucleic acid molecule are phosphorothioate and/or boranophosphate linkages. Preferably, all the internucleoside linkages in the nucleic acid molecule are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified nucleic acid molecules, the nucleobase moieties are selected from A, T, G, C, and 5-methyl cytosine. Optionally, for LNA gapmers, 5-methyl cytosine LNA nucleosides may be used.

Modified Nucleic Acid Molecule

The term modified nucleic acid molecule describes a nucleic acid molecule comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that nucleic acid molecules may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide or siRNA) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences, dividing by the total number of nucleotides in the nucleic acid molecule and multiplying by 100. In such a comparison a nucleobase/nucleotide which does not align (form a base pair) is termed a mismatch.

The term "fully complementary", refers to 100% complementarity.

Identity

The term "Identity" as used herein, refers to the number of nucleotides in percent of a contiguous nucleotide sequence in a nucleic acid molecule (e.g. oligonucleotide or sense or antisense strand of an siRNA) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences, including gaps, dividing by the total number of nucleotides in the nucleic acid molecule and multiplying by 100. Percent Identity=(Matches×100)/Length of aligned region (with gaps).

Hybridization

The term "hybridizing" or "hybridizes" as used herein is to be understood as two nucleic acid strands (e.g. an oligonucleotide and a target nucleic acid or an siRNA antisense strand with a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy ΔG° is a more accurate representation of binding affinity and is related to the dissociation constant ($K_d$) of the reaction by ΔG°=-RTln($K_d$), where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for ΔG° measurements. ΔG° can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Nucleic Acid

According to the present invention, a target nucleic acid represents a nucleic acid which it is desirable to modulate the function of in a cell line or mammal. In preferred embodiments the modulation of the target nucleic acid changes the pathology of interest.

The target nucleic acid, can be a DNA or RNA encoding a mammalian target polypeptide, such as human a target polypeptide or a non-coding DNA or RNA molecule exerting a regulatory effect on mechanisms within a cell, such as viral infection mechanisms, RNA silencing or post-transcriptional regulation of gene expression. Non-coding RNA molecules can for example be micro RNA snRNA, snoRNA, or long non-coding RNA's. In preferred embodiments the target nucleic acid is a gene, a viral RNA, a mRNA, and pre-mRNA, a mature mRNA or a cDNA sequence or micro RNA (miRNA) present in a cell, such as a mammalian cell in particular a human cell in vitro or in vivo.

Target Cell

The term a "target cell" as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell. In preferred embodiments the target cell has asialoglycoprotein receptors (ASPGR) on the surface, such as liver cells and testis cells, in particular hepatocytes and Leydig cells.

Modulation of Expression

The term "modulation of expression" as used herein is to be understood as an overall term for a nucleic acid molecule ability to alter the amount of a target nucleic acid when compared to the amount of target nucleic acid before administration of the nucleic acid molecule. Alternatively modulation of expression may be determined by reference to a control experiment. It is generally understood that the control is an individual or target cell treated with a saline composition or an individual or target cell treated with a non-targeting nucleic acid molecule (mock). It may however also be an individual treated with the standard of care.

One type of modulation is a nucleic acid molecule's ability to inhibit, down-regulate, reduce, suppress, remove, stop, block, prevent, lessen, lower, avoid or terminate expression of a target nucleic acid, e.g. by degradation of mRNA or blockage of transcription. Another type of modulation is a nucleic acid molecule's ability to restore, increase or enhance expression target nucleic acid, e.g. by repair of splice sites or prevention of splicing or removal or blockage of inhibitory mechanisms such as microRNA repression.

High Affinity Modified Nucleosides

A high affinity modified nucleoside is a modified nucleotide which, when incorporated into the nucleic acid molecule enhances the affinity of the nucleic acid molecule for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of nucleic acid molecules, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into nucleic acid molecules, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the nucleic acid molecule. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

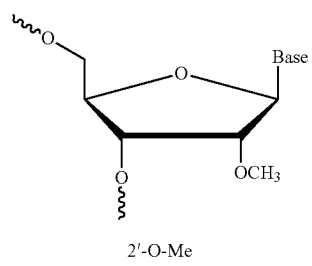

2'-O-Me

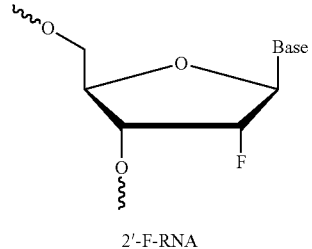

2'-F-RNA

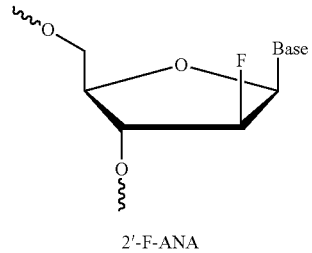

2'-F-ANA

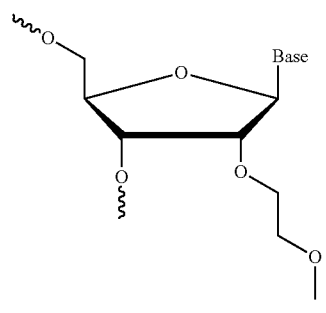

2'-O-MOE

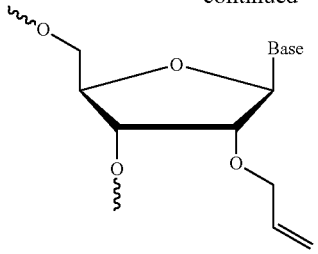

2'-O-Allyl

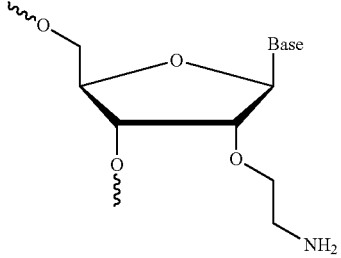

2'-O-Ethylamine

Locked Nucleic Acid Nucleosides (LNA).

LNA nucleosides are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

In some embodiments, the modified nucleoside or the LNA nucleosides of the oligomer of the invention has a general structure of the formula I or II:

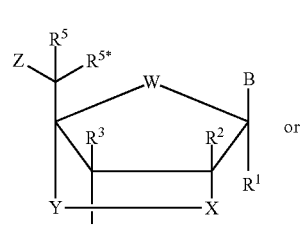

β-D

Formula XIII

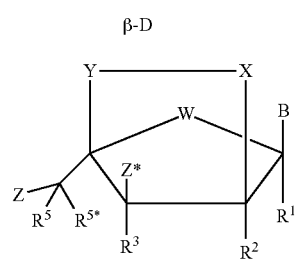

α-L

Formula XIV wherein W is selected from —O—, —S—, —N($R^a$)—, —C($R^a R^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, NR$^a$R$^b$, —CH$_2$—, CR$^a$R$^b$, —C(=CH$_2$)—, and —C(=CR$^a$R$^b$)—

In some embodiments, X is —O—

Y designates a group selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z In some embodiments, Y is selected from the group consisting of: —CH$_2$—, —C(R$^a$R$^b$)—, —CH$_2$CH$_2$—, —C(R$^a$R$^b$)—C(R$^a$R$^b$)—, —CH$_2$CH$_2$CH$_2$—, —C(R$^a$R$^b$)C(R$^a$R$^b$)C(R$^a$R$^b$)—, —C(R$^a$)=C(R$^b$)—, and —C(R$^a$)=N—

In some embodiments, Y is selected from the group consisting of: —CH$_2$—, —CHR$^a$—, —CHCH$_3$—, CR$^a$R$^b$— or —X—Y— together designate a bivalent linker group (also referred to as a radicle) together designate a bivalent linker group consisting of 1, 2, 3 or 4 groups/atoms selected from the group consisting of —C(R$^a$R$^b$)—, —C(R$^a$)=C(R$^b$)—, —C(R$^a$)=N—, —O—, —Si(R$^a$)$_2$—, —S—, —SO$_2$—, —N(R$^a$)—, and >C=Z, In some embodiments, —X—Y— designates a biradicle selected from the groups consisting of: —X—CH$_2$—, —X—CR$^a$R$^b$—, —X—CHR$^a$—, —X—C(HCH$_3$), —O—Y—, —O—CH$_2$—, —S—CH$_2$—, —NH—CH$_2$—, —O—CHCH$_3$—, —CH$_2$—O—CH$_2$—, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—CR$^a$R$^b$— and —S—CHR$^a$—.

In some embodiments —X—Y— designates —O—CH$_2$— or —O—CH(CH$_3$)—.

wherein Z is selected from —O—, —S—, and —N(R$^a$)—, and R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkyl-thio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation.

wherein R$^1$, R$^2$, R$^3$, R$^5$ and R$^{5*}$ are independently selected from the group consisting of: hydrogen, optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments R$^1$, R$^2$, R$^3$, R$^5$ and R$^{5*}$ are independently selected from C$_{1-6}$ alkyl, such as methyl, and hydrogen.

In some embodiments R$^1$, R$^2$, R$^3$, R$^5$ and R$^{5*}$ are all hydrogen.

In some embodiments R$^1$, R$^2$, R$^3$, are all hydrogen, and either R$^5$ and R$^{5*}$ is also hydrogen and the other of R$^5$ and R$^{5*}$ is other than hydrogen, such as C$_{1-6}$ alkyl such as methyl.

In some embodiments, R$^a$ is either hydrogen or methyl. In some embodiments, when present, R$^b$ is either hydrogen or methyl.

In some embodiments, one or both of R$^a$ and R$^b$ is hydrogen

In some embodiments, one of R$^a$ and R$^b$ is hydrogen and the other is other than hydrogen In some embodiments, one of R$^a$ and R$^b$ is methyl and the other is hydrogen In some embodiments, both of R$^a$ and R$^b$ are methyl.

In some embodiments, the biradicle —X—Y— is —O—CH$_2$—, W is O, and all of R$^1$, R$^2$, R$^3$, R$^5$ and R$^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—CH$_2$—, W is O, and all of R$^1$, R$^2$, R$^3$, R$^5$ and R$^{5*}$ are all hydrogen. Such thio LNA nucleosides are disclosed in WO99/014226 and WO2004/046160 which are hereby incorporated by reference.

In some embodiments, the biradicle —X—Y— is —NH—CH$_2$—, W is O, and all of R$^1$, R$^2$, R$^3$, R$^5$ and R$^{5*}$ are all hydrogen. Such amino LNA nucleosides are disclosed in WO99/014226 and WO2004/046160 which are hereby incorporated by reference.

In some embodiments, the biradicle —X—Y— is —O—CH$_2$—CH$_2$— or —O—CH$_2$—CH$_2$—CH$_2$—, W is O, and all of R$^1$, R$^2$, R$^3$, R$^5$ and R$^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—CH$_2$—, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such 5' substituted LNA nucleosides are disclosed in WO2007/134181 which is hereby incorporated by reference.

In some embodiments, the biradicle —X—Y— is —O—CR$^a$R$^b$—, wherein one or both of R$^a$ and R$^b$ are other than hydrogen, such as methyl, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—CH(CH$_2$OCH$_3$)— (2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—CH(CH$_2$CH$_3$)— (2'O-ethyl bicyclic nucleic acid—Seth at al., 2010, J. Org. Chem. Vol 75(5) pp. 1569-81). In some embodiments, the biradicle —X—Y— is —O—CHR$^a$—, W is O, and all of R$^1$, R$^2$, R$^3$, R$^5$ and R$^{5*}$ are all hydrogen. Such 6' substituted LNA nucleosides are disclosed in WO10036698 and WO07090071 which are both hereby incorporated by reference.

In some embodiments, the biradicle —X—Y— is —O—CH(CH$_2$OCH$_3$)—, W is O, and all of R$^1$, R$^2$, R$^3$, R$^5$ and R$^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)—.—in either the R- or S- configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH (CH$_3$)—, W is O, and all of R$^1$, R$^2$, R$^3$, R$^5$ and R$^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—CR$^a$R$^b$—, wherein in neither R$^a$ or R$^b$ is hydrogen, W is O, and all of R$^1$, R$^2$, R$^3$, R$^5$ and R$^{5*}$ are all hydrogen. In some embodiments, R$^a$ and R$^b$ are both methyl. Such 6' di-substituted LNA nucleosides are disclosed in WO 2009006478 which is hereby incorporated by reference.

In some embodiments, the biradicle —X—Y— is —S—CHR$^a$—, W is O, and all of R$^1$, R$^2$, R$^3$, R$^5$ and R$^{5*}$ are all hydrogen. Such 6' substituted thio LNA nucleosides are disclosed in WO11156202 which is hereby incorporated by reference. In some 6' substituted thio LNA embodiments R$^a$ is methyl.

In some embodiments, the biradicle —X—Y— is —C(=CH2)—C(R$^a$R$^b$)—, such as —C(=CH$_2$)—CH$_2$—, or —C(=CH$_2$)—CH(CH$_3$)—W is O, and all of R$^1$, R$^2$, R$^3$, R$^5$ and R$^{5*}$ are all hydrogen. Such vinyl carbo LNA nucleosides are disclosed in WO08154401 and WO09067647 which are both hereby incorporated by reference.

In some embodiments the biradicle —X—Y— is —N(—OR$^a$)—, W is O, and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^2$)—, W is O, and all of R$^1$, R$^2$, R$^3$, R$^5$ and R$^{5*}$ are all hydrogen. In some embodiments R$^a$ is C$_{1-6}$ alkyl such as methyl.

In some embodiments, one or both of R$^5$ and R$^{5*}$ is hydrogen and, when substituted the other of R$^5$ and R$^{5*}$ is C$_{1-6}$ alkyl such as methyl. In such an embodiment, R$^1$, R$^2$, R$^3$, may all be hydrogen, and the biradicle —X—Y— may be selected from —O—CH2- or —O—C(HCR$^a$)—, such as —O—C(HCH3)—.

In some embodiments, the biradicle is —CR$^a$R$^b$—O—CR$^a$R$^b$—, such as CH$_2$—O—CH$_2$—, W is O and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—CR$^a$R$^b$—O—CR$^a$R$^b$—, such as O—CH$_2$—O—CH$_2$—, W is O and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

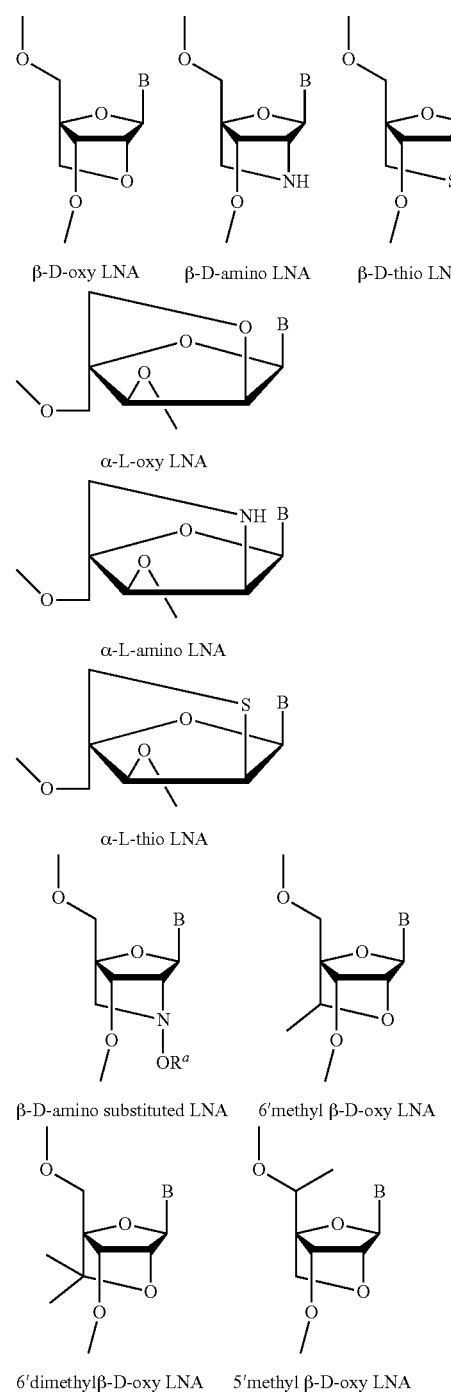

Scheme 1

β-D-oxy LNA    β-D-amino LNA    β-D-thio LNA

α-L-oxy LNA

α-L-amino LNA

α-L-thio LNA

β-D-amino substituted LNA    6'methyl β-D-oxy LNA

6'dimethylβ-D-oxy LNA    5'methyl β-D-oxy LNA

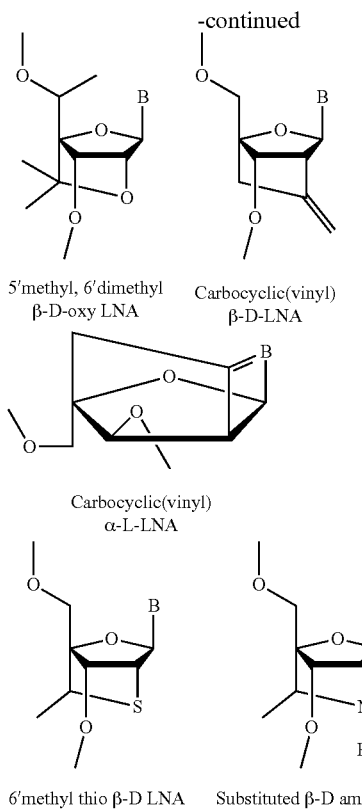

5′methyl, 6′dimethyl
β-D-oxy LNA

Carbocyclic(vinyl)
β-D-LNA

Carbocyclic(vinyl)
α-L-LNA

6′methyl thio β-D LNA     Substituted β-D amino LNA

As illustrated in the examples, in some embodiments of the invention the LNA nucleosides in the nucleic acid molecules are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference).

Gapmer

The term gapmer as used herein refers to an antisense oligonucleotide which comprises a region of RNase H recruiting oligonucleotides (gap) which is flanked 5' and 3' by regions which comprise one or more affinity enhancing modified nucleosides (flanks or wings). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flank comprises affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer or mixed flank gapmer refers to a LNA gapmer wherein at least one of the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises only LNA nucleosides (e.g. 5' or 3') and the other flank (3' or 5' respectfully) comprises 2' substituted modified nucleoside(s) and optionally LNA nucleosides.

Gapbreaker

The term "gapbreaker oligonucleotide" is used in relation to a gapmer capable of maintaining RNAseH recruitment even though the gap region is disrupted by a non-RNaseH recruiting nucleoside (a gap-breaker nucleoside, E) such that the gap region comprise less than 5 consecutive DNA nucleosides. Non-RNaseH recruiting nucleosides are for example nucleosides in the 3' endo conformation, such as LNA's where the bridge between C2' and C4' of the ribose sugar ring of a nucleoside is in the beta conformation, such as beta-D-oxy LNA or ScET nucleoside. The ability of gapbreaker oligonucleotide to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA.

In some embodiments, the oligonucleotide of the invention is a gapbreaker oligonucleotide. In some embodiments the gapbreaker oligonucleotide comprise a 5'-flank (F), a gap (G) and a 3'-flank (F'), wherein the gap is disrupted by a non-RNaseH recruiting nucleoside (a gap-breaker nucleoside, E) such that the gap contain at least 3 or 4 consecutive DNA nucleosides. In some embodiments the gapbreaker nucleoside (E) is an LNA nucleoside where the bridge between C2' and C4' of the ribose sugar ring of a nucleoside is in the beta conformation and is placed within the gap region such that the gap-breaker LNA nucleoside is flanked 5' and 3' by at least 3 (5') and 3 (3') or at least 3 (5') and 4 (3') or at least 4(5') and 3(3') DNA nucleosides, and wherein the oligonucleotide is capable of recruiting RNaseH.

The gapbreaker oligonucleotide can be represented by the following formulae:

F-G-E-G-F'; in particular $F_{1-7}$-$G_{3-4}$-$E_1$-$G_{3-4}$-$F'_{1-7}$

D'-F-G-F', in particular $D'_{1-3}$-$F_{1-7}$-$G_{3-4}$-$E_1$-$G_{3-4}$-$F'_{1-7}$ F-G-F'-D", in particular $F_{1-7}$-$G_{3-4}$-$E_1$-$G_{3-4}$-$F'_{1-7}$-$D''_{1-3}$ D'-F-G-F'-D", in particular $D'_{1-3}$-$F_{1-7}$-$G_{3-4}$-$E_1$-$G_{3-4}$-$F'_{1-7}$-$D''_{1-3}$ Where region D' and D" are as described in the section "Gapmer design".

In some embodiments the gapbreaker nucleoside (E) is a beta-D-oxy LNA or ScET or another beta-LNA nucleosides shown in Scheme 1).

Biocleavable Linker

A "biocleavable linker" according to the invention comprises or consists of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference). The linkages between the GalNAc conjugate moieties are in certain embodiments biocleavable phosphodiester linkages (see for example formulas (VII) or (VIII)), in addition to this phosphodiester linkage further phosphodiester linkages may be introduced by inserting for example a phosphodiester linked, nucleoside, dinucleotide or trinucleotide between the antisense oligonucleotide complementary to a target and the GalNAc moiety. In preferred embodiments the phosphodiester linked dinucleotide is a deoxycytidine-deoxyadenosine (ca) dinucleotide.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

DETAILED DESCRIPTION OF THE INVENTION

Trityl-Mono-GalNAc Compounds

In one aspect, the invention relates to novel mono-N-acetylgalactosamine (GalNAc) compounds. Accordingly, the invention provides a compound having the general formula (I) including any salt thereof, wherein the compound is represented by:

(I)

wherein $R^1$ is H or $C_{1-6}$ alkyl;
$R^2$ is a triphenylmethyl-based hydroxyl protecting group,
$R^3$ is a phosphorus-containing group, particularly a phosphoramidite or a phosphonoamidite group, and K is represented by the general formula (II)

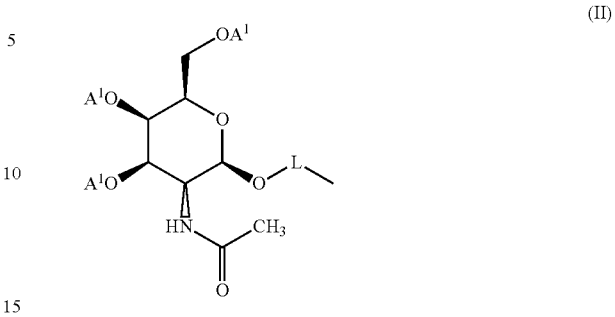

(II)

wherein $A^1$ is a hydroxyl protecting group, which may be the same or different at each occurrence and L is a linker.

The compound of formula (I) is chiral and possesses at least one asymmetric carbon atom or enantiomeric center. The present invention encompasses all enantiomers of compounds of formula (I) as well as all possible mixtures thereof.

L is a linker group having in particular a chain length of from 2-30 atoms which are selected from carbon atoms and optionally heteroatoms such as N and/or O atoms. L is selected according to the desired application of the GalNAc compound. It has been shown in PCT/EP2015/073331 that the linker length is surprisingly flexible in terms of generating functional GalNAc clusters. In some embodiments, the chain may contain one or more —NH—CO—, —CO—NH— groups and/or heteroatoms, particularly O. The number of replacements should be adapted such that the total length of the linker does not exceed 30 atoms after replacements and maintaining at least one neighbouring atom to the replacements as carbon atoms in the case of —NH—CO—, —CO—NH and at least 2 neighbouring carbon atoms in the case of heteroatom replacements. In some embodiments the number of replacements is less than 5 and the neighbouring atoms to the replacements are carbon atoms. In some embodiments no more than one or two replacements are made in the chain and the neighbouring atoms to the replacements are carbon atoms. For example, the linker between the GalNAc and the phosphoramidite may be derived from a simple diol. In principle, any symmetrical or unsymmetrical diol could be used as a linker in the GalNAc phosphoramidite of the invention, provided it contains no other nucleophilic groups. In some embodiments, carbon atoms in the chain are replaced by oxygen atoms in order to form an array of —(CH$_2$CH$_2$O)—groups.

In certain embodiments, L is selected from the group consisting of $C_2$-$C_{30}$-alkylene, $C_2$-$C_{30}$-alkenylene, and —(CH$_2$)$_{0-8}$(CH$_2$CH$_2$O)$_{0-8}$—(CH$_2$)$_{0-4}$— (wherein the individual groups are selected such that L contains at least 2 C-atoms), each attached to a carbonyl group (—C(O)—). More specifically, the linker group L may be selected from the group consisting of —(CH$_2$)$_m$—C(O)—, wherein m=2-12, particularly 4, 5 or 11; —(CH$_2$—CH$_2$—O)$_n$—CH$_2$—C(O)—, wherein n=1-5, particularly 2, 3 or 4 and more particularly 3; —(CH$_2$)$_{m1}$—CO—NH—(CH$_2$)$_{m2}$—NH—C(O)—, wherein m1 and m2 each independently is 1-5, particularly 3, 4 or 5; —(CH$_2$)$_{m3}$—CO—NH—(CH$_2$)$_{m4}$—C(O)—, wherein m3 and m4 each independently is 1-5, particularly 3, 4 or 5; —(CH$_2$)$_{m6}$—NH—C(O)—, wherein m6 is 2-12, particularly 12; and wherein in each case C(O)— is attached to NR$^1$.

Particularly, the linker group L may be selected from the group consisting of —(CH$_2$)$_4$—C(O)—, —(CH$_2$)$_5$—C(O)—, —(CH$_2$)$_{11}$—C(O)—, —(CH$_2$)$_6$—NH—C(O)—, —(CH$_2$)$_{12}$—NH—C(O)—, —(CH$_2$)$_5$—CO—NH—(CH$_2$)$_5$—C(O)—, —(CH$_2$)$_4$—CO—NH—(CH$_2$)$_3$—NH—C(O)—, —(CH$_2$)$_4$—CO—NH—(CH$_2$)$_4$—NH—C(O)—, —(CH$_2$)$_5$—CO—NH—(CH$_2$)$_3$—NH—C(O)—, —(CH$_2$)$_5$—CO—NH—(CH$_2$)$_4$—NH—C(O)—, —(CH$_2$)$_6$—NH—CO—CH$_2$—NH—C(O)—, —(CH$_2$CH$_2$O)$_2$—(CH$_2$)$_2$—NH—C(O)—, wherein in each case C(O)— is attached to NR$^1$. According to one preferred embodiment, L is a triethyleneglycol (TEG)-acetate linker represented by the formula (CH$_2$CH$_2$O)$_3$—CH$_2$—C(O)—, wherein C(O)— is attached to NR$^1$.

The GalNAc moiety can be either in the alpha or the beta configuration. In preferred embodiments, the GalNAc moiety is in the beta configuration.

The term "GalNAc moiety" as used herein is the N-Acetylgalactosamine (GalNAc) part of a structure comprising GalNAc. For example, in formula (II) the GalNAc moiety is the part of the molecule which does not constitute the L.

The term "GalNAc conjugate moiety" as used herein, refers to a molecule comprising at least one GalNAc moiety and which can be conjugated to a biomolecule, in particular a nucleic acid, which may be used as a drug in the treatment of certain diseases. Preferably, the GalNAc conjugate moiety has affinity towards the asialoglycoprotein receptor.

R$^1$ in formula (I) is selected from hydrogen and C$_1$-C$_6$-alkyl, in particular from hydrogen, methyl, ethyl, propyl, isopropyl, n-butyl, sec-butyl, t-butyl, n-pentyl and n-hexyl. In certain preferred embodiments, R$^1$ is hydrogen.

R$^2$ in formula (I) is a triphenylmethyl-based hydroxyl protecting group. In particular, R$^2$ is selected from triphenylmethyl, methoxytrityl and dimethoxytrityl. In certain preferred embodiments, R$^2$ is dimethoxytrityl (DMT).

R$^3$ in formula (I) is a phosphorus-containing group. The term "phosphorus containing group" or "phosphoramidite" as used herein means any compound containing a phosphorus atom in oxidation state III which is bound covalently to at least one nitrogen atom. Preferred phosphoramidites of the invention are compounds containing a phosphorus atom in oxidation state III which is bound covalently to at least one nitrogen atom and two oxygen atoms ("phosphoramidites sensu stricto"). Alternatively, phosphoramidites of the invention are compounds containing a phosphorus atom in oxidation state III which is bound covalently to at least one nitrogen atom and one oxygen atom and instead of a second oxygen has a sulphur atom ("thiophosphoramidites") or a C$_1$-C$_6$-alkyl group ("phosphonoamidites").

In certain embodiments, R$^3$ is represented by the general formula (III):

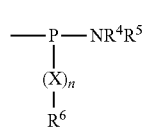

(III)

wherein R$^4$ and R$^5$ are independently selected from C$_{1-6}$ alkyl or R$^4$ and R$^5$ together from a five- or six-membered ring, which may be substituted and which may contain one further heteroatom selected from N and O; X is O or S; n is 0 or 1; and R$^6$ is C$_{1-8}$ alkyl optionally substituted with thio, oxo, halo and/or CN.

In certain embodiments, R$^4$ and R$^5$ of the amino group —NR$^4$R$^5$ in formula (III) are independently selected from C$_1$-C$_6$-alkyl, in particular from methyl, ethyl, propyl, isopropyl, n-butyl, sec-butyl, t-butyl, n-pentyl and n-hexyl. In particular embodiments, R$^4$ is identical to R$^5$, and —NR$^4$R$^5$ then preferably is selected from the group consisting of dimethylamino, diethylamino, diisopropylamino, and dibutylamino. In a preferred embodiment R$^4$ and R$^5$ each are isopropyl.

In other embodiments, R$^4$ and R$^5$ together form a five- or six-membered ring, which may be substituted and which may contain one further heteroatom selected from N and O. In some embodiments, R$^4$ and R$^5$ form an unsubstituted five-membered ring, in other embodiments, they form an unsubstituted six-membered ring. In still further embodiments, the five-membered or six-membered ring is substituted at one or more carbon atoms. For example, the ring may be substituted at one, two, three or four carbon atoms, preferably at one or two carbon atoms. Preferred substituents are methyl and ethyl. In particular, the ring is selected from the group consisting of pyrrolidino, piperidino, 2,6-dimethylpiperidino, morpholino, imidazolyl and 4-methylimidazolyl.

The moiety XR$^6$ in formula (III) is, according to some embodiments, selected from C$_1$-C$_6$-alkyl, in particular from the group consisting of methyl and ethyl.

In further embodiments, XR$^6$ is a protected hydroxy group (—OH) or a protected thio group (—SH). Exemplary non-limited protected hydroxy groups are ether groups, exemplary non-limited protected thio groups are thioether groups. In particular, the protected —OH or —SH group represented by XR$^6$ is selected from the group consisting of 2-cyanoethoxy, 2-cyanoethylthio, methoxy, ethoxy, S-isobutanoyl-2-(2-mercapto-ethoxy)ethoxy, S-pivaloyl-2-(2-mercapto-ethoxy)ethoxy, and S-pivaloyl-2-mercaptoethoxy. In a preferred embodiment, XR$^6$ is a 2-cyanoethoxy group.

In certain preferred embodiments, NR$^4$R$^5$ is selected from dimethylamino, diethylamino, di-n-propylamino, diisopropylamino, dibutylamino, pyrrolidino, piperidino, 2,6-dimethylpiperidino, morpholino, imidazolyl, and 4-methylimidazolyl and XR$^6$ is selected from methyl, ethyl, 2-cyanoethyloxy, 2-cyanoethylthio, methoxy, ethoxy, S-isobutanoyl-2-(2-mercaptoethoxy)ethoxy, S-pivaloyl-2-(2-mercaptoethoxy)ethoxy, and S-pivaloyl-2-mercaptoethoxy. According to one embodiment, NR$^4$R$^5$ is diisopropylamino and XR$^6$ is 2-cyanoethoxy.

For the hydroxyl protecting group A$^1$ in formula (II), a lot of different possibilities are available. The skilled person will know how to choose a protecting group that is stable to the reaction conditions used in the process for preparing the phosphoramidite, and the coupling and oxidation step of the oligonucleotide synthesis process. As example for a suitable hydroxyl protecting group A$^1$ according to formula (II), acyl groups and silyl groups may be mentioned. Preferably, the protecting group A$^1$ is selected from the group consisting of acetyl, benzoyl, phenoxy-acetyl, dimethoxytrityl (DMT), pivaloyl, isobutyryl, t-butyldimethylsilyl, t-butyldiphenylsilyl, triisopropylsilyl and isopropyldimethylsilyl.

In some embodiments, acetyl is used as the protecting group $A^1$. When GalNAc phosphoramidites according to formula (I) are used in the synthesis of nucleic acid conjugates, the acetyl groups may be removed together with the protecting groups of the nucleic acid, e.g. LNA or DNA, in the cleavage and deprotecting step normally used in e.g. LNA synthesis.

In some embodiments, dimethoxytrityl (DMT) is used as the protecting group $A^1$ at carbon atom 6 of the GalNAc moiety. The advantage of using DMT at this position is that it allows for easy separation of failure sequences (e.g. non-complete constructs where a failure in the synthesis has resulted in the GalNAc moiety not being added) during purification.

In some embodiments the trityl-mono-GalNAc phosphoramidite of the invention is represented by formula (XVI)

(O)—, —(CH$_2$)$_4$—CO—NH—(CH$_2$)$_4$—NH—C(O)—, —(CH$_2$)$_5$—CO—NH—(CH$_2$)$_3$—NH—C(O)—, —(CH$_2$)$_5$—CO—NH—(CH$_2$)$_4$—NH—C(O)—, —(CH$_2$)$_6$—NH—CO—CH$_2$—NH—C(O)—, —(CH$_2$CH$_2$O)$_2$—(CH$_2$)$_2$—NH—C(O)—, wherein in each case C(O)— is attached to N. According to one preferred embodiment, L is a triethyleneglycol (TEG)-acetate linker represented by the formula (CH$_2$CH$_2$O)$_3$—CH$_2$—C(O)—, wherein C(O)— is attached to N.

In specific embodiments according to the invention, the compound has the general formula (I), wherein $R^1$ is H, $R^2$ is 4,4'-dimethoxytrityl, $R^3$ is represented by formula (III), wherein $NR^4R^5$ is diisopropylamino and $XR^6$ is 2-cyanoethoxy, and K is represented by formula (II), wherein L is TEG-acetate and $A^1$ is acetyl.

In one embodiment the trityl-mono-GalNAc phosphoramidite of the invention is represented by formula (XV)

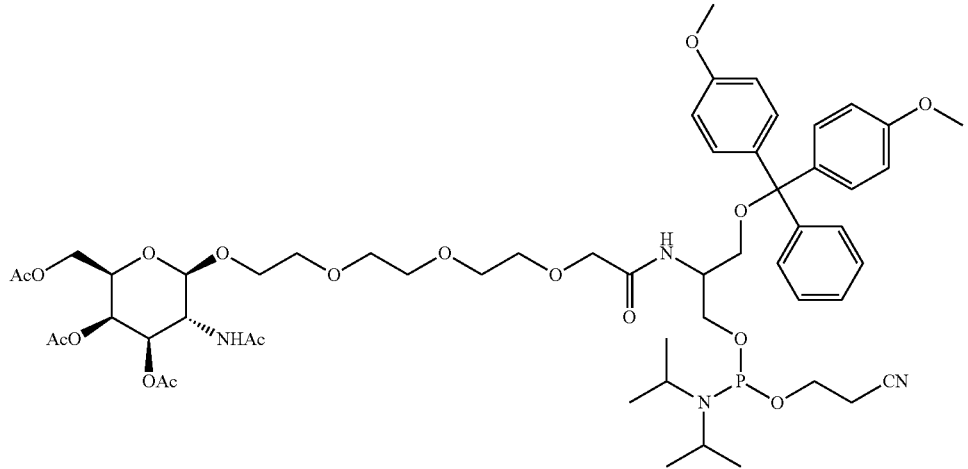

(XV)

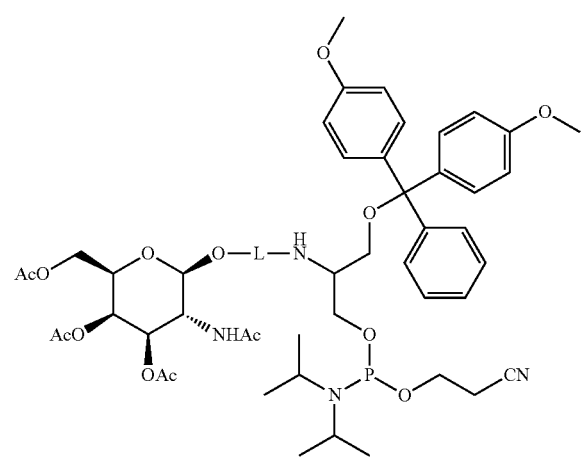

(XVI)

Wherein L is the linker is selected from the group consisting of —(CH$_2$)$_4$—C(O)—, —(CH$_2$)$_5$—C(O)—, —(CH$_2$)$_{11}$—C(O)—, —(CH$_2$)$_6$—NH—C(O)—, —(CH$_2$)$_{12}$—NH—C(O)—, —(CH$_2$)$_5$—CO—NH—(CH$_2$)$_5$—C(O)—, —(CH$_2$)$_4$—CO—NH—(CH$_2$)$_3$—NH—C In one embodiment the trityl-mono-GalNAc phosphormaidite of the invention is (2R,3R,4R,5R,6R)-5-acetamido-2-(acetoxymethyl)-6-((4-((((2-cyanoethoxy) (diisopropylamino) phosphanyl)oxy)methyl)-1,1-bis(4-methoxyphenyl)-6-oxo-1-phenyl-2,8,11,14-tetraoxa-5-azahexadecan-16-yl)oxy)tetrahydro-2H-pyran-3,4-diyl diacetate.

GalNAc Conjugates

In a further aspect, the present invention relates to novel GalNAc conjugates, such as biomolecule-GalNAc conjugates, in particular GalNAc-nucleic acid conjugates. The mono-GalNAc compounds described above can be used to generate conjugates of mono-GalNAc moieties with biomolecules. The GalNAc conjugate moieties can modify or enhance the pharmacokinetic and pharmacodynamic properties of the attached biomolecule, in particular attached nucleic acids.

While the coupling of the mono-GalNAc compounds of the invention is described primarily with regard to nucleic acid molecules herein, it is to be understood that an analogous coupling is possible with other biomolecules as well.

According to the invention, the use of a compound of general formula (I) according to any one of claims 1-11 as a building block for incorporation into biomolecules, particularly into nucleic acid molecules is envisaged. In certain embodiments, this use may have the effect that the biomolecule into which the compound of the general formula (I) has been incorporated, has an increased efficacy. In particular, the modified biomolecule shows enhanced pharmacokinetic and pharmacodynamic properties. For example, the compound increases the effect of the biomolecule in the liver, in particular in the hepatocytes when compared to the biomolecule without the GalNAc compound.

As mentioned above, nucleic acid molecules are biomolecules of particular interest according to the present invention. Accordingly, the invention relates in one aspect to a nucleic acid molecule having attached to the 5'-terminus and/or the 3'-terminus thereof at least one building block derived from a compound of general formula (I) as defined herein. In some embodiments, the at least one building block derived from a compound of general formula (I), i.e. derived from a trityl-mono-GalNAc phosphoramidite, is attached to the 5'-terminus of a nucleic acid molecule, such as 2 GalNAc compounds, such as 3 GalNac compounds, such as 4 GalNAc compounds, such as 5 GalNAc compounds attached to the 5' end of the nucleic acid molecule. In other embodiments, the at least one building block derived from a compound of general formula (I), is attached to the 3'-terminus of a nucleic acid molecule. In still further embodiments, at least one building block derived from a compound of general formula (I) is attached to the 5'-terminus and at least one building block derived from a compound of general formula (I) is attached to the 3'-terminus of a nucleic acid molecule, such as 2 GalNAc compounds, such as 3 GalNac compounds, such as 4 GalNAc compounds, such as 5 GalNAc compounds attached to the 5' end of the nucleic acid molecule. In some embodiments linkage between the nucleic acid molecule and the GalNAc compound is a phosphodiester linkage. In embodiments where multiple GalNAc compounds are conjugated to the nucleic acid molecule the linkage between the first GalNac compound and the second GalNAc compound (when counted from the terminal end of the nucleic acid molecule) is a phosphodiester linkage. In a further embodiment the linkage between the first and the second and the second and the third GalNAc compound are phosphodiester linkages. In some embodiments all the linkages between the GalNAc compounds are phosphodiester linkages.

In particular, such a 5'- and/or 3'-terminally modified nucleic acid molecule comprises a compound having the general formula (IV), including any salt thereof, wherein the compound of formula (IV) is represented by:

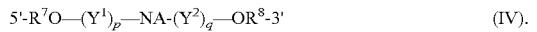

Within formula (IV), NA is a nucleic acid molecule; p and q are integers from 0 to 6; particularly from 0 to 4, provided that p+q is at least 1. This means that the nucleic acid molecule is modified with at least one mono-GalNAc conjugate moiety according to the invention. It is possible that up to 12 mono-GalNAc conjugate moieties, i.e. a maximum of 6 at either terminus, are present. Preferred numbers of mono-GalNAc containing moieties set forth below.

$R^7$ within formula (IV) is selected from H, a triphenylmethyl-based hydroxyl protecting group or 5'-hydroxyl capping group; and $R^8$ is selected from H or a 3'-hydroxyl capping group. Further, $Y^1$ is in each case independently represented by a compound of the general formula (V)

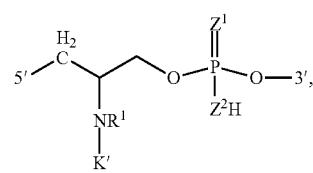

wherein $R^1$ is H or $C_{1-6}$ alkyl, K' is represented by the general formula (II')

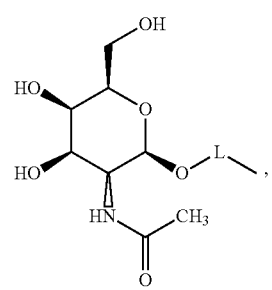

and $Z^1$ and $Z^2$ are in each case independently selected from O and S.

Still further, $Y^2$ is in each case independently represented by a compound of the general formula (VI)

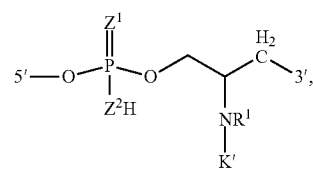

wherein $R^1$ is H or $C_{1-6}$ alkyl, K' is represented by the general formula (II')

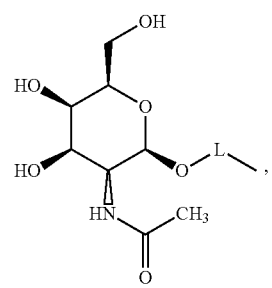

and $Z^1$ and $Z^2$ are in each case independently selected from O and S.

Independently in each appearance of formula (II'), L is a linker, particularly a linker group having a chain length of 2-30 atoms as defined above, and $Z^1$ and $Z^2$ are in each case independently selected from O and S. In certain embodiments, the linker group L in formula (II') is selected from the group consisting of —$(CH_2)_m$—C(O)—, wherein m=2-12, particularly 4, 5 or 11; —$(CH_2$—$CH_2$—$O)_n$—$CH_2$—C(O)—, wherein n=1-5, particularly 2, 3 or 4 and more particularly 3; —$(CH_2)_{m1}$—CO—NH—$(CH_2)_{m2}$—NH—C(O)—, wherein m1 and m2 each independently is 1-5, particularly 3, 4 or 5; —$(CH_2)_{m3}$—CO—NH—$(CH_2)_{m4}$—C(O)—, wherein m3 and m4 each independently is 1-5, particularly 3, 4 or 5; —$(CH_2)_{m6}$—NH—C(O)—, wherein m6 is 2-12, particularly 12; and wherein in each case C(O)— is attached to $NR^1$.

Particularly, the linker group L in formula (II') may be selected from the group consisting of —$(CH_2)_4$—C(O)—, —$(CH_2)_5$—C(O)—, —$(CH_2)_{11}$—C(O)—, —$(CH_2)_6$—NH—C(O)—, —$(CH_2)_{12}$—NH—C(O)—, —$(CH_2)_5$—CO—NH—$(CH_2)_5$—C(O)—, —$(CH_2)_4$—CO—NH—$(CH_2)_3$—NH—C(O)—, —$(CH_2)_4$—CO—NH—$(CH_2)_4$—NH—C(O)—, —$(CH_2)_5$—CO—NH—$(CH_2)_3$—NH—C(O)—, —$(CH_2)_5$—CO—NH—$(CH_2)_4$—NH—C(O)—, —$(CH_2)_6$—NH—CO—$CH_2$—NH—C(O)—, —$(CH_2CH_2O)_2$—$(CH_2)_2$—NH—C(O)—, wherein in each case C(O)— is attached to $NR^1$. According to one preferred embodiment, L is a triethyleneglycol (TEG)-acetate linker represented by the formula $(CH_2CH_2O)_3$—$CH_2$—C(O)—, wherein C(O)— is attached to $NR^1$.

In some embodiments of the nucleic acid molecule, either $Z^1$ is S and $Z^2$ is O, or both $Z^1$ and $Z^2$ are O. Where $Z^1$ and $Z^2$ appear more than once in one nucleic acid molecule, independently at each occurrence either $Z^1$ is S and $Z^2$ is O, or both $Z^1$ and $Z^2$ are O.

In certain preferred embodiments, the nucleic acid molecule is modified either at the 5'-terminus or at the 3'-terminus, i.e. in general formula (IV) either p or q is zero (0). Accordingly, q is 0 in some embodiments. In certain preferred embodiments, p is 1 and q is 0; or p is 2 and q is 0; or p is 3 and q is 0; or p is 4 and q is 0. In other embodiments, p is 0. In certain preferred embodiments, p is 0 and q is 1; or p is 0 and q is 2; or p is 0 and q is 3; or p is 0 and q is 4. In one preferred specific embodiment, p is 3 and q is 0. In another preferred specific embodiment p is 0 and q is 3.

In a further specific embodiment, a 5'-terminally modified nucleic acid molecule is represented by the following formula (VII-XY):

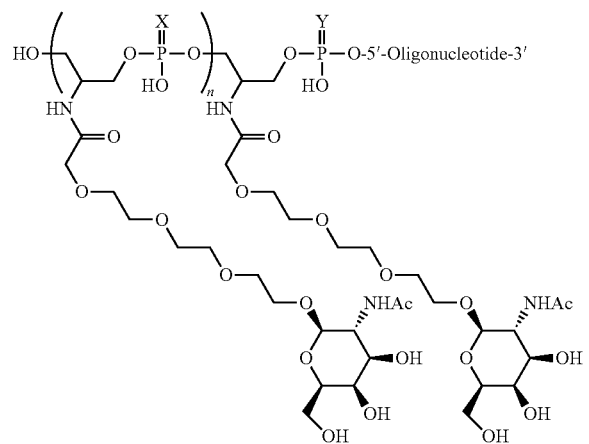

(VII-XY)

wherein n is an integer from 0 to 6, and Y and X are independently selected from S and O.

In a further specific embodiment, a 5'-terminally modified nucleic acid molecule is represented by the following formula (VII-OO):

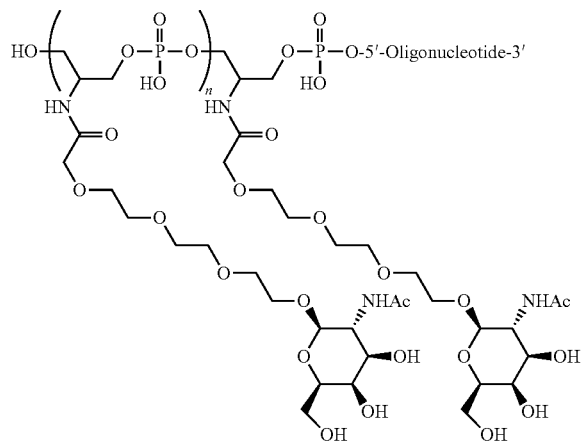

VII-OO wherein n is an integer from 0 to 6, such as from 1 to 5, such as from 2 to 4, such as 1, 2 or 3.

In a further specific embodiment, a 5'-terminally modified nucleic acid molecule is represented by the following formula (VII):

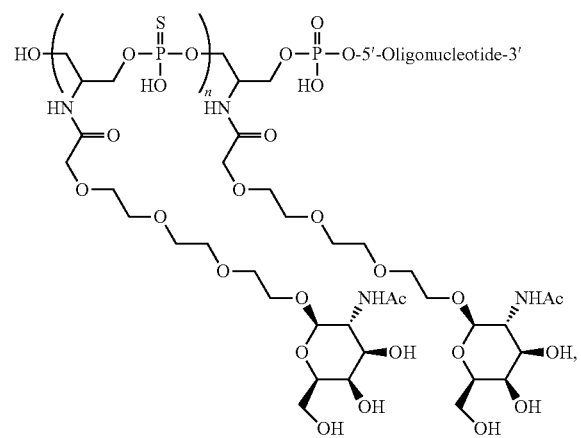

(VII)

wherein n is an integer from 0 to 6, such as from 1 to 5, such as from 2 to 4, such as 1, 2 or 3.

In a further specific embodiment, a 3'-terminally modified nucleic acid molecule is represented by the following formula (VIII-XY):

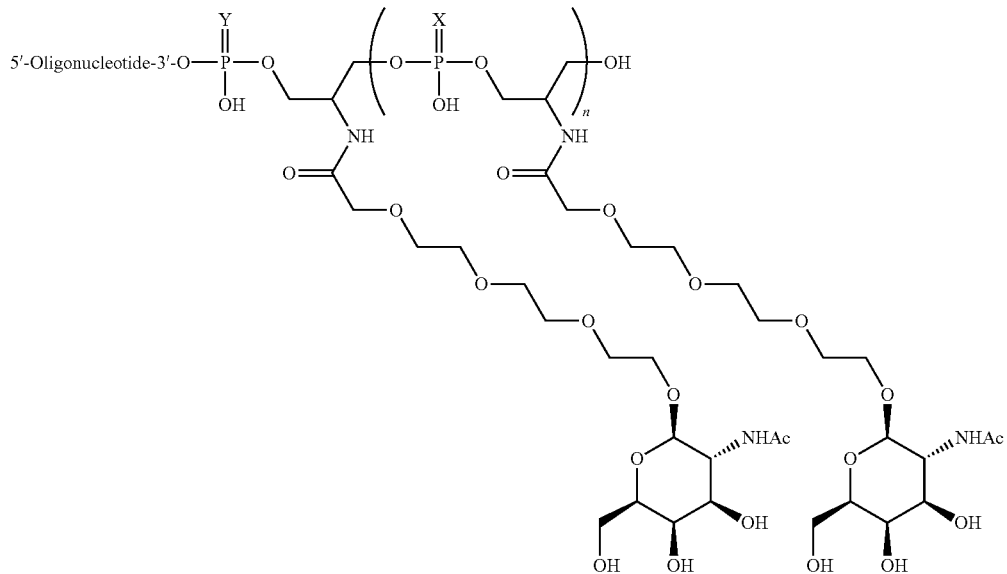
wherein n is an integer from 0 to 6, and Y and X are independently selected from S and O
In a further specific embodiment, a 3'-terminally modified nucleic acid molecule is represented by the following formula (VIII-OO):
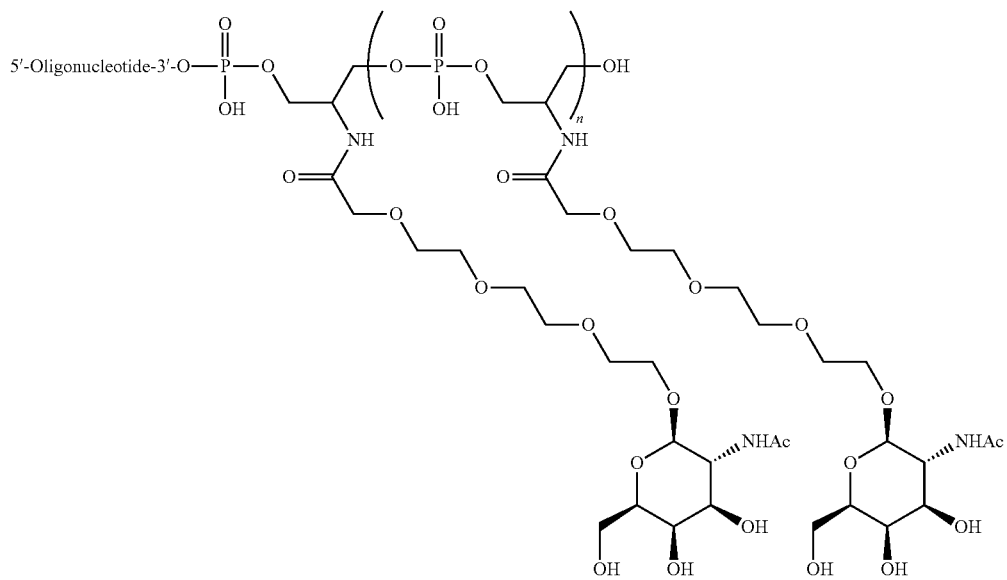
wherein n is an integer from 0 to 6, such as from 1 to 5, such as from 2 to 4, such as 1, 2 or 3

In a further specific embodiment, a 3'-terminally modified nucleic acid molecule is represented by the following formula (VIII):

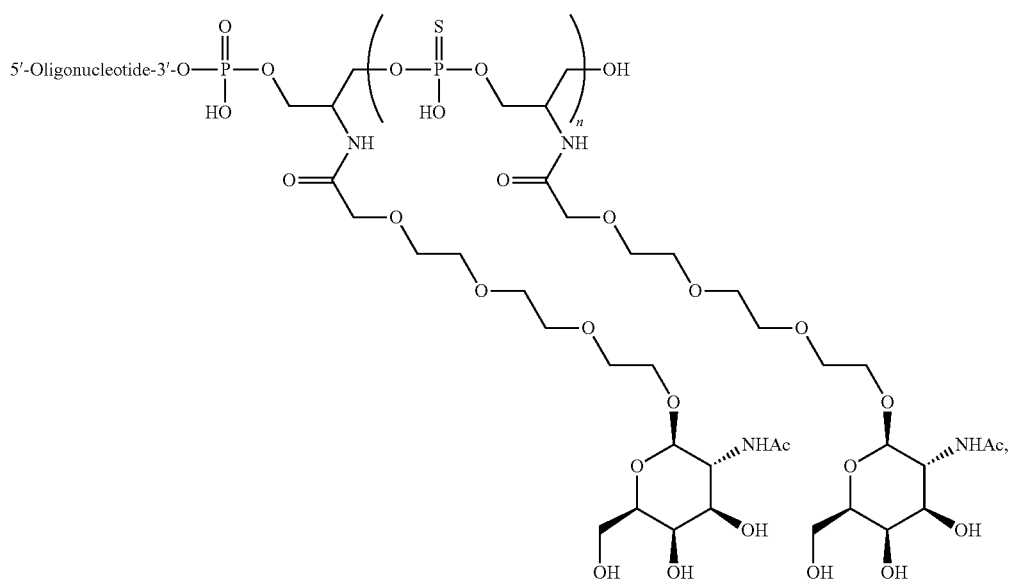

(VIII)

wherein n is an integer from 0 to 6, such as from 1 to 5, such as from 2 to 4, such as 1, 2 or 3.

The term oligonucleotide in formula (VII) and formula (VIII) is to be understood in the broad contexts of nucleic acid, particularly as described herein.

The mono-GalNAc nucleic acid conjugates according to the invention may be specifically designed for binding to the asialoglycoprotein receptor (ASGPR). Thus, according to some embodiments, a monovalent, a bivalent or, preferably, trivalent GalNAc nucleic acid conjugate according to the invention has a strong affinity for the ASGPR. In relation to the present invention "strong affinity" means an affinity characterized by an $IC_{50}$ value below 50 nM, preferably 25 nM or less, more preferably 10 nM or less, more preferably 5 nM or less.

In particularly preferred embodiments, the $IC_{50}$ for ASGPR of a monovalent GalNAc-nucleic acid conjugate is 50 nM, preferably 25 nM or less, more preferably 15 nM or less, more preferably 10 nM or less, more preferably 5 nM or less.

In particularly preferred embodiments, the $IC_{50}$ for ASGPR of a bivalent GalNAc-nucleic acid conjugate is 50 nM, preferably 25 nM or less, more preferably 15 nM or less, more preferably 10 nM or less, more preferably 5 nM or less.

In further particularly preferred embodiments, the $IC_{50}$ for ASGPR of a trivalent GalNAc-nucleic acid conjugate is 25 nM or less, preferably 15 nM or less, more preferably 10 nM or less, more preferably 5 nM or less, more preferably between 1 nM and 5 nM, e.g. about 3 nM.

The $IC_{50}$ is the concentration of GalNAc-nucleic acid conjugate that inhibits labelled ligand binding to the ASPGR by 50%. The $IC_{50}$ can be determined by the method described in Rensen et al 2001 Journal of Biological Chemistry Vol 276 pp 37577. In brief, hepatocytes (primary or in culture) are incubated with the ligand $^{125}$I-labelled asialylated orosomucoid (ASOR) at one concentration (e.g. 5 nM) for 2 h at 4° C. in the presence of increasing amounts of the GalNAc-nucleic acid conjugate to be investigated. For monovalent GalNAc-nucleic acid conjugates the concentrations could be from 2 to 200 mM; for bivalent GalNAc-nucleic acid conjugates the concentrations could be from 1 to 1000 nM; and for trivalent GalNAc-nucleic acid conjugates the concentrations could be from 0.2 to 200 nM, at increasing concentrations. The binding of the labelled ASOR is followed in the presence of the GalNAc-nucleic acid conjugate to be investigated. Nonspecific binding can be determined in the presence of 100 mM GalNAc. Displacement binding data can be analysed using a single site binding model and the $IC_{50}$ is calculated.

Preparation of Trityl-Mono-GalNAc Compounds

In a further aspect, the present invention relates to a manufacturing process of mono-GalNAc compounds. Accordingly, the invention provides a process for the preparation of a compound of formula (I), comprising the steps:

(i) reacting a compound of general formula (IX)

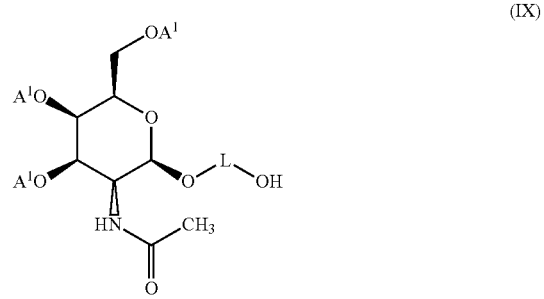

(IX)

with serinol to give a compound of general formula (X)

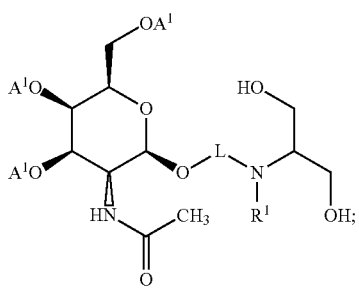

(ii) protecting one of the free hydroxyl groups of the compound of general formula (X) to give a compound of general formula (XI)

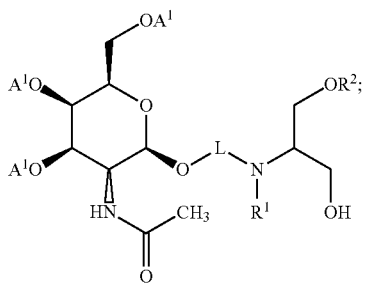

and
(iii) reacting the compound of general formula (XI) with a compound of general formula (LG)-$R^3$, wherein (LG) is a leaving group, to give a compound of general formula (XII)

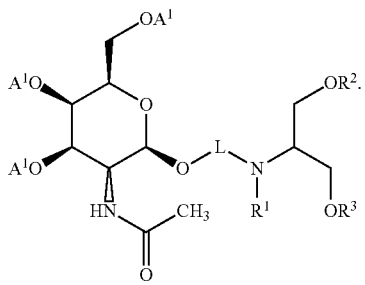

Within formulae (IX), (X), (XI), and (XII), the variables $R^1$, $R^2$, $R^3$, $A^1$ and L are as defined above with regard to general formulae (I) and (II).

As an exemplary compound of formula general formula (LG)-$R^3$, 2-cyanoethyl N,N,N',N'-tetraisopropylphosphorodiamidite (also known as bis(diisopropylamino)(2-cyanoethoxy)phosphine) may be mentioned, wherein one of the diisopropylamino groups represents the leaving group (LG), and the rest of the molecule represents $R^3$.

The Nucleic Acid Molecule

The nucleic acid molecules to be conjugated to the GalNAc conjugate moieties of the invention are capable of modulating a target nucleic acid, typically in a mammalian such as a human cell. In some embodiments, the nucleic acid molecule bind to the target nucleic acid and affect inhibition of expression of at least 10% or 20% compared to the normal expression level, more preferably at least a 30%, 40%, 50%, 60%, 70%, 80%, 90% or 95% inhibition compared to the normal expression level (such as the expression level in the absence of the nucleic acid molecule or nucleic acid molecule conjugate. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR.

The nucleic acid molecule may comprise or consist of a contiguous nucleotide sequence which corresponds to the reverse complement of the target nucleic acid. In some embodiments, the nucleic acid molecule may tolerate 1, 2, 3, or 4 mismatches, when hybridising to the target nucleic acid sequence and still sufficiently bind to the target to show the desired effect, i.e. modulation of the target nucleic acid. Mismatches may, for example, be compensated by increased length of the nucleic acid molecule and/or an increased number of modified nucleosides, such as 2' sugar modified nucleosides including LNA nucleosides, present within the nucleic acid molecule.

In some embodiments, the contiguous nucleotide sequence comprises no more than 3 mismatches, such as no more than 2 mismatches when hybridizing to the target nucleic acid, such as to the corresponding region of a nucleic acid sequence which encodes a mammalian target protein.

In some embodiments, the contiguous nucleotide sequence comprises no more than a single mismatch when hybridizing to the target nucleic acid, such as the corresponding region of a nucleic acid sequence which encodes a mammalian target protein.

The length of the nucleic acid molecule is chosen according to the desired application. In preferred embodiments, the nucleic acid molecule is between 7 and 50 nucleotides in length. In other embodiments, the length of the nucleic acid molecule is between 10 and 30, such as 11 to 22, such as from 12 to 18, such as from 13 to 17 or 14 to 16 contiguous nucleotides in length. In certain specific embodiments, the nucleic acid molecule has a length of 14, 15, 16, 17, 18, 19, or 20 nucleotides.

The nucleotide sequence of the nucleic acid molecules is preferably at least 80% identical to the reverse complement of a corresponding sequence present in the target nucleic acid, such as at least 85%, at least 90%, at least 91%, at least 92% at least 93%, at least 94%, at least 95%, at least 96% identical, at least 97% identical, at least 98% identical, at least 99% identical, such as 100% identical.

mRNA modulation can be facilitated through interaction with the RNA interference pathway machinery of the cell involving the RNAi-induced silencing complex (RISC).

In one embodiment, the RNAi nucleic acid molecule of the conjugate is assembled from two oligonucleotide fragments wherein one fragment comprises the nucleotide sequence of the antisense strand of the RNAi molecule and a second fragment comprises nucleotide sequence of the sense region of the RNAi molecule. In another embodiment, the sense strand is connected to the antisense strand via a linker molecule, such as a polynucleotide linker or a non-nucleotide linker. Preferably the conjugate of the invention is coupled to the sense strand of the RNAi molecule. If a cleavable linker is present between the RNAi and the conjugate the conjugate can be linked to either the sense or antisense strand. According to some embodiments of the invention, the claimed nucleic acid molecule is a double-stranded RNAi molecule. In particular, the modifications may be such that the GalNAc containing moiety or GalNAc containing moieties is/are attached to the sense or the antisense strand. In preferred embodiments, the GalNAc containing moiety or moieties is/are attached to the sense strand. That is, the term $R^7O$—$(Y^1)_p$ or the term $(Y^2)_q$—$OR^8$ of general formula (IV), is associated with the sense strand of the siRNA molecule.

MicroRNAs (miRNAs) are small noncoding RNA gene products about 22 nucleotides long that direct destruction or translational repression of their mRNA targets. If the complementarity between the miRNA and the target nucleic acid is partial, translation of the target nucleic acid is repressed. If complementarity is extensive, the target nucleic acid is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Blocking the seed region of the miRNA with an oligonucleotide or facilitation of the binding of the RISC/miRNA complex to the mRNA can lead to either the repression of protein translation or cleavage and degradation of the mRNA.

RNAi polynucleotide expression cassettes can be transcribed in the cell to produce small hairpin RNAs that can function as RNAi molecules, separate sense and anti-sense strand linear siRNAs, or miRNA. RNA polymerase III transcribed DNAs contain promoters selected from the list comprising: U6 promoters, HI promoters, and tRNA promoters. RNA polymerase II promoters include UI, U2, U4, and U5 promoters, snRNA promoters, microRNA promoters, and mRNA promoters.

Alternatively, RNA modulation can be facilitated by single stranded oligonucleotides complementary to the target nucleic acid (such oligonucleotides are also termed antisense oligonucleotides). It is recognised that antisense oligonucleotides may function via non RNase mediated degradation of target nucleic acids, such as by steric hindrance of translation, splice switching, or other methods, however, the preferred antisense oligonucleotides of the invention are capable of recruiting an endoribonuclease (RNase), such as RNase H. According to some preferred embodiments of the invention, the claimed nucleic acid molecule is a single-stranded antisense oligonucleotide.

In certain preferred embodiments of the present invention, the nucleic acid molecule is capable of recruiting RNase H.

To recruit RNase H, the antisense oligonucleotide, or contiguous nucleotide sequence, may be in the form of a gapmer, a headmer or a mixmer. In certain specific embodiments, the nucleic acid molecule of the invention is a gapmer.

A "headmer" is defined as an antisense oligonucleotide that comprises a region X and a region Y that is contiguous thereto, with the 5'-most monomer of region Y linked to the 3'-most monomer of region X. Region X comprises a contiguous stretch of non-RNase recruiting nucleoside analogues and region Y comprises a contiguous stretch (such as at least 7 contiguous monomers) of DNA monomers or nucleoside analogue monomers recognizable and cleavable by the RNase.

A "tailmer" is defined as an antisense oligonucleotide that comprises a region X and a region Y that is contiguous thereto, with the 5'-most monomer of region Y linked to the 3'-most monomer of the region X. Region X comprises a contiguous stretch (such as at least 7 contiguous monomers) of DNA monomers or nucleoside analogue monomers recognizable and cleavable by the RNase, and region X comprises a contiguous stretch of non-RNase recruiting nucleoside analogues.

A "mixmer" consists of an alternating composition of (i) DNA monomers or nucleoside analogue monomers recognizable and cleavable by RNase, and (ii) non-RNase recruiting nucleoside analogue monomers. Examples of mixmers can be found in WO2005/023995, hereby incorporated by reference.

A "gapmer" is defined in detail herein below.

In preferred embodiments of the invention, the claimed nucleic acid molecule comprises at least one modified nucleoside, which is/are particularly in each case independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

In certain preferred embodiments, the at least one modified nucleoside of the claimed nucleic acid molecule is a 2'-4'-bridged nucleoside.

According to some preferred embodiments of the nucleic acid molecule according to the present invention, the 2'-4'-bridged nucleoside is an LNA nucleoside, particularly a 2'-O—$CH_2$-4'-, 2'-O—$CH_2$—$CH_2$-4'-, 2'-O—$CH(CH_3)$-4'-, 2'-O—$CH(OCH_2CH_3)$-4'- or 2'-O—$C(CH_3)_2$-4'-nucleoside. In particular, the LNA nucleoside is a beta-D-oxy LNA or an alpha-L-oxy-LNA.

The internucleotide linkages in the nucleic acid molecule may be phosphodiester, phosphorothioate or boranophosphate so as to allow RNase H cleavage of targeted RNA. Phosphorothioate is preferred, for improved nuclease resistance and other reasons, such as ease of manufacture.

Accordingly, in some embodiments of the present invention, the claimed nucleic acid molecule comprises at least one modified internucleoside linkage. In particular, the nucleic acid molecule may comprise at least one modified internucleoside linkage, wherein at least one internucleoside linkage within the contiguous nucleotide sequence is a phosphorothioate internucleoside linkage.

Gapmer Design

In preferred embodiments, the nucleic acid molecule of the invention is an antisense oligonucleotide, which in turn is a gapmer.

In certain preferred embodiments of the invention, the gapmer structure of the oligonucleotide therefore comprises at least three distinct structural regions a 5'-flank, a gap and a 3'-flank, F-G-F' in '5→3' orientation. In this design, flanking regions F and F' (also termed wing regions) comprise a contiguous stretch of modified nucleosides, which are complementary to the target nucleic acid, while the gap region, G, comprises a contiguous stretch of nucleotides which are capable of recruiting a nuclease, preferably an endonuclease such as RNase, for example RNase H, when the oligonucleotide is in duplex with the target nucleic acid. Nucleosides which are capable of recruiting a nuclease, in particular RNase H, can be selected from the group consisting of DNA, alpha-L-oxy-LNA, 2'-Fluoro-ANA and UNA. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides.

Region F

Region F (5' flank or 5' wing) attached to the '5 end of region G comprises, contains or consists of at least one modified nucleoside such as at least 2, at least 3, at least 4, at least 5, at least 6, at least 7 modified nucleosides. In an embodiment region F comprises or consists of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides. The F region is defined by having at least on modified nucleoside at the 5' end and at the 3' end of the region.

In some embodiments, the modified nucleosides in region F have a 3' endo structure.

In an embodiment, one or more of the modified nucleosides in region F are 2' modified nucleosides. In one embodiment all the nucleosides in Region F are 2' modified nucleosides.

In another embodiment region F comprises DNA and/or RNA in addition to the 2' modified nucleosides. Flanks comprising DNA and/or RNA are characterized by having a 2' modified nucleoside in the 5' end and the 3'end (adjacent to the G region) of the F region. In one embodiment the region F comprise DNA nucleosides, such as from 1 to 3 contiguous DNA nucleosides, such as 1 to 3 or 1 to 2 contiguous DNA nucleosides. The DNA nucleosides in the flanks should preferably not be able to recruit RNase H. In some embodiments the 2' modified nucleosides and DNA and/or RNA nucleosides in the F region alternate with 1 to 3 2' modified nucleosides and 1 to 3 DNA and/or RNA nucleosides. Such flanks can also be termed alternating flanks. The length of the 5' flank (region F) in oligonucleotides with alternating flanks may be 4 to 10 nucleosides, such as 4 to 8, such as 4 to 6 nucleosides, such as 4, 5, 6 or 7 modified nucleosides. In some embodiments only the 5' flank of the oligonucleotide is alternating. Specific examples of region F with alternating nucleosides are

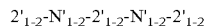

Where 2' indicates a modified nucleoside and N' is a RNA or DNA. In some embodiments all the modified nucleosides in the alternating flanks are LNA and the N' is DNA. In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F region comprises both LNA and a 2' substituted modified nucleoside. These are often termed mixed wing or mixed flank oligonucleotides.

In one embodiment of the invention all the modified nucleosides in region F are LNA nucleosides. In a further embodiment all the nucleosides in Region F are LNA nucleosides. In a further embodiment the LNA nucleosides in region F are independently selected from the group consisting of oxy-LNA, thio-LNA, amino-LNA, cET, and/or ENA, in either the beta-D or alpha-L configurations or combinations thereof. In a preferred embodiment region F comprise at least 1 beta-D-oxy LNA unit, at the 5' end of the contiguous sequence.

Region G

Region G (gap region) preferably comprises, contains or consists of at least 4, such as at least 5, such as at least 6, at least 7, at least 8, at least 9, at least 10, at least 11, at least 12, at least 13, at least 14, at least 15 or at least 16 consecutive nucleosides capable of recruiting the aforementioned nuclease, in particular RNaseH. In a further embodiment region G comprises, contains or consists of from 5 to 12, or from 6 to 10 or from 7 to 9, such as 8 consecutive nucleotide units capable of recruiting aforementioned nuclease.

The nucleoside units in region G, which are capable of recruiting nuclease are in an embodiment selected from the group consisting of DNA, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue.

In a still further embodiment at least one nucleoside unit in region G is a DNA nucleoside unit, such as from 1 to 12 DNA units, such as 2, 3, 4, 5, 6, 7, 8, 9, 10 or 11 DNA units, preferably from 2 to 12 DNA units, such as from 4 to 12 DNA units, more preferably from 5 to 11, or from 2 to 10, 4 to 10 or 6 to 10 DNA units, such as from 7 to 10 DNA units, most preferably 8, 9 or 10 DNA units. In some embodiments, region G consists of 100% DNA units.

In further embodiments the region G may consist of a mixture of DNA and other nucleosides capable of mediating RNase H cleavage. Region G may consist of at least 50% DNA, more preferably 60%, 70% or 80% DNA, and even more preferred 90% or 95% DNA.

In a still further embodiment at least one nucleoside unit in region G is an alpha-L-LNA nucleoside unit, such as at least one alpha-L-LNA, such as 2, 3, 4, 5, 6, 7, 8 or 9 alpha-L-LNA. In a further embodiment, region G comprises the least one alpha-L-LNA is alpha-L-oxy-LNA. In a further embodiment region G comprises a combination of DNA and alpha-L-LNA nucleoside units.

In some embodiments the size of the contiguous sequence in region G may be longer, such as 12, 13, 14, 15, 16, 17, 18, 19 or 20 nucleoside units.

In some embodiments, nucleosides in region G have a 2' endo structure.

In some embodiments region G may comprise a gap-breaker nucleoside, leading to a gapbreaker oligonucleotide, which is capable of recruiting RNase H.

Region F'

Region F' (3' flank or 3' wing) attached to the '3 end of region G comprises, contains or consists of at least one modified nucleoside such as at least 2, at least 3, at least 4, at least 5, at least 6, at least 7 modified nucleosides. In an embodiment region F' comprise or consist of from 1 to 7 modified nucleosides, such as from 2 to 6 modified nucleoside, such as from 2 to 4 modified nucleosides, such as from 1 to 3 modified nucleosides, such as 1, 2, 3 or 4 modified nucleosides. The F' region is defined by having at least on modified nucleoside at the 5' end and at the 3' end of the region.

In some embodiments, the modified nucleosides in region F' have a 3' endo structure.

In an embodiment, one or more of the modified nucleosides in region F' are 2' modified nucleosides. In one embodiment all the nucleosides in Region F' are 2' modified nucleosides.

In an embodiment, one or more of the modified nucleosides in region F' are 2' modified nucleosides.

In one embodiment all the nucleosides in Region F' are 2' modified nucleosides. In another embodiment region F' comprises DNA or RNA in addition to the 2' modified nucleosides. Flanks comprising DNA or RNA are characterized by having a 2' modified nucleoside in the 5' end (adjacent to the G region) and the 3'end of the F' region. In one embodiment the region F' comprises DNA nucleosides, such as from 1 to 4 contiguous DNA nucleosides, such as 1 to 3 or 1 to 2 contiguous DNA nucleosides. The DNA nucleosides in the flanks should preferably not be able to recruit RNase H. In some embodiments the 2' modified nucleosides and DNA and/or RNA nucleosides in the F' region alternate with 1 to 3 2' modified nucleosides and 1 to 3 DNA and/or RNA nucleosides, such flanks can also be termed alternating flanks. The length of the 3' flank (region F') in oligonucleotides with alternating flanks may be 4 to 10 nucleosides, such as 4 to 8, such as 4 to 6 nucleosides, such as 4, 5, 6 or 7 modified nucleosides. In some embodiments only the 3' flank of the oligonucleotide is alternating. Specific examples of region F' with alternating nucleosides are

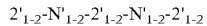

Where 2' indicates a modified nucleoside and N' is a RNA or DNA. In some embodiments all the modified nucleosides in the alternating flanks are LNA and the N' is DNA. In a further embodiment modified nucleosides in region F' are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F' region comprises both LNA and a 2' substituted modified nucleoside. These are often termed mixed wing or mixed flank oligonucleotides.

In one embodiment of the invention all the modified nucleosides in region F' are LNA nucleosides. In a further embodiment all the nucleosides in Region F' are LNA nucleosides. In a further embodiment the LNA nucleosides in region F' are independently selected from the group consisting of oxy-LNA, thio-LNA, amino-LNA, cET and/or ENA, in either the beta-D or alpha-L configurations or combinations thereof. In a preferred embodiment region F' has at least 2 beta-D-oxy LNA unit, at the 3' end of the contiguous sequence.

Region D' and D"

Region D' and D" can be attached to the 5' end of region F or the 3' end of region F', respectively.

Region D' or D" may independently comprise 1, 2, 3, 4 or 5 additional nucleotides, which may be complementary or non-complementary to the target nucleic acid. In this respect the oligonucleotide of the invention, may in some embodiments comprise a contiguous nucleotide sequence capable of modulating the target which is flanked at the 5' and/or 3' end by additional nucleotides. Such additional nucleotides may serve as a nuclease susceptible biocleavable linker.

In some embodiments the additional 5' and/or 3' end nucleotides are linked with phosphodiester linkages, and may be DNA or RNA. In another embodiment, the additional 5' and/or 3' end nucleotides are modified nucleotides which may for example be included to enhance nuclease stability or for ease of synthesis. In an embodiment of the oligonucleotide of the invention, comprises a region D' and/or D" in addition to the contiguous nucleotide sequence.

In some embodiments region D' or D" comprises a dinucleotide of sequence AA, AT, AC, AG, TA, TT, TC, TG, CA, CT, CC, CG, GA, GT, GC, or GG, wherein C may be 5-methylcytosine (also referred to as $^mC$), and/or T may be replaced with U.

The gapmer oligonucleotide of the present invention can be represented by the following formulae:

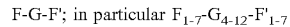

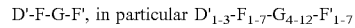

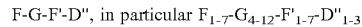

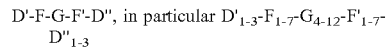

The preferred number and types of nucleosides in regions F, G and F', D' and D" have been described above.

In certain preferred embodiments of the invention, the nucleic acid molecule is a gapmer of formula 5'-F-G-F'-3', where regions F and F' in each case independently comprise 1 to 7 modified nucleosides and G is a region between 6 and 16 nucleosides which are capable of recruiting RNase H.

The oligonucleotide conjugates of the present invention may have a region C covalently attached to either the 5' or 3' end of the oligonucleotide, in particular the gapmer oligonucleotides presented above.

In one embodiment the oligonucleotide conjugate of the invention comprises a oligonucleotide with the formula 5'-D'-F-G-F'-3' or 5'-F-G-F'-D"-3', where region F and F' independently comprise 1-7 modified nucleosides, G is a region between 6 and 16 nucleosides which are capable of recruiting RNaseH and region D' or D" comprise 1-5 phosphodiester linked nucleosides. Preferably region D' or D" is present in the end of the oligonucleotide where conjugation to a conjugate moiety is contemplated.

Examples of oligonucleotides with alternating flanks can be represented by the following formulae:

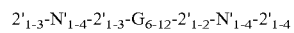

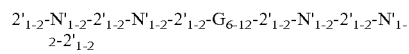

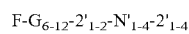

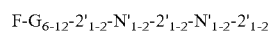

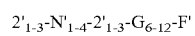

Where a flank is indicated by F or F' it only contains 2' modified nucleosides, such as LNA nucleosides and wherein 2' indicates a modified nucleoside and N' is an RNA or DNA. The preferred number and types of nucleosides in the alternating regions, and region F, G and F', D' and D" have been described above.

In some embodiments the oligonucleotide is a gapmer consisting of 10, 11, 12, 13, 14, 15 or 16 nucleotides in length, wherein each of regions F and F' independently consists of 1, 2, 3 or 4 modified nucleoside units complementary to the target nucleic acid and region G consists of 7, 8, 9, or 10 nucleoside units, capable of recruiting nuclease when in duplex with the target nucleic acid.

In a further embodiments, the oligonucleotide is a gapmer wherein each of regions F and F' independently consists of 3, 4, 5 or 6 modified nucleoside units, such as nucleoside units containing a 2'-O-methoxyethyl-ribose sugar (2'-MOE) or nucleoside units containing a 2'-fluoro-deoxyribose sugar and/or LNA units, and region G consists of 8, 9, 10, 11 or 12 nucleoside units, such as DNA units or other nuclease recruiting nucleosides such as alpha-L-LNA or a mixture of DNA and nuclease recruiting nucleosides.

In a further specific embodiment, the oligonucleotide is a gapmer wherein each of regions F and F' region consists of two LNA units each, and region G consists of 8, 9 or 10 nucleoside units, preferably DNA units. Specific gapmer designs of this nature include 2-8-2, 2-9-2 and 2-10-2.

In a further specific embodiment, the oligonucleotide is a gapmer wherein each of regions F and F' independently consists of three LNA units, and region G consists of 8, 9 or 10 nucleoside units, preferably DNA units. Specific gapmer designs of this nature include 3-8-3, 3-9-3 and 3-10-3.

In a further specific embodiment, the oligonucleotide is a gapmer wherein each of regions F and F' consists of four LNA units each, and region G consists of 8 or 9 or 10 nucleoside units, preferably DNA units. Specific gapmer designs of this nature include 4-8-4, 4-9-4 and 4-10-4

Specific gapmer designs of this nature include F-G-F' designs selected from a group consisting of a gap with 6 nucleosides and independently 1 to 4 modified nucleosides in the wings including 1-6-1, 1-6-2, 2-6-1, 1-6-3, 3-6-1, 1-6-4, 4-6-1, 2-6-2, 2-6-3, 3-6-2 2-6-4, 4-6-2, 3-6-3, 3-6-4 and 4-6-3 gapmers.

Specific gapmer designs of this nature include F-G-F' designs selected from a group consisting of a gap with 7 nucleosides and independently 1 to 4 modified nucleosides in the wings including 1-7-1, 2-7-1, 1-7-2, 1-7-3, 3-7-1, 1-7-4, 4-7-1, 2-7-2, 2-7-3, 3-7-2, 2-7-4, 4-7-2, 3-7-3, 3-7-4, 4-7-3 and 4-7-4 gapmers.

Specific gapmer designs of this nature include F-G-F' designs selected from a group consisting of a gap with 8 nucleosides and independently 1 to 4 modified nucleosides in the wings including 1-8-1, 1-8-2, 1-8-3, 3-8-1, 1-8-4, 4-8-1, 2-8-1, 2-8-2, 2-8-3, 3-8-2, 2-8-4, 4-8-2, 3-8-3, 3-8-4, 4-8-3, and 4-8-4 gapmers.

Specific gapmer designs of this nature include F-G-F' designs selected from a group consisting of a gap with 9 nucleosides and independently 1 to 4 modified nucleosides in the wings including, 1-9-1, 2-9-1, 1-9-2, 1-9-3, 3-9-1, 1-9-4, 4-9-1, 2-9-2, 2-9-3, 3-9-2, 2-9-4, 4- 9-2, 3-9-3, 3-9-4, 4-9-3 and 4-9-4 gapmers.

Specific gapmer designs of this nature include F-G-F' designs selected from a group consisting of a gap with 10 nucleosides including, 1-10-1, 2-10-1, 1-10-2, 1-10-3, 3-10-1, 1-10-4, 4-10-1, 2-10-2, 2-10-3, 3-10-2, 2-10-4, 4-10-2, 3-10-3, 3-10-4, 4-10-3 and 4-10-4 gapmers.

In all instances the F-G-F' design may further include region D' and/or D", which may have 1, 2 or 3 nucleoside units, such as DNA units. Preferably, the nucleosides in region F and F' are modified nucleosides, while nucleotides in region G are preferably unmodified nucleosides.

In each design, the preferred modified nucleoside is LNA.

In another embodiment all the internucleoside linkages in the gap in a gapmer are phosphorothioate and/or boranophosphate linkages. In another embodiment all the internucleoside linkages in the flanks (F and F' region) in a gapmer are phosphorothioate and/or boranophosphate linkages. In another preferred embodiment all the internucleoside linkages in the D' and D" region in a gapmer are phosphodiester linkages.

For specific gapmers as disclosed herein, when the cytosine (C) residues are annotated as 5-methyl-cytosine, in various embodiments, one or more of the Cs present in the oligonucleotide may be unmodified C residues.

In a particular embodiment, the gapmer is a so-called shortmer as described in WO2008/113832 incorporated herein by reference.

Further gapmer designs are disclosed in WO2004/046160, WO2007/146511 and incorporated by reference.

An exemplary nucleic acid molecule that can be incorporated into the conjugates according to the invention is 5'-G'''CattggtatT'''CA-3'(SEQ ID NO: 1) capital letters represent LNA nucleosides; all LNA C are 5'methyl C; lower case letters represent DNA nucleosides; the internucleoside linkages are phosphorothioate linkages.

A further exemplary nucleic acid molecule that can be incorporated into the conjugates according to the invention is 5'-caG'''CattggtatT'''CA-3' (SEQ ID NO: 2) capital letters represent LNA nucleosides; all LNA C are 5'methyl C; lower case letters represent DNA nucleosides; the two first internucleoside linkages from the 5' end are phospodiester linkages, the remaining internucleoside linkages are phosphorothioate linkages.

The Target

The nucleic acid conjugates of the invention can be used for modulating a nucleic acid target.

In some embodiments, the nucleic acid molecule modulates a liver-expressed RNA, such as a liver-expressed mRNA or microRNA. In particular mRNA or microRNA expressed in hepatocytes. In some embodiments, the nucleic acid molecule modulates a target nucleic acid selected from the table 1 below. The nucleic acid conjugates of the present invention may be used in a medicine to treat one or more diseases selected from the table 1 below.

TABLE 1

| liver targets and associated diseases | | |
|---|---|---|
| Target nucleic acids (mRNA encoding, or miRNA) | Target sequence | Disease or disorders |
| 5'UTR | | HCV |
| 5'UTR & NS5B | | HCV |
| Alpha-1 antitrypsin (AAT) | M11465.1 GI: 177826 | A1ATD associated pulmonary disease |

TABLE 1-continued liver targets and associated diseases

| Target nucleic acids (mRNA encoding, or miRNA) | Target sequence | Disease or disorders |
|---|---|---|
| ALAS1 | BC011798.2 GI: 33877783; AK312566.1 GI: 164690365; NM_199166.2 GI: 362999012; NM_000688.5 GI: 362999011 | Porphyria |
| ALDH2 | | Alcohol dependence |
| ANGPLT3 | NCBI BC007059.1 GI: 14712025 BC058287.1 GI: 34849466 | Hyperlipidaemia, atherosclerosis, coronary heart disease or insulin resistance |
| Antithrombin III | | Hemophilia A, B Rare Bleeding disorders |
| Apo(a) | NM_005577.2 GI:116292749 | cardiovascular disease, coronary heart disease, Atherosclerosis/high Lp(a) |
| ApoB-100 | NM 000384.1 | Hypercholesterolemia, hyperlipidaemia, acute coronary syndrome |
| ApoCIII | BC027977.1 GI:20379764 | Hypertriglyceridemia, atherosclerosis and metabolic syndrome |
| Bcl2 | M13994.1 GI:179366 | |
| Complement component C5 | M57729.1 GI: 179982 | paroxysmal nocturnal hemoglobinuria (PNH), atypical hemolytic-uremic syndrome (aHUS), myasthenia gravis, and neuromyelitis optica |
| CRP | NM 000567.1 | Inflammatory disorders |
| DGAT2 | NM 032564.2 | Nonalcoholic Steatohepatitis (NASH), type 2 diabetes and insulin resistance |
| Factor C6 | BC035723.1 J05024.1 GI:187824 J05064.1 GI:179703 | Infectious diseases |
| Factor IXa | | Thrombosis |
| Factor VII | NM 000131.3 NM 019616.2 ID 2155, NCBI J02933.1 GI:180333 | Thrombosis |
| Factor XI | BC122863.1 GI:114108211 | Thrombosis, arthritis and colitis |
| FGFR4 | NCBI Gene 2264 - NC_000005.9 (176513906 ... 176525143 | Obesity, insulin resistance, hyperglycemia, diabetes type 1 or 2 |
| GCCR | NM 000160.1 | Cushing's Syndrome |
| GCGR | BC112041.1 GI: 85567507; L20316.1 GI: 405189 | Insulin resistance, hyperglycemia, diabetes type 1 or 2, preservation of pancreatic function, and control of blood glucose levels |
| Growth hormone receptor | | Acromegaly |
| HAMP pathway | | Anemia or inflammation/CKD |
| Hepatitus B (HBV) | NCBI D23684.1 GI:560092; D23683.1 GI: 560087; D23682.1 GI: 560082; D23681.1 GI: 560077; D23680.1 GI: 560072; D23679.1 GI: 560067; D23678.1 GI: 560062; D23677.1 GI: 560057 | HBV infection |
| Hepatic Glucose 6-Phosphate Transporter-1 | | glucose homeostasis, diabetes, type 2 diabetes |
| KSP or VEGF | | Liver cancer |
| miR-122 | | HCV, high cholesterol |
| miR-21 | | Liver cancer |
| miR-33 | | Metabolic syndrome, Atherosclerosis |
| miR-34 | | Liver cancer |
| miR-378 | | Cardiometabolic diseases |
| miR-7 | | Liver cancer |

TABLE 1-continued liver targets and associated diseases

| Target nucleic acids (mRNA encoding, or miRNA) | Target sequence | Disease or disorders |
| --- | --- | --- |
| mtGPAT | ID 57678 | obesity, fatty liver, hepatosteatosis, non alcoholic fatty liver disease (NAFLD), non alcoholic steatohepatitis (NASH), insulin resistance, diabetes such as non insulin dependent diabetes mellitus (NIDDM). |
| MTP | | Hyperlipidaemia |
| Myc | | Liver cancer |
| NS3 | | HCV |
| PCSK9 | NM 174936.2 | Hypercholesterolemia, atherosclerosis, hyperlipidaemia, familiar hypercholesterolemia |
| PLK1 | | Liver cancer |
| PTP-1B | NM 002827.2 | Type 2 diabetes |
| Serum amyloid A | | SAA-amyloidosis |
| SGLT2 | NM 003041.1 | Hyperglycaemia, Type 2 diabetes |
| TMPRSS6 | | Hemochromatosis |
| TTR | BC020791.1 GI:18089144, BC005310.1 GI:13529049 | TTR amyloidosis |
| VEGF | GENE ID 7422, human Sequence: Chromosome: 6; NC_000006.11 (43737946 . . . 43754224 | hyperproliferative disorders, such as liver cancer |

Compositions

The nucleic acid conjugates of the invention may be used in pharmaceutical formulations and compositions. Suitably, such compositions comprise a pharmaceutically acceptable diluent, solvent, carrier, salt and/or adjuvant. Accordingly, in some embodiments of the invention, such a pharmaceutical composition comprises a nucleic acid molecule as described herein and a pharmaceutically acceptable diluent, solvent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 µM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO2007/031091 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in WO2007/031091-which are also hereby incorporated by reference.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the nucleic acid conjugate of the invention is a prodrug. In particular with respect to nucleic acid conjugates with a biocleavable linker where the conjugate moiety is cleaved of the nucleic acid molecule once the prodrug is delivered to the site of action, e.g. the target cell.

Applications

The compounds of the invention may be utilized as research reagents for, for example, diagnostics, therapeutics and prophylaxis.

In particular, nucleic acid molecules or pharmaceutical composition as claimed herein are for use in medicine, particularly in human medicine. The medicine may be used for the treatment of any of the diseases listed in table 1.

The invention provides a method of modulating, e.g. down-regulating or inhibiting the expression or functionality of a protein and/or mRNA and/or microRNA and/or long non-coding RNA in a target cell comprising administering the nucleic acid conjugate according to the invention to said cell to down-regulate or inhibit the expression or functionality of a target protein and/or mRNA and/or microRNA and/or long non-coding RNA in said cell. Suitably the cell is a mammalian cell such as a human cell and preferably it is a liver cell. The administration may occur, in some embodiments, in vitro. The administration may occur, in some embodiments, in vivo. The administration of the composition is in an amount sufficient to be effective in treating or preventing a disorder or to regulate a physiological condition in humans.

Further provided are methods of treating a mammal, such as treating a human, suspected of having or being prone to a disease or condition, by administering a therapeutically or prophylactically effective amount of one or more of the nucleic acid conjugates of the invention.

The nucleic acid conjugate or a pharmaceutical composition according to the invention is typically administered in an effective amount.

In particular compounds of formula (IV) may be used in the applications of the invention.

The invention also provides for the use of the nucleic acid conjugate of the invention as described for the manufacture of a medicament for the treatment of a disorder or for a method of the treatment of as a disorder affected by the modulation of a target nucleic acid.

The invention also provides for a method for treating a disorder, said method comprising administering a compound according to the invention and/or a pharmaceutical composition according to the invention to a patient in need thereof.

Examples of disorders to be treated are liver diseases such as those listed in table 1.

In one embodiment the nucleic acid conjugates of the present invention are used in the manufacture of a medicament for the treatment of infectious diseases in the liver, such as a viral liver infection, such as HBV or HCV.

In one embodiment the nucleic acid conjugates of the present invention are used in the manufacture of a medicament for the treatment of a metabolic disorder such as, hypercholesterolemia, familiar hypercholesterolemia, hyperlipidaemia, hypertriglyceridemia, hyperglycemia, glucose homeostasis, cardiovascular disease, cardiometabolic disease, atherosclerosis, acute coronary syndrome, coronary heart disease, obesity, metabolic syndrome, insulin resistance, nonalcoholic steatohepatitis (NASH), non-alcoholic fatty liver disease (NAFLD), non-insulin dependent diabetes mellitus (NIDDM). type 2 diabetes, type 1 diabetes, Porphyria.

In one embodiment the nucleic acid conjugates of the present invention are used in the manufacture of a medicament for the treatment of proliferative diseases such as liver cancer.

In one embodiment the nucleic acid conjugates of the present invention are used in the manufacture of a medicament for the treatment of disorders relating to the blood or complement system, such as thrombosis, hemophilia A, B rare, anemia, paroxysmal nocturnal hemoglobinuria (PNH), atypical hemolytic-uremic syndrome (aHUS), and hemochromatosis.

In one embodiment the nucleic acid conjugates of the present invention are used in the manufacture of a medicament for the treatment of inflammatory disorders such as arthritis and colitis.

EMBODIMENTS

The following embodiments of the present invention may be used in combination with any other embodiments described herein.

1. A compound having the general formula (I) including any salt thereof, wherein the compound is represented by:

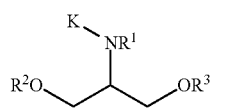

(I)

wherein $R^1$ is H or $C_{1-6}$ alkyl;

a. $R^2$ is a triphenylmethyl-based hydroxyl protecting group
b. $R^3$ is a phosphorus-containing group, particularly a phosphoramidite or a phosphonoamidite group, and
K is represented by the general formula (II)

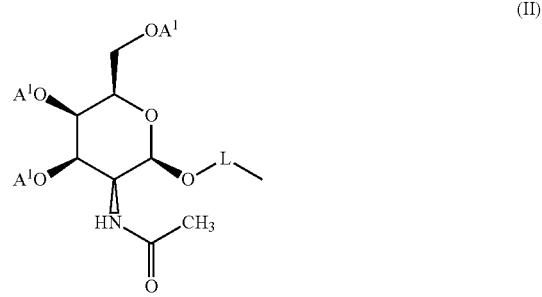

(II)

wherein $A^1$ is a hydroxyl protecting group, which may be the same or different at each occurrence and L is a linker.

2. The compound of embodiment 1, wherein $R^1$ is H.
3. The compound of embodiment 1 or 2, wherein $R^2$ is triphenylmethyl, methoxytrityl or dimethoxytrityl, particularly dimethoxytrityl.
4. The compound of any one of embodiments 1-3, wherein $R^3$ is represented by the general formula (III):

(III)

wherein $R^4$ and $R^5$ are independently selected from $C_{1-6}$ alkyl or $R^4$ and $R^5$ together from a five- or six-membered ring, which may be substituted and which may contain one further heteroatom selected from N and O;
X is O or S
n is 0 or 1, and
$R^6$ is $C_{1-8}$ alkyl optionally substituted with thio, oxo, halo and/or CN.

5. The compound of embodiment 4, wherein $NR^4R^5$ is selected from dimethylamino, diethylamino, di-n-propylamino, diisopropylamino, dibutylamino, pyrrolidino, piperidino, 2,6-dimethylpiperidino, morpholino, imidazolyl, and 4-methylimidazolyl, and/or wherein $XR^6$ is selected from methyl, ethyl, 2-cyanoethyloxy, 2-cyanoethylthio, methoxy, ethoxy, S-isobutanoyl-2-(2-mercaptoethoxy)ethoxy, S-pivaloyl-2-(2-mercaptoethoxy)ethoxy, and S-pivaloyl-2-mercaptoethoxy.

6. The compound of embodiment 4 or 5, wherein $NR^4R^5$ is diisopropylamino, and/or $XR^6$ is 2-cyanoethoxy.

7. The compound of any one of embodiments 1-6, wherein $A^1$ is selected from an acyl group and a silyl group, preferably from acetyl, benzoyl, phenoxy-acetyl, pivaloyl, isobutyryl, t-butyldimethylsilyl, t-butyldiphenylsilyl, triisopropylsilyl and isopropyldimethylsilyl.

8. The compound of any one of embodiments 1-7, wherein $A^1$ is acetyl.

9. The compound of any one of embodiments 1-8, wherein L is a linker group having a chain length of 2-30 atoms.

10. The compound of any one of embodiments 1-9, wherein L is selected from the group consisting of —(CH$_2$)$_m$—C(O)—, wherein m=2-12, particularly 4, 5 or 11;

—(CH$_2$—CH$_2$—O)$_n$—CH$_2$—C(O)—, wherein n=1-5, particularly 2, 3 or 4 and more particularly 3;

—(CH$_2$)$_{m1}$—CO—NH—(CH$_2$)$_{m2}$—NH—C(O)—, wherein m1 and m2 each independently is 1-5, particularly 3, 4 or 5;

—(CH$_2$)$_{m3}$—CO—NH—(CH$_2$)$_{m4}$—C(O)—, wherein m3 and m4 each independently is 1-5, particularly 3, 4 or 5; and —(CH$_2$)$_{m6}$—NH—C(O)—, wherein m6 is 2-12, particularly 12;

and wherein in each case C(O)— is attached to NR$^1$.

11. The compound of any one of embodiments 1-10, wherein the compound is represented by formula (XV)

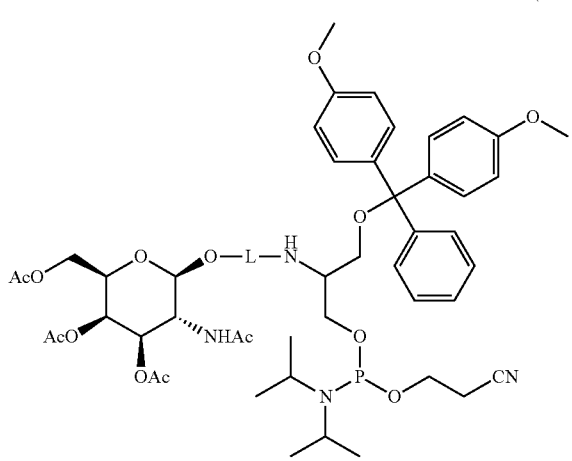

(XVI)

12. The compound of any one of embodiments 1-11, wherein L is selected from the group consisting of —(CH$_2$)$_4$—C(O)—, —(CH$_2$)$_5$—C(O)—, —(CH$_2$)$_{11}$—C(O)—, —(CH$_2$)$_6$—NH—C(O)—, —(CH$_2$)$_{12}$—NH—C(O)—, —(CH$_2$)$_5$—CO—NH—(CH$_2$)$_5$—C(O)—, —(CH$_2$)$_4$—CO—NH—(CH$_2$)$_3$—NH—C(O)—, —(CH$_2$)$_4$—CO—NH—(CH$_2$)$_4$—NH—C(O)—, —(CH$_2$)$_5$—CO—NH—(CH$_2$)$_3$—NH—C(O)—, —(CH$_2$)$_5$—CO—NH—(CH$_2$)$_4$—NH—C(O)—, —(CH$_2$)$_6$—NH—CO—CH$_2$—NH—C(O)—, and —(CH$_2$CH$_2$O)$_2$—(CH$_2$)$_2$—NH—C(O)—, and wherein in each case C(O)— is attached to NR$^1$ or NH.

13. The compound of any one of embodiments 1-12, wherein the compound is represented by formula (XV)

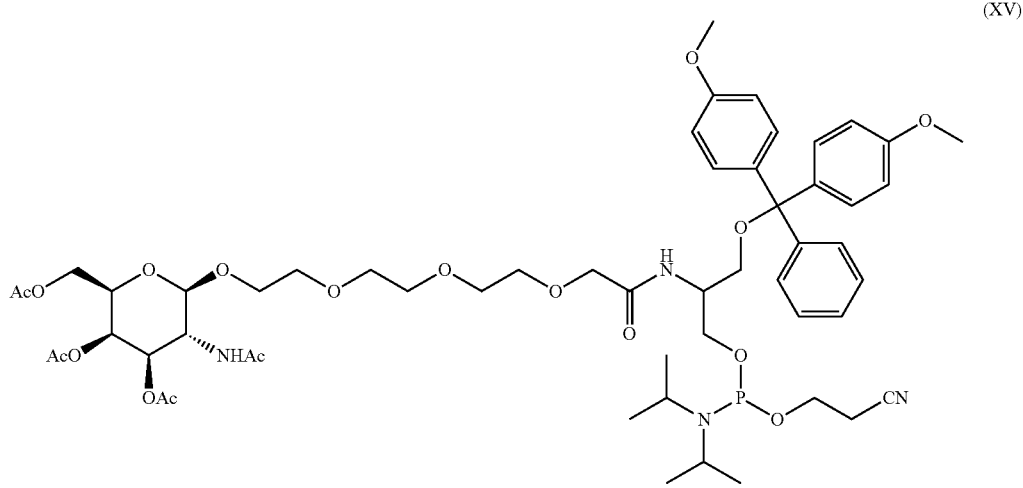 [SMILES: COc1ccc(C(OCC(COP(OCCC#N)N(C(C)C)C(C)C)NC(=O)COCCOCCOCCO[C@@H]2O[C@H](COC(C)=O)[C@H](OC(C)=O)[C@H](OC(C)=O)[C@H]2NC(C)=O)(c2ccccc2)c2ccc(OC)cc2)cc1]

(XV)

14. Use of a compound of the general formula (I) according to any one of embodiments 1-13 as a building block for incorporation into a biomolecule.

15. The use according to embodiment 14, wherein the compound increases the effect of the biomolecule in the liver, in particular in the hepatocytes when compared to the biomolecule without the compound.

16. The use according to embodiment 14 or 15, wherein the biomolecule is a nucleic acid molecule.

17. A nucleic acid molecule having attached to the 5'-terminus and/or the 3'-terminus thereof at least one building block derived from a compound of general formula (I) as defined in any one embodiments 1-13.

18. A 5'- and/or 3'-terminally modified nucleic acid molecule comprising a compound having the general formula (IV), including any salt thereof, wherein compound (IV) is represented by:

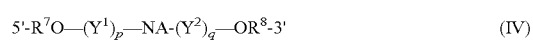

5'-R$^7$O—(Y$^1$)$_p$—NA-(Y$^2$)$_q$—OR$^8$-3'      (IV)

wherein NA is a nucleic acid molecule p and q are integers from 0 to 6, particularly from 0 to 4, provided that p+q is at least 1, R$^7$ is selected from H, a triphenylmethyl-based hydroxyl protecting group or 5'-hydroxyl capping group, R$^8$ is selected from H or a 3'-hydroxyl capping group, Y$^1$ is in each case independently represented by a compound of the general formula (V)

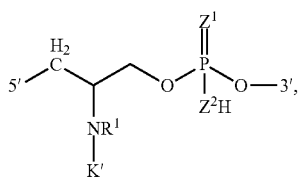

$Y^2$ is in each case independently represented by a compound of the general formula (VI)

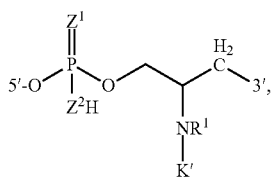

wherein for each $Y^1$ and $Y^2$ independently
$R^1$ is H or $C_{1-6}$ alkyl;
K' is represented by the general formula (II')

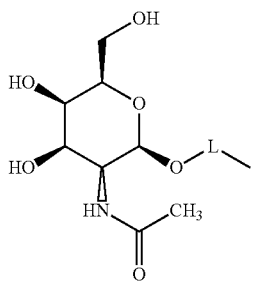

wherein L is a linker and $Z^1$ and $Z^2$ are in each case independently selected from O and S.

19. The nucleic acid molecule of embodiment 18, wherein the linker is a linker group having a chain length of 2-30 atoms, particularly a linker as defined in embodiment 10 or embodiment 11.

20. The nucleic acid molecule of embodiment 18 or 19, wherein in each case independently $Z^1$ is S and $Z^2$ is O, or $Z^1$ and $Z^2$ are O.

21. The nucleic acid molecule of any one of embodiments 18-20, wherein
    i) p is 1 and q is 0,
    ii) p is 2 and q is 0,
    iii) p is 3 and q is 0,
    iv) p is 4 and q is 0,
    v) p is 0 and q is 1,
    vi) p is 0 and q is 2,
    vii) p is 0 and q is 3, or
    viii) p is 0 and q is 4.

22. The nucleic acid molecule of any one of embodiments 18-21, wherein p is 3 and q is 0, or wherein p is 0 and q is 3.

23. The nucleic acid molecule of embodiments 21 or 22, wherein $Z^1$ and $Z^2$ are O for the $Y^1$ and/or $Y^2$ moieties adjacent to the NA, where $Z^1$, $Z^2$, $Y^1$, and $Y^2$ are defined according to embodiment 18.

24. The nucleic acid molecule of any of the embodiments 21 to 23, wherein $Z^1$ and $Z^2$ are O for the $Y^1$ and/or $Y^2$ moieties adjacent to the first $Y^1$ and/or $Y^2$ moiety.

25. The nucleic acid molecule of any of the embodiments 23 or 24, wherein herein $Z^1$ and $Z^2$ are S for the reminder of the $Y^1$ and/or $Y^2$ moieties.

26. The nucleic acid molecule of embodiments 21 or 22, wherein $Z^1$ and $Z^2$ are O for all the $Y^1$ and/or $Y^2$ moieties, where $Z^1$, $Z^2$, $Y^1$, and $Y^2$ are defined according to embodiment 18.

27. The nucleic acid molecule of any one of embodiments 18-21, wherein the molecule is represented by formula (VII-XY) or formula (VIII-XY)

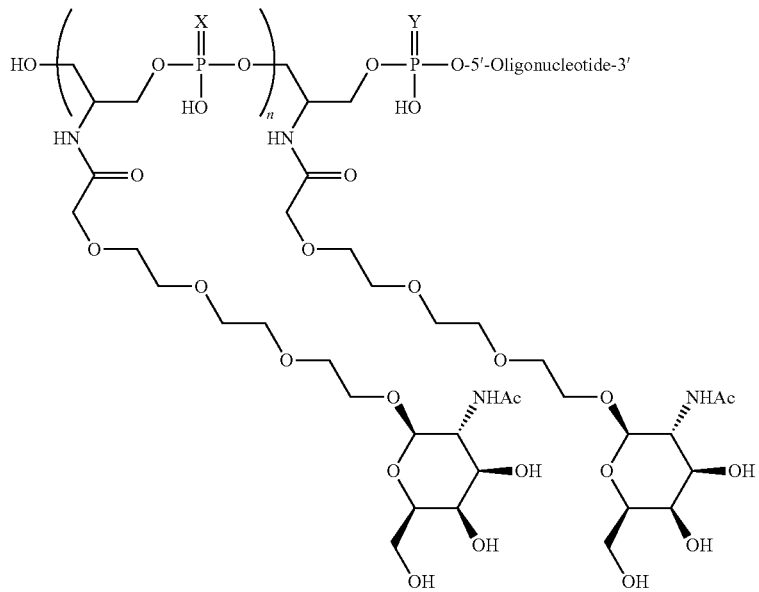

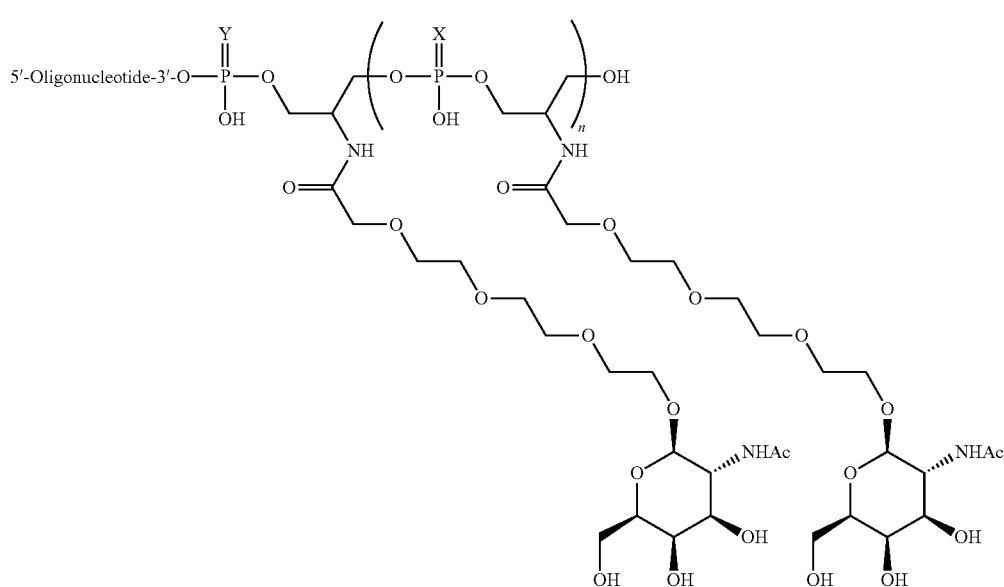

where n is an integer from 0 to 6, and Y and X are independently selected from S and O.

28. The nucleic acid molecule of any one of embodiments 18-21, wherein the molecule is represented by formula (VII) and n is an integer from 0 to 6

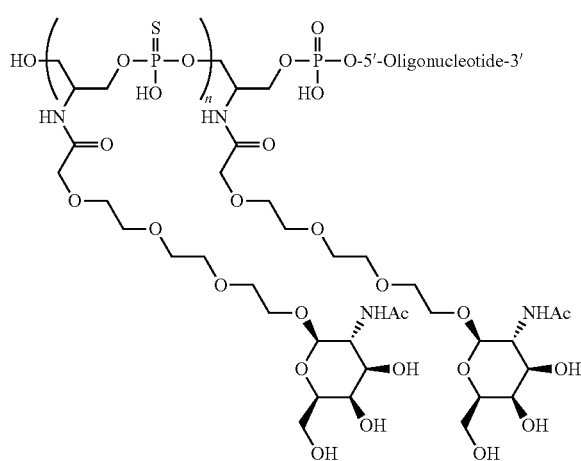

29. The nucleic acid molecule of any one of embodiments 18-21, wherein the molecule is represented by formula (VII-OO) and n is an integer from 0 to 6

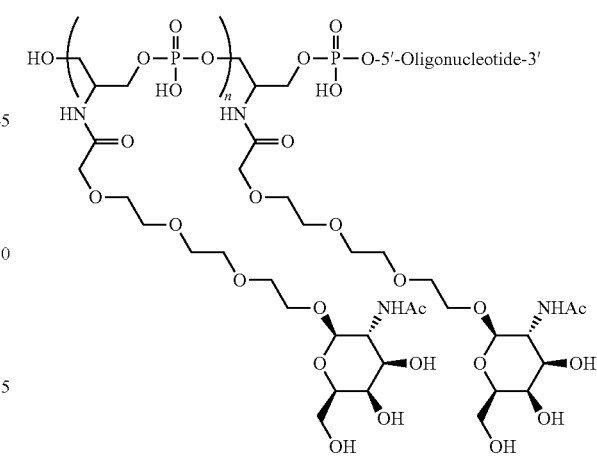

30. The nucleic acid molecule of any one of embodiments 18-21, wherein the molecule is represented by formula (VIII) and n is an integer from 0 to 6

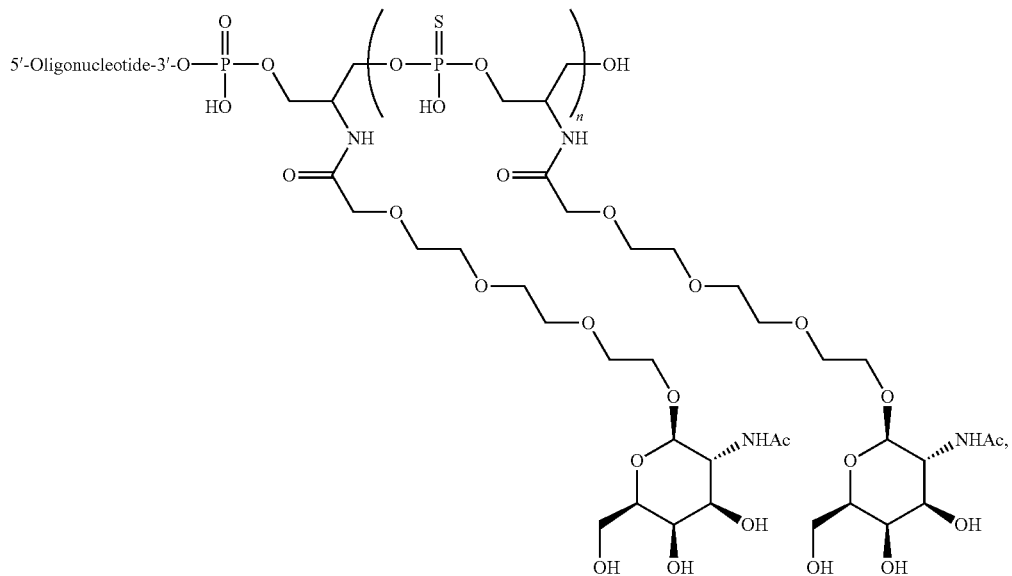

(VIII)

31. The nucleic acid molecule of any one of embodiments 18-21, wherein the molecule is represented by formula (VIII-OO) and n is an integer from 0 to 6

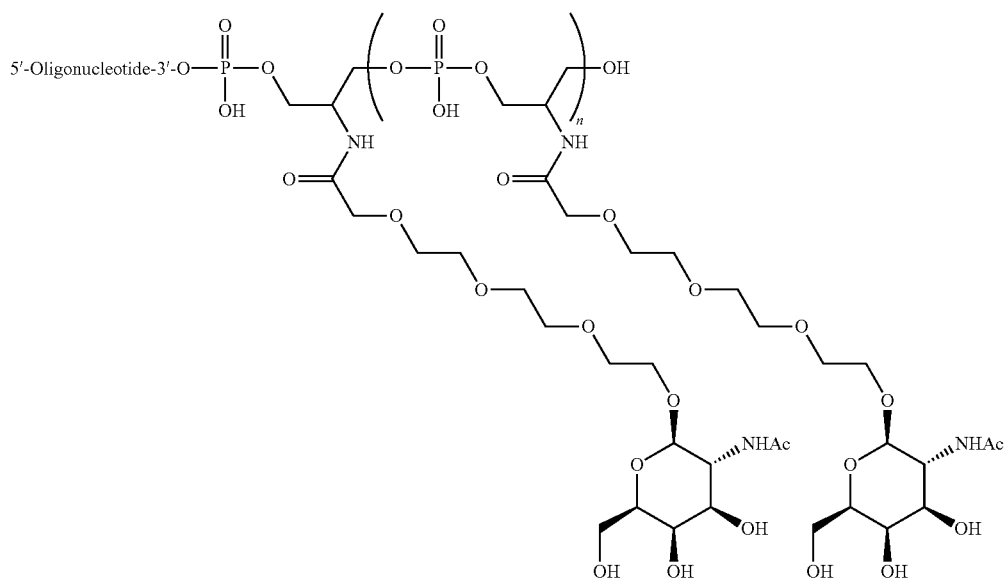

(VIII-OO)

32. The nucleic acid molecule of embodiment 27 to 29, where n is 1, 2 or 3.
33. The nucleic acid molecule of any one of embodiments 17-31, wherein the nucleic acid molecule is between 10 and 50 nucleotides in length.
34. The nucleic acid molecule of any one of embodiments 17-33, wherein the nucleic acid molecule comprises at least one modified nucleoside, which is/are particularly in each case independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
35. The nucleic acid molecule of embodiment 34, wherein the at least one modified nucleoside is an LNA nucleoside.
36. The nucleic acid molecule of embodiment 34 or 35, wherein the LNA nucleoside is a 2'-4'-bridged nucleoside selected from the group consisting of 2'-O—CH$_2$-4'-, 2'-O—CH$_2$—CH$_2$-4'-, 2'-O—CH(CH$_3$)-4'-, 2'-O—CH(OCH$_2$CH$_3$)-4'- and 2'-O—C(CH$_3$)$_2$-4'-nucleoside.
37. The nucleic acid molecule of embodiment 34-36, wherein the LNA nucleoside is a beta-D-oxy-LNA-nucleoside or an alpha-L-oxy-LNA-nucleoside.
38. The nucleic acid molecule of any one of embodiments 17-37, wherein the nucleic acid molecule comprises at least one modified internucleoside linkage.

39. The nucleic acid molecule of embodiment 38, wherein all the internucleoside linkages in the nucleic acid molecule are modified.
40. The nucleic acid molecule of embodiment 38 or 39, wherein the modified internucleoside linkage is a phosphorothioate internucleoside linkage.
41. The nucleic acid molecule of any one of embodiments 17-40, wherein the molecule is a single-stranded antisense oligonucleotide.
42. The nucleic acid molecule of any one of embodiments 17-40, wherein the nucleic acid molecule is capable of recruiting RNase H, particularly wherein the nucleic acid molecule is a gapmer.
43. The nucleic acid molecule of any one of embodiments 17-42, wherein the nucleic acid molecule is a gapmer of formula 5'-F-G-F'-3', where regions F and F' in each case independently comprise 1 to 7 modified nucleosides and G is a region between 6 and 16 nucleosides which are capable of recruiting RNase H.
44. The nucleic acid molecule of any one of embodiments 17-40, wherein the molecule is a double-stranded RNAi molecule.
45. The nucleic acid molecule of embodiment 44, wherein the compound having general formula (I) or the term $R^7O—(Y^1)_p$ or the term $(Y^2)_q—OR^8$ of general formula (IV) is associated with the sense strand of the molecule, wherein $R^7$, $R^8$, $Y^1$, and $Y^2$ are defined according to embodiment 18.
46. A pharmaceutical composition comprising the nucleic acid molecule of any one of embodiments 17-45 and a pharmaceutically acceptable diluent, solvent, carrier, salt and/or adjuvant.
47. The nucleic acid molecule of any one of embodiments 17-46 or the pharmaceutical composition of embodiment 46 for use in medicine, particularly in human medicine.

EXAMPLES

Example 1: Synthesis of DMT-Mono-GalNAc Phosphoramidites

This example describes the process of manufacturing DMT-mono-GalNAc phosphoramidite as a specific example of the trityl-mono-GalNAc phosphoramidites described above. The synthesis of the compound of general formula (XII) starting from a compound of general formula (IX) is exemplified by the following reaction scheme.

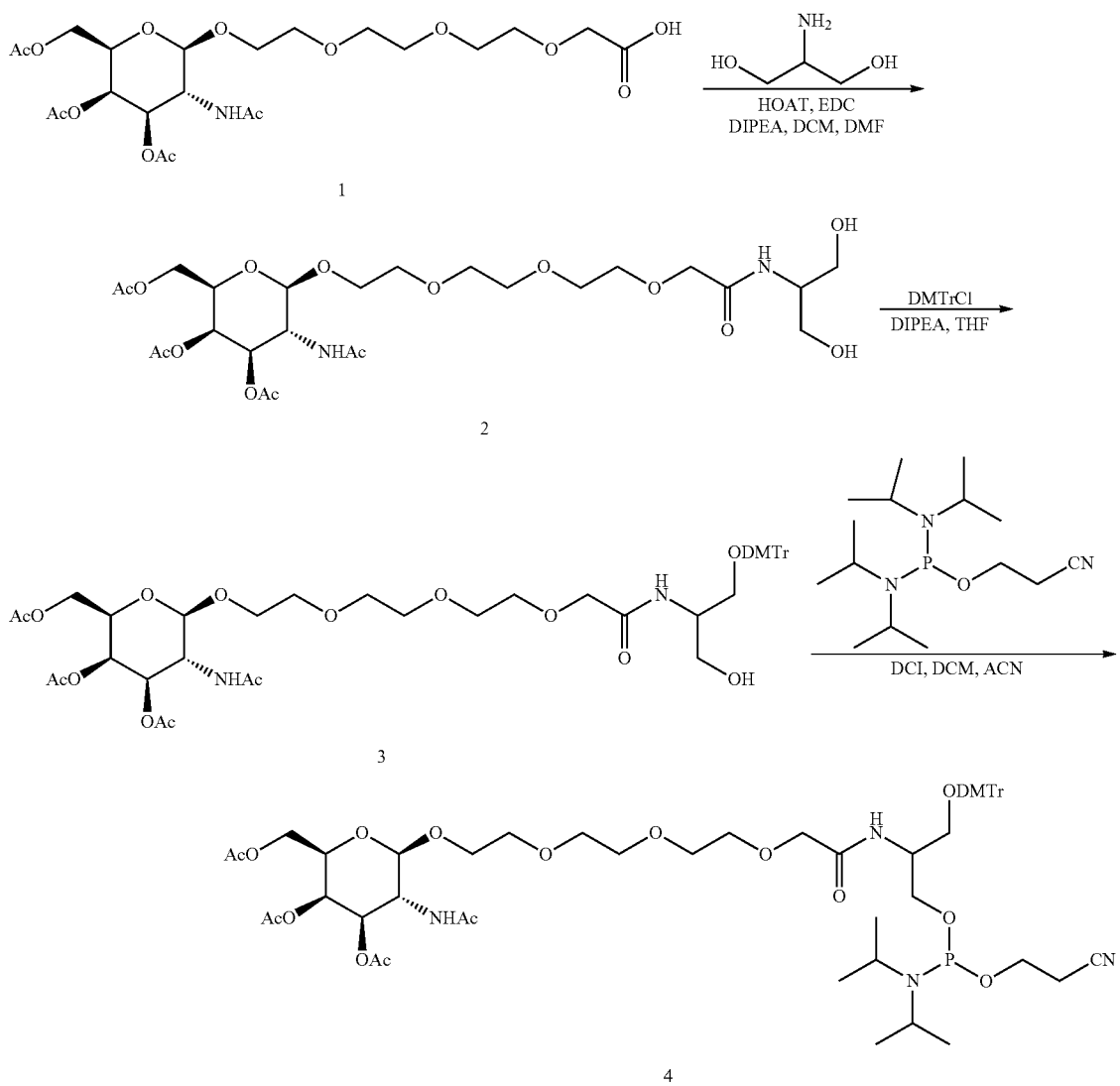

Compound 1 was prepared as described in WO 2012/083046 (page 54-55).

Compound 2 was produced as follows: To the solution of compound 1 (7.00 g, 12.1 mmol, co-evaporated with acetonitrile and toluene) in 60 mL dimethylformamide, serinol (1.37 g 15.0 mmol) and 1-hydroxybenzotriazole (HOAT, 2.04 g 15.0 mmol) was added. The reaction mixture was cooled to 0° C. (ice bath) and N-(3-dimethylaminopropyl)-N'-ethylcarbodiimide hydrochloride (EDC.HCl, 2.88 g 15.0 mmol) was added by portions during 20 min. The reaction mixture was stirred at room temperature for 5 h, water (5 mL) was added and the solvent was evaporated (50° C., 6 mbar). The residue was purified by silica gel chromatography (eluent ethanol in dichloromethane from 5% to 15%). Compound 2 was obtained as a colorless oil, 7.62 g.

Compound 3 was produced as follows: To solution of 2 (2.32 g 3.97 mmol, co-evaporated with acetonitrile and toluene three times) in 150 mL tetrahydrofuran, diisopropylethylamine (1.31 mL, 7.6 mmol) was added, followed by portion wise addition of 4,4'-dimethoxytrityl chloride (1.67 g 4.94 mmol) in 3 h. The reaction mixture was stirred at room temperature for 20 h. Water (1.5 ml) and ethanol (1.5 mL) was added and reaction the solvent was evaporated. The residue was purified by silica gel chromatography (eluent ethanol in dichloromethane from 0% to 20%). Compound 3 was obtained as a white foam, 2.27 g.

Compound 4 was produced as follows: To solution of 3 (2.60 g 2.85 mmol, co-evaporated with acetonitrile and toluene) in dichloromethane (55 mL) a solution of 4,5-dicyanoimidazole (DCI, 235 mg 2.00 mmol) in acetonitrile (5 mL) and solution of 2-Cyanoethyl tetraisopropylphosphorodiamidite (1.03 g 3.42 mmol) in DCM (5 mL) was added simultaneously in 20 min at 0° C. The reaction mixture was stirred at 0° C. and at room temperature for 3 h, diluted with dichloromethane (100 mL), extracted with sat. NaHCO$_3$ (100 mL), brine (100 mL), dried over Na$_2$SO$_4$ and evaporated. The residue was purified by silica gel chromatography (eluent ethylacetate in hexanes from 70% to 100%+5% triethylamine). Compound 4 was obtained as a white foam, 2.72 g.

Example 2: Synthesis of Oligonucleotides

Crude oligonucleotides were synthesized in DMT-ON mode at 1 µmol scale on a NittoPhase UnyLinker 200 support by standard phosphoramidite chemistry. 4,5-dicyanoimidazole (0.5M in acetonitrile) was used as activator. Xanthane hydride (22 mM in pyridine/acetonitrile 1:5) was used for thiooxidation. Oxidizer 0.05M (SAFC, catalogue number L560250) was used for oxidation. Standard DNA phosphoramidites with benzoyl protected A and C and isobutyryl protected G were used. LNA phosphoramidites with benzoyl protected A and 5-methyl-C and dimethylformamidine protected LNA-G were used. Coupling times for DNA and LNA monomers were 2×3 and 5 minutes respectively. For monomer 4 the coupling was extended to 2×10 minutes. After end synthesis, the support was suspended in 0.5 mL concentrated ammonium hydroxide at 60° C. for 16 hours. The support was filtered off and the solution was evaporated to dryness under vacuum. The crude DMT-ON oligonucleotide was purified on a solid phase extraction cartridge (Waters Oasis HLB 6 cc 200 mg). The cartridge was first equilibrated with acetonitrile and 0.1M ammonium acetate. The crude oligonucleotide was applied dissolved in 0.1M ammonium acetate and the cartridge was eluted with 15% acetonitrile in 0.1M ammonium acetate. The DMT group was removed by 3% trifluoroacetic acid for 10 min and the column was added 0.1M ammonium acetate followed by water. The oligonucleotide was eluted with 15% acetonitrile in water and the solvent was evaporated to give the pure compound. The purity and identity was confirmed by UPLC-MS analysis.

Example 3: Specific Mono-GalNAc Nucleic Acid Conjugates

Using the DMT-mono-GalNAc phosphoramidite of Example 1 in the oligonucleotide synthesis of Example 2, the GalNAc nucleic acid conjugates shown in table 1 and 2 were synthesized.

The general formula of an exemplary oligonucleotide conjugate with one or more mono-GalNAc moieties of the invention incorporated at the 5'-end of the oligonucleotide is represented by the following formula (VII):

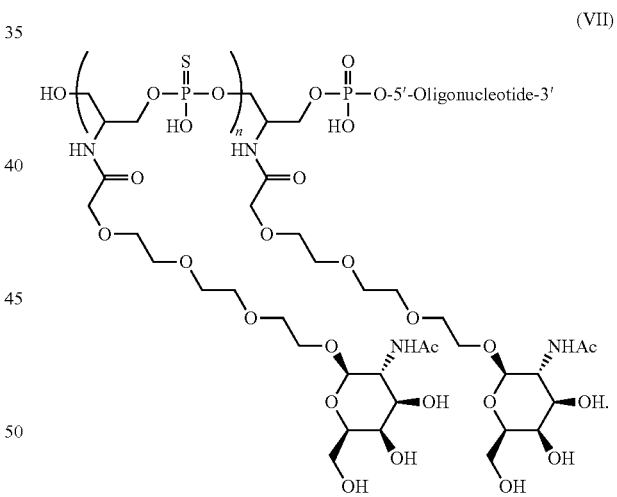

(VII)

Specific compounds based on this general formula (VII) have been synthesized and are represented by compound A, B, C and D in table 2.

TABLE 2

| | | 5' conjugated nucleic acid compounds | |
|---|---|---|---|
| Compound | n | 5'-Oligonucleotide-3' | GalNAc moieties at the 5' end |
| A | 0 | 5'-c$_O$a$_O$G$_S$$^m$C$_S$a$_S$t$_S$t$_S$g$_S$g$_S$t$_S$a$_S$t$_S$T$_S$$^m$C$_S$A-3' | Mono-valent |
| B | 1 | 5'-c$_O$a$_O$G$_S$$^m$C$_S$a$_S$t$_S$t$_S$g$_S$g$_S$t$_S$a$_S$t$_S$T$_S$$^m$C$_S$A-3' | Di-valent |

TABLE 2-continued

5' conjugated nucleic acid compounds

| Compound | n | 5'-Oligonucleotide-3' | GalNAc moieties at the 5' end |
|---|---|---|---|
| C | 2 | 5'-c$_O$a$_O$G$_S$$^m$C$_S$a$_S$t$_S$t$_S$g$_S$g$_S$t$_S$a$_S$t$_S$T$_S$$^m$C$_S$A-3' | Tri-valent |
| D | 3 | 5'-c$_O$a$_O$G$_S$$^m$C$_S$a$_S$t$_S$t$_S$g$_S$g$_S$t$_S$a$_S$t$_S$T$_S$$^m$C$_S$A-3' | Tetra-valent |

Upper case = beta-D-oxy LNA, lower case = DNA, $_O$ = phosphordiester, $_S$ = phosphorthioate, $^m$C = 5-methylcytosine. The oligonucleotide sequence of compounds A-D corresponds to SEQ ID NO: 2.

Similarly, the general formula of an exemplary oligonucleotide conjugate with one or more mono-GalNAc moieties incorporated at the 3'-end of the oligonucleotide is represented by the following formula (VIII):

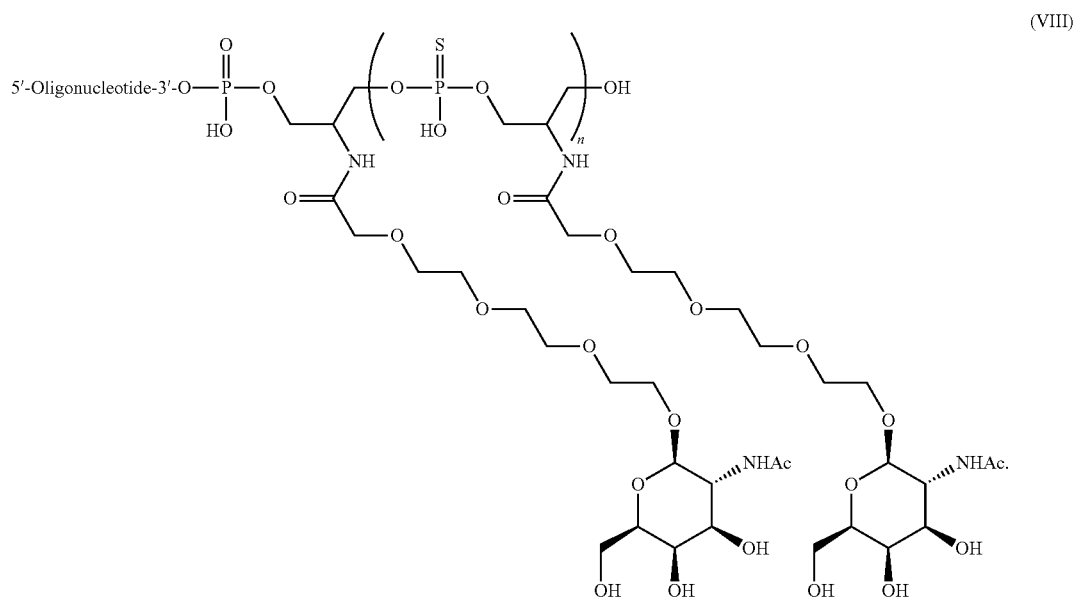

(VIII)

One specific compounds based on this general formula (VIII) has been synthesized and is represented by compound E in table 3.

TABLE 3

3' conjugated nucleic acid compounds

| Compound | n | 5'-Oligonucleotide-3' | GalNAc moieties at the 3' end |
|---|---|---|---|
| E | 2 | 5'-G$_S$$^m$C$_S$a$_S$t$_S$t$_S$g$_S$g$_S$t$_S$a$_S$t$_S$T$_S$$^m$C$_S$A$_O$c$_O$a-3' | Tri-valent |

Upper case = beta-D-oxy LNA, lower case = DNA, $_S$ = phosphorthioate, $^m$C = 5-methylcytosine. The oligonucleotide sequence of compound E corresponds to SEQ ID NO: 3.

For comparative purposes, the following reference compounds F (naked oligonucleotide, i.e. no GalNAc) and G (custom made trivalent GalNAc) have been prepared as presented in table 4.

TABLE 4 reference compounds

| Compound | 5'-Oligonucleotide-3' | GalNAc moieties at the 5' end |
|---|---|---|
| F | 5'-G$_S$$^m$C$_S$a$_S$t$_S$t$_S$g$_S$g$_S$t$_S$a$_S$t$_S$T$_S$$^m$C$_S$A-3' | none |
| G | 5'-GalNAc2$_S$G$_S$$^m$C$_S$a$_S$t$_S$t$_S$g$_S$g$_S$t$_S$a$_S$t$_S$T$_S$$^m$C$_S$A-3' | Tri-valent (GalNAc2) |

Upper case = beta-D-oxy LNA, lower case = DNA, $_S$ = phosphorthioate, $^m$C = 5-methylcytosine. The oligonucleotide sequence of compound E corresponds to SEQ ID NO: 3.

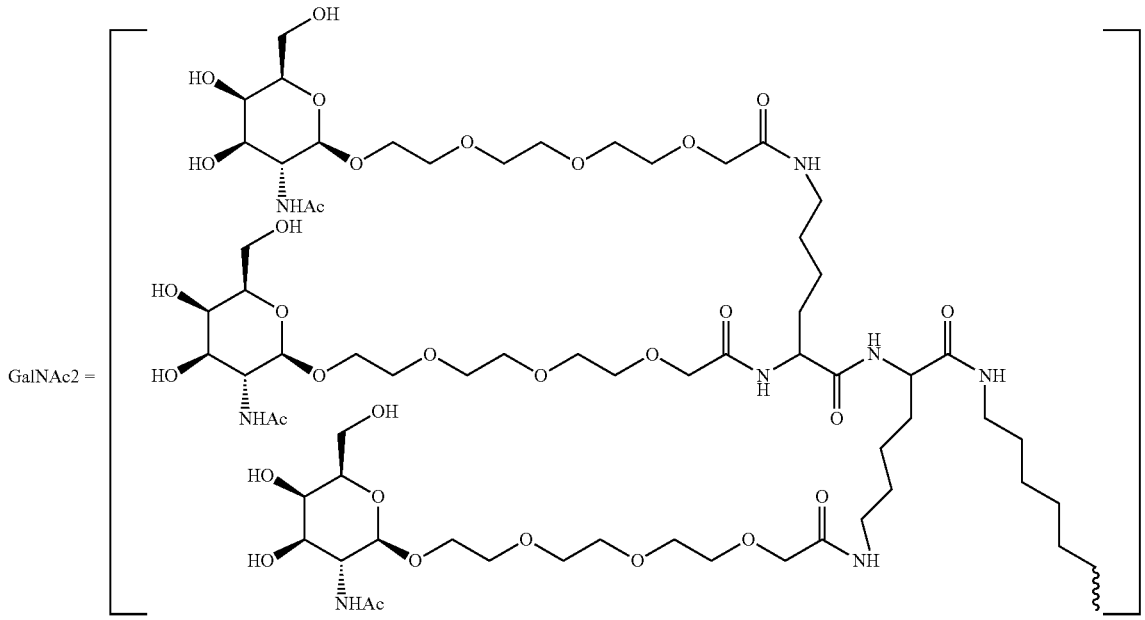

Example 4: In Vivo Effect of GalNAc Oligonucleotide Conjugates Made from Mono-DMT-Mono-GalNAc-Phosphoramidites Black 6 mice were subjected to the oligonucleotide conjugates or control compounds represented in tables 1 to 3 and the knock down of ApoB mRNA, the tissue content of the oligonucleotides and total cholesterol was measured.

Female C57BL6/J mice (5/group appr. 20 g at arrival) were injected subcutaneous (sc) with a single dose saline or 0.25 mg/kg unconjugated LNA-antisense oligonucleotide (compound F) or with 0.25 mg/kg or 0.1 mg/kg of GalNAc conjugated LNA antisense oligonucleotide (Compound C or E of the invention or reference compound G). Blood samples of 50 µl were collected pre-dosing at day minus 6, and post dosing at day 3 and 7. The animals were sacrificed at day 10 and total serum was collected as well as liver and kidney.

ApoB mRNA knockdown was analyzed by qPCR. In brief, RNA was isolated from homogenized liver and kidney using MagnaPure RNA Isolation and purification system (catalog #03604721001 and #05467535001; Roche) according to the manufacturer's instructions. RT-QPCR was done using Taqman Fast Universal PCR Master Mix 2×(Applied Biosystems Cat #4364103) and Taqman gene expression assay (mApoB, Mn01545150_m1 and mGAPDH #4352339E) following the manufacturers protocol. The results are shown in Table 5.

TABLE 5

| | ApoB mRNA expression as % of saline. | | | | | | | |
|---|---|---|---|---|---|---|---|---|
| | 0.1 mg/kg | | | | 0.25 mg/kg | | | |
| Compound | mRNA liver | SD | mRNA kidney | SD | mRNA liver | SD | mRNA kidney | SD |
| F (naked oligo) | NA | | NA | | 74.5 | 6.4 | 24.7 | 2.8 |
| G (GalNAc2) | 72.1 | 10.5 | 88.2 | 10.5 | 49.0 | 11.4 | 94.7 | 16.6 |
| C (5' tri-GalNAc) | 69.6 | 17.5 | 72.4 | 20.6 | 24.0 | 4.3 | 56.1 | 16.2 |
| E (3' tri-GalNAc) | 60.5 | 7.5 | 84.8 | 7.8 | 34.9 | 9.8 | 51.0 | 19.9 |

The oligonucleotide content in the liver and kidney was measured using ELISA (see for example Straarup et al 2010 Nucleic Acid Res Vol 38 pp 7100-7111), results are shown in Table 6.

TABLE 6

Oligonucleotide content in liver and kidney

| Compound | 0.1 mg/kg | | | | 0.25 mg/kg | | | |
|---|---|---|---|---|---|---|---|---|
| | Liver (µg/g tissue) | SD | Kidney (µg/g tissue) | SD | Liver (µg/g tissue) | SD | Kidney (µg/g tissue) | SD |
| F (naked oligo) | NA | | NA | | 0.028 | 0.003 | 1.370 | 0.144 |
| G (GalNAc2) | 0.043 | 0.003 | 0.135 | 0.015 | 0.152 | 0.037 | 0.299 | 0.055 |
| C (5' tri-GalNAc) | 0.028 | 0.006 | 0.080 | 0.008 | 0.028 | 0.006 | 0.080 | 0.008 |
| E (3' tri-GalNAc) | 0.021 | 0.003 | 0.094 | 0.014 | 0.069 | 0.013 | 0.243 | 0.068 |

Total cholesterol in serum was measured using ABX Pentra Cholesterol CP (Triolab, Brondby, Denmark) according to the manufacturer's instructions. The results are shown in FIG. 1.

ALT (Alanine aminotransferase) was measured using ABX Pentra ALT CP reagent (A11A01627 Triolab, Brondby, Denmark. The results are shown in Table 7.

TABLE 7

ALT levels in serum at day 10 as % of saline L

| Compound | 0.1 mg/kg | | 0.25 mg/kg | |
|---|---|---|---|---|
| | ALT U/L | SD | ALT U/L | SD |
| F (naked oligo) | NA | | 97 | 14 |
| G (GalNAc2) | 116 | 12 | 109 | 23 |
| C (5' tri-GalNAc) | 101 | 8 | 119 | 28 |
| E (3' tri-GalNAc) | 100 | 22 | 113 | 19 |

Conclusions:

The new GalNAc oligonucleotide conjugates made with DMT-mono-GalNAc phosphoramidites conjugated to an ApoB LNA antisense oligonucleotide (compounds C and E) showed improved knock down of ApoB mRNA in the liver when compared to unconjugated (naked) ApoB LNA oligonucleotide (compound F). The 3' conjugated new GalNAc oligonucleotide conjugate construct (compound E) showed knock down of ApoB mRNA comparable to the GalNAc2 cluster conjugated LNA oligonucleotide (compound G) whereas the 5' conjugated new GalNAc oligonucleotide conjugate construct (compound C) showed better knockdown than the GalNAc2 conjugated LNA oligonucleotide at the high dose concentrations (Table 5). At the lower dose level (0.1 mg/kg) the GalNAc conjugated LNA oligonucleotides showed comparable knock down of ApoB mRNA in liver. The data showing reduction of total cholesterol correlate with the observations in relation to mRNA knock down (FIG. 1a and FIG. 1b).

The tissue content of the oligonucleotides (Table 6) shows how the GalNAc conjugated LNA oligonucleotides (compound C, E and G) have enhanced uptake in the liver and reduced uptake in the kidney compared to the unconjugated oligonucleotide (compound F). Furthermore, the 5' conjugated new GalNAc oligonucleotide conjugate construct (compound C) appears to have an improved liver/kidney distribution ratio when compared to the GalNAc2 conjugated LNA oligonucleotide (compound G) at the high dose.

All the tested compounds were safe. None of the tested construct showed elevated ALT readout as shown in Table 7.

Example 5: GalNAc Nucleic Acid Conjugates with Varying PS and PO Linkage Between the Mono-GalNAc Units and the Oligonucleotide Using the DMT-mono-GalNAc phosphoramidite of Example 1 in the oligonucleotide synthesis of Example 2, the GalNAc nucleic acid conjugates shown in table 8 were synthesized.

The molecules differ from those in example 3 in that the biocleavable ca phosphodiester (PO) linked dinucleotide is removed, substituted with or supplemented with phosphodiester linkages between the mono-GalNAc units instead of the phosphorthioate (PS) linkages in formula (VII).

TABLE 8

Trivalent and divalent GalNAc compounds incorporated at the 5' end of a nucleic acid molecule

| Compound | n | X | Y | 5'-Oligonucleotide-3' | SEQ ID NO |
|---|---|---|---|---|---|
| H | 2 | S | S | 5'-$G_S{}^mC_Sa_St_St_Sg_Sg_St_Sa_St_ST_S{}^mC_SA$-3' | 1 |
| I | 2 | S | O | 5'-$G_S{}^mC_Sa_St_St_Sg_Sg_St_Sa_St_ST_S{}^mC_SA$-3' | 1 |
| J | 2 | O | O | 5'-$G_S{}^mC_Sa_St_St_Sg_Sg_St_Sa_St_ST_S{}^mC_SA$-3' | 1 |
| K | 2 | O | O | 5'-$c_Oa_OG_S{}^mC_Sa_St_St_Sg_Sg_St_Sa_St_ST_S{}^mC_SA$-3' | 2 |
| L | 1 | O | O | 5'-$G_S{}^mC_Sa_St_St_Sg_Sg_St_Sa_St_ST_S{}^mC_SA$-3' | 1 |

Upper case = beta-D-oxy LNA, lower case = DNA, $_O$ = phosphodiester, S = phosphorthioate, $^mC$ = 5-methylcytosine.

The general formula of the exemplary oligonucleotide conjugates with one or more mono-GalNAc moieties of the invention incorporated at the 5'-end of the oligonucleotide (table 8) is represented by the following formula (VII-XY):

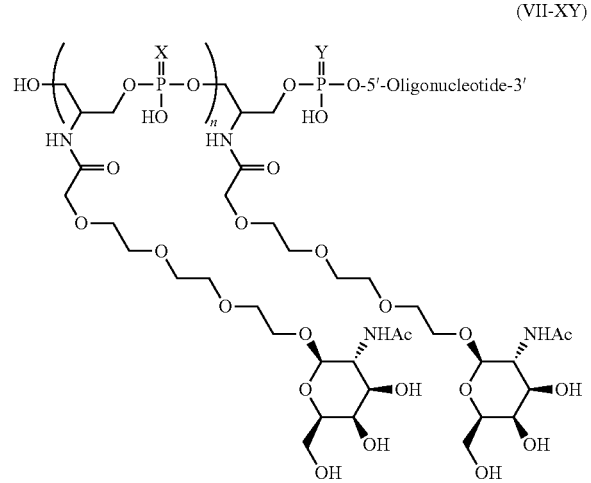

(VII-XY)

In addition to the reference compounds in table 4, reference compound M was produced 5'-GalNAc2$_O$c$_O$a$_O$G$_S$$^m$C$_S$a$_S$t$_S$t$_S$g$_S$g$_S$t$_S$a$_S$t$_S$T$_S$$^m$C$_S$A-3' (SEQ ID NO:2). This compound differs from reference compound G by having a biocleavable linker in the form of a phosphodiester linked ca dinucleotide between the antisense oligonucleotide (SEQ ID NO 1) which is complementary to the target nucleic acid and the GalNAc2 moiety.

Example 6: Varying PS and PO Linkages Between the Mono-GalNAc Units and the Antisense Oligonucleotide Black 6 mice were subjected to the oligonucleotide conjugates with varying phosphorthioate (PS) and phosphodiester (PO) linkages between the mono-GalNAc units and the antisense oligonucleotide compound. Knock down of ApoB mRNA, tissue content of the oligonucleotides, total cholesterol and ALT was measured.

Female C57BL6/J mice (5/group appr. 20 g at arrival) were injected intravenous (iv) with a single dose saline, 0.22 mg/kg, 0.45 mg/kg or 0.89 mg/kg, of GalNAc conjugated LNA antisense oligonucleotide (Compound H, I or J of the invention) or the naked reference compound F. Blood samples of 50 μl were collected pre-dosing at day minus 6. The animals were sacrificed at day 3. Total serum was collected as well as liver and kidney.

ApoB mRNA knock down was measured as described in example 4, and the results are shown in table 9 and 10.

TABLE 9

ApoB mRNA/mGAPDH expression as % of saline in liver.

| Compound | 0.22 mg/kg | | 0.45 mg/kg | | 0.89 mg/kg | |
|---|---|---|---|---|---|---|
| | Avg | SD | Avg | SD | Avg | SD |
| F (naked oligo) | 87.5 | 6.9 | 90.2 | 14.1 | 53.8 | 16.1 |
| H (3xPS) | 97.0 | 13.7 | 71.4 | 22.9 | 50.4 | 7.1 |
| I 2PS, 1PO | 44.9 | 8.9 | 23.4 | 7.7 | 9.8 | 3.7 |
| J (3xPO) | 12.8 | 2.6 | 6.3 | 2.3 | 3.0 | 1.1 |

TABLE 10

ApoB mRNA expression as % of saline in kidney

| Compound | 0.22 mg/kg | | 0.45 mg/kg | | 0.89 mg/kg | |
|---|---|---|---|---|---|---|
| | Avg | SD | Avg | SD | Avg | SD |
| F (naked oligo) | 68.0 | 14.6 | 51.1 | 12.1 | 29.0 | 5.3 |
| H (3xPS) | 100.4 | 25.2 | 93.3 | 27.5 | 84.4 | 18.6 |
| I 2PS, 1PO | 91.2 | 18.3 | 98.4 | 19.5 | 67.9 | 14.3 |
| J (3xPO) | 117.0 | 13.3 | 90.7 | 8.8 | 64.1 | 8.9 |

The oligonucleotide content in the liver and kidney was measured using ELISA (see for example Straarup et al 2010 Nucleic Acid Res Vol 38 pp 7100-7111), results are shown in Table 11A and 11B.

TABLE 11A

Oligonucleotide content in μg/g liver tissue

| Compound | 0.22 mg/kg | | 0.45 mg/kg | | 0.89 mg/kg | |
|---|---|---|---|---|---|---|
| | Avg | SD | Avg | SD | Avg | SD |
| F (naked oligo) | 0.059 | 0.013 | 0.173 | 0.041 | 0.470 | 0.045 |
| H (3xPS) | 0.246 | 0.046 | 0.519 | 0.059 | 1.394 | 0.269 |
| I 2PS, 1PO | 0.276 | 0.033 | 0.561 | 0.038 | 1.349 | 0.302 |
| J (3xPO) | 0.313 | 0.070 | 0.710 | 0.266 | 1.478 | 0.112 |

TABLE 11B

Oligonucleotide content in μg/g kidney tissue

| Compound | 0.22 mg/kg | | 0.45 mg/kg | | 0.89 mg/kg | |
|---|---|---|---|---|---|---|
| | Avg | SD | Avg | SD | Avg | SD |
| F (naked oligo) | 0.337 | 0.138 | 0.506 | 0.064 | 1.050 | 0.277 |
| H (3xPS) | 0.255 | 0.087 | 0.647 | 0.021 | 0.960 | 0.194 |
| I 2PS, 1PO | 0.359 | 0.110 | 0.513 | 0.071 | 1.089 | 0.308 |
| J (3xPO) | 0.169 | 0.050 | 0.549 | 0.266 | 1.040 | 0.301 |

Total cholesterol in serum was measured using ABX Pentra Cholesterol CP (Triolab, Brondby, Denmark) according to the manufacturer's instructions. The results are shown in table 12.

TABLE 12 serum cholesterol percent of saline

| Compound | 0.22 mg/kg | | 0.45 mg/kg | | 0.89 mg/kg | |
|---|---|---|---|---|---|---|
| | Avg | SD | Avg | SD | Avg | SD |
| F (naked oligo) | 104.3 | 5.8 | 86.8 | 8.2 | 66.9 | 11.0 |
| H (3xPS) | 100.5 | 11.5 | 90.0 | 17.8 | 83.6 | 12.9 |
| I 2PS, 1PO | 84.6 | 11.9 | 50.7 | 12.3 | 25.2 | 6.8 |
| J (3xPO) | 37.3 | 5.1 | 21.5 | 5.7 | 10.0 | 3.8 |

ALT (Alanine aminotransferase) was measured using ABX Pentra ALT CP reagent (A11A01627 Triolab, Brondby, Denmark. The results are shown in Table 13.

TABLE 13

ALT levels (U/L) in serum at day 3 as % of saline

| Compound | 0.22 mg/kg Avg | SD | 0.45 mg/kg Avg | SD | 0.89 mg/kg Avg | SD |
|---|---|---|---|---|---|---|
| F (naked oligo) | 91 | 56 | 151 | 65 | 217 | 125 |
| H (3xPS) | 160 | 113 | 253 | 121 | 119 | 29 |
| I 2PS, 1PO) | 98 | 60 | 166 | 63 | 171 | 41 |
| J (3xPO) | 101 | 8 | 201 | 52 | 1558 | 1138 |

Conclusions:

All the GalNAc oligonucleotide conjugates made with DMT-mono-GalNAc phosphoramidites incorporated into an ApoB LNA antisense oligonucleotide (compounds H, I and J) showed improved liver to kidney ratio when compared to unconjugated (naked) ApoB LNA oligonucleotide (compound F) (tables 9 to 11). To achieve improved ApoB knock down in the liver and serum cholesterol reduction at least one phosphodiester linkage had to be present (compound I and J, tables 9 and 12). Generally the tested compounds were safe in terms of hepatotoxicity. For compound J some animals showed increase ALT levels at the highest dose, this is likely to be due to exaggerated pharmacology (table 13).

Example 7: Varying the Position of the PO Linkage

Black 6 mice were subjected to oligonucleotide conjugates with phosphodiester (PO) nucleoside linkages at different positions between the mono-GalNAc units and the antisense oligonucleotide compound (table 14). Knock down of ApoB mRNA, tissue content of the oligonucleotides, total cholesterol and ALT was measured.

TABLE 14 trivalent and divalent GalNAc compounds incorporated at the 5' end of a nucleic acid molecule

| Compound | n | X | Y | 5'-Oligonucleotide-3' | SEQ ID |
|---|---|---|---|---|---|
| M | — | — | — | GalNAc2$_O$c$_O$a$_O$G$_S$$^m$C$_S$a$_S$t$_S$t$_S$g$_S$g$_S$t$_S$a$_S$t$_S$T$_S$$^m$C$_S$A-3' | 2 |
| J | 2 | O | O | 5'-G$_S$$^m$C$_S$a$_S$t$_S$t$_S$g$_S$g$_S$t$_S$a$_S$t$_S$T$_S$$^m$C$_S$A-3' | 1 |
| K | 2 | O | O | 5'-c$_O$a$_O$G$_S$$^m$C$_S$a$_S$t$_S$t$_S$g$_S$g$_S$t$_S$a$_S$t$_S$T$_S$$^m$C$_S$A-3' | 2 |
| C | 2 | S | O | 5'-c$_O$a$_O$G$_S$$^m$C$_S$a$_S$t$_S$t$_S$g$_S$g$_S$t$_S$a$_S$t$_S$T$_S$$^m$C$_S$A-3' | 2 |
| L | 1 | O | O | 5'-G$_S$$^m$C$_S$a$_S$t$_S$t$_S$g$_S$g$_S$t$_S$a$_S$t$_S$T$_S$$^m$C$_S$A-3' | 1 |
| B | 1 | S | O | 5'-c$_O$a$_O$G$_S$$^m$C$_S$a$_S$t$_S$t$_S$g$_S$g$_S$t$_S$a$_S$t$_S$T$_S$$^m$C$_S$A-3' | 2 |

Upper case = beta-D-oxy LNA lower case = DNA, $_O$ = phosphordiester, $_S$ = phosphorthioate, $^m$C = 5-methylcytosine.

Female C57BL6/J mice (5/group appr. 20 g at arrival) were injected intravenous (iv) with a single dose saline or 0.1 mg/kg of GalNAc conjugated LNA antisense oligonucleotide (Compound J, K, L, B or C of the invention or reference compound M). Blood samples of 50 µl were collected pre-dosing at day minus 6, and post dosing at day 3, 7, 10 and 14. The animals were sacrificed at day 7 or 14 and total serum was collected as well as liver and kidney.

ApoB mRNA knock down was measured as described in example 4. The results are shown in table 15.

TABLE 15

ApoB mRNA/mGAPDH expression as % of saline in liver and kidney

| Compound | Total PO | Day 7 Avg liver | SD | Avg kidney | SD | Day 14 Avg liver | SD | Avg kidney | SD |
|---|---|---|---|---|---|---|---|---|---|
| M -Trivalent GalNAc2 ca biocleavable linker | 2 | 38.1 | 7.9 | 73.9 | 13.9 | 73.4 | 16.4 | 62.0 | 6.8 |
| J - Trivalent PO at X and Y | 3 | 56.0 | 9.2 | 83.9 | 10.8 | 107.6 | 28.7 | 96.8 | 8.4 |
| K - Trivalent PO at X and Y ca biocleavable linker | 5 | 48.7 | 7.7 | 80.2 | 8.8 | 112.4 | 14.4 | 86.2 | 11.1 |
| C - Trivalent PS at X and PO at Y ca biocleavable linker | 3 | 63.2 | 7.6 | 93.8 | 12.2 | 116.3 | 14.2 | 74.4 | 10.4 |
| L - Divalent PO at X and Y | 2 | 47.3 | 4.9 | 46.8 | 29.9 | 121.7 | 18.5 | 87.9 | 5.6 |
| B -Divalent PS at X and PO at Y ca biocleavable linker | 3 | 49.2 | 7.1 | 62.5 | 13.5 | 112.8 | 22.1 | 100.3 | 14.7 |

The oligonucleotide content in the liver and kidney was measured using ELISA (see for example Straarup et al 2010 Nucleic Acid Res Vol 38 pp 7100-7111), results are shown in Table 16.

TABLE 16

Oligonucleotide content in μg/g liver or kidney tissue

| Compound | Total PO | Day 7 | | | | Day 14 | | | |
|---|---|---|---|---|---|---|---|---|---|
| | | Avg liver | SD | Avg kidney | SD | Avg liver | SD | Avg kidney | SD |
| M -Trivalent GalNAc2 ca biocleavable linker | 2 | 0.836 | 0.070 | 0.419 | 0.047 | 0.523 | 0.114 | 0.230 | 0.038 |
| J - Trivalent PO at X and Y | 3 | 0.276 | 0.081 | 0.153 | 0.031 | 0.163 | 0.034 | 0.079 | 0.008 |
| K - Trivalent PO at X and Y ca biocleavable linker | 5 | 0.401 | 0.099 | 0.275 | 0.041 | 0.173 | 0.074 | 0.129 | 0.011 |
| C - Trivalent PS at X and PO at Y ca biocleavable linker | 3 | 0.493 | 0.120 | 0.307 | 0.031 | 0.209 | 0.032 | 0.118 | 0.009 |
| L - Divalent PO at X and Y | 2 | 0.152 | 0.013 | 0.269 | 0.038 | 0.051 | 0.019 | 0.112 | 0.017 |
| B -Divalent PS at X and PO at Y ca biocleavable linker | 3 | 0.161 | 0.011 | 0.353 | 0.037 | 0.066 | 0.017 | 0.152 | 0.024 |

Figure 2:
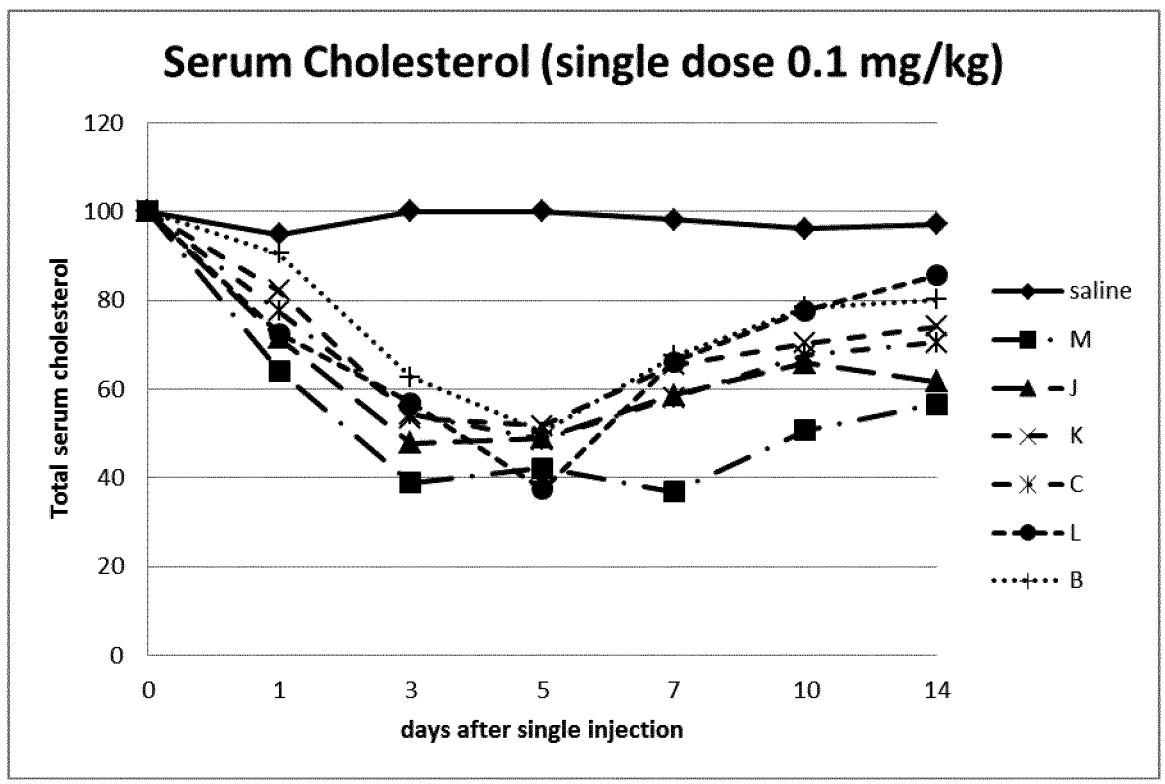
FIG. 2: Total serum cholesterol in mice 14 days after injection of different oligonucleotide conjugates at a single dose of 0.1 mg/kg.

Total cholesterol in serum was measured using ABX Pentra Cholesterol CP (Triolab, Brondby, Denmark) according to the manufacturer's instructions. The results are shown in FIG. 2.

ALT (Alanine aminotransferase) was measured using ABX Pentra ALT CP reagent (A11A01627 Triolab, Brondby, Denmark. The results are shown in table 17.

TABLE 17

ALT levels (U/L) in serum at day 3 as % of saline

| Compound | Total PO | Day 7 | | Day 14 | |
|---|---|---|---|---|---|
| | | Avg | SD | Avg | SD |
| M -Trivalent GalNAc2 ca biocleavable linker | 2 | 116.7 | 29.8 | 128.5 | 56.9 |
| J - Trivalent PO at X and Y | 3 | 128.6 | 16.7 | 126.1 | 52.0 |
| K - Trivalent PO at X and Y ca biocleavable linker | 5 | 170.3 | 20.0 | 77.3 | 14.0 |
| C - Trivalent PS at X and PO at Y ca biocleavable linker | 3 | 136.7 | 18.7 | 111.3 | 32.5 |
| L - Divalent PO at X and Y | 2 | 130.2 | 21.2 | 108.1 | 11.2 |
| B -Divalent PS at X and PO at Y ca biocleavable linker | 3 | 177.3 | 40.7 | 108.5 | 27.9 |

Conclusion:

All the GalNAc conjugated compounds were capable of reducing ApoB mRNA levels as well as cholesterol levels after a single treatment with only 0.1 mg/kg (table 15 and FIG. 2). The duration of action seems to be a bit shorter for the compounds of the invention compared to the control compound with the GalNAc2 moiety (table 15 day 14). All the compounds were functional regardless of the position of the cleavable phosphodiester (PO) linkage. The divalent conjugated antisense oligonucleotide appears to be just as potent as the trivalent conjugated antisense oligonucleotides despite the fact that the total amount of oligonucleotide in the liver for these molecules is lower than for the trivalent conjugated molecules (table 16). None of the molecules showed signs of ALT elevations.

The overall conclusion is therefore that the overall design spectrum for GalNAc conjugated antisense oligonucleotides is quite broad and allows for optimization depending on the purpose.

Example 8: Preparation of Stereodefined Mono-GalNAc Phosphoramidites

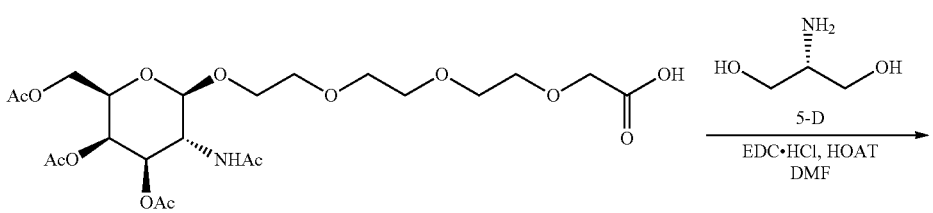

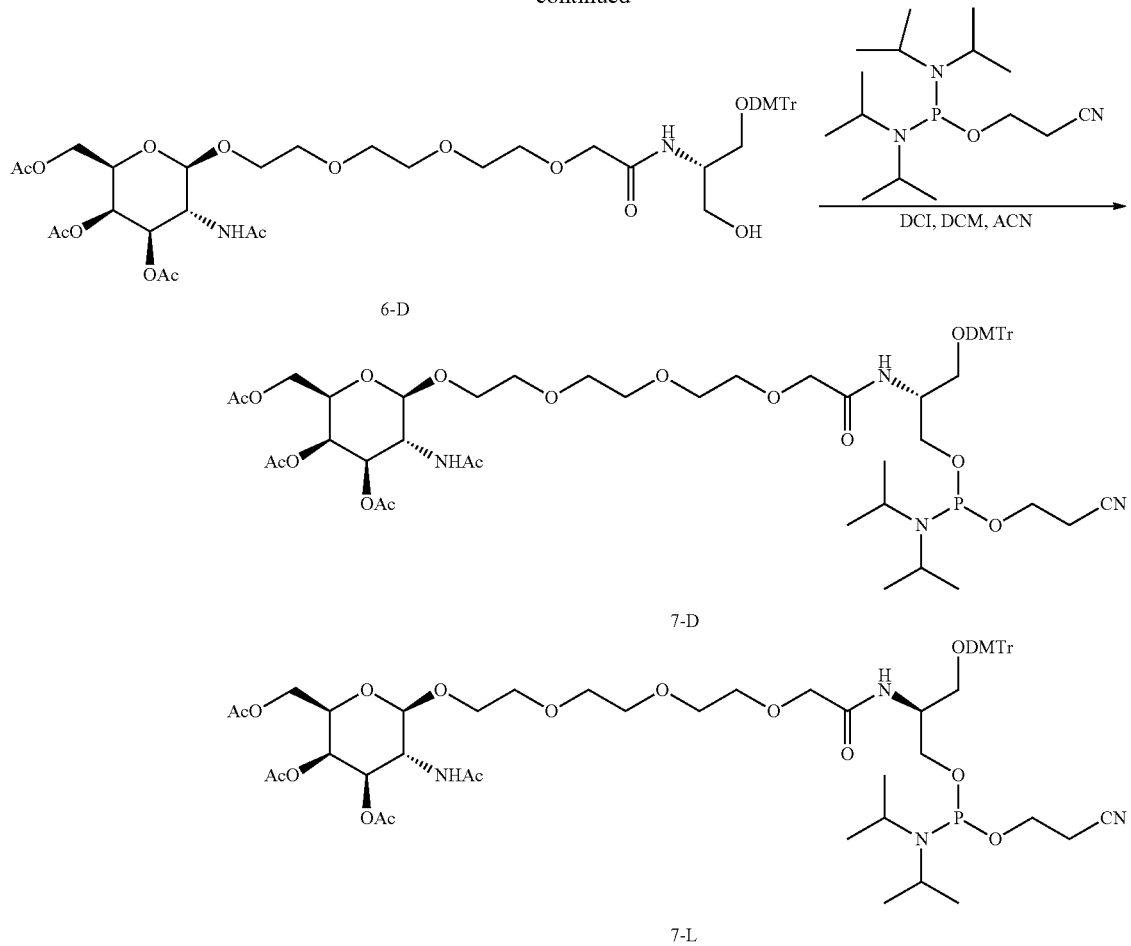

6-D

7-D

7-L

DMT-protected serinol 5-L and 5-D were prepared from L- and D-serine methyl ester respectively as described in Putnam and Bashkin 2006 Nucleosides, Nucleotides, and Nucleic Acids, 24 (9):1309-1323.

Compound 6-D was produced as follows: To a solution of 1 (1.23 g, 2.29 mmol, co-evaporated with MeCN and toluene) in DMF (12 mL) 5-D (900 mg, 2.29 mmol) and HOAT (311 mg, 2.29 mmol) was added. The reaction mixture was cooled to 0° C. (ice bath) and EDC-HCl (438 mg, 2.29 mmol) was added by portions during 20 min. The reaction mixture was stirred at room temperature for 26 h. Water (1 mL) was added and mixture was evaporated. EtOAc (70 mL) was added to the residue and mixture was extracted with 10% citric acid (30 mL), sat. NaHCO$_3$ (30 mL), brine (30 mL), dried over Na$_2$SO$_4$ and evaporated. The residue was purified by column chromatography (eluent EtOH in DCM from 2% to 8%) to give compound 6-D as a white foam, 1.77 g.

The same procedure was used to prepare compound 6-L.

Compound 7-D was produced as follows: To solution of 6-D (1.65 g, 1.81 mmol, co-evaporated with MeCN, toluene (3×)) in DCM (20 mL), a solution of 2-Cyanoethyl tetraisopropylphosphorodiamidite (599 mg, 1.99 mmol) in DCM (15 mL) and solution of 4,5-dicyanoimidazole (DCI, 149 mg, 1.27 mmol) in MeCN (2.5 mL) was added simultaneously in 25 min at 0° C. The reaction mixture was stirred at 0° C. for 30 min and at room temperature for 3 h, diluted with DCM (100 mL), extracted with sat. NaHCO$_3$ (50 mL), brine (50 mL), dried over Na$_2$SO$_4$ and evaporated. The residue was purified by column chromatography (eluent EtOAc in hexanes from 60% to 100%+5% NEt$_3$) to give compound 7-D as a white solid, 1.23 g.

The same procedure was used to prepare compound 7-L.

Example 9: Investigating Performance of GalNAc Conjugates with Stereodefined Mono-GalNAc Moieties Incorporation of the mono-GalNAc moieties of the invention introduces a stereocenter into the backbone between the phosphonate linkages as illustrated by the asterisk below.

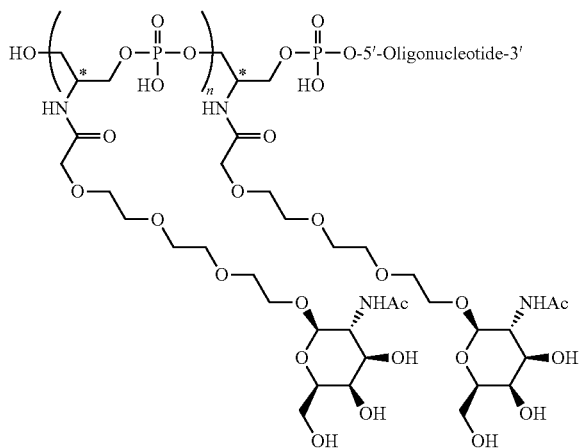

In the present example it was investigated whether the stereodefined versions of the compound would affect the potency and oligo content. The experiment was conducted in primary mouse hepatocytes.

The compounds in table 18 were generated using stereodefined DMT-mono-GalNAc phosphoramidites 7-D and 7-L (see example 8) using the process of example 3. The oligonucleotide used for the conjugation was 5'-$G_S{}^mC_Sa_St_Sg_Sg_St_Sa_St_ST_S{}^mC_SA$ (SEQ ID NO: 1). The incorporation was at the 5' end of the oligonucleotide with phosphodiester linkages between the oligonucleotide and first mono-GalNAc moiety as well as between the following stereodefined mono-GalNAc units. The compounds are stereodefined versions of compound J. The stereoconfiguration of each of the GalNAc units in the oligonucleotides refers to the use of either phosphoramidite 7-D (D) or 7-L (L) in the oligonucleotide synthesis. The stereoconfiguration D and L does not refer to any measured optical rotation of the oligonucleotides J-1-J-8 or compounds 5-D, 5-L, 6-D, 6-L. 7-D, or 7-L.

TABLE 18

Stereodefined versions of compound J

| Compound | Stereo configuration |
|---|---|
| J-1 | 5'-DDD |
| J-2 | 5'-DLD |
| J-3 | 5'-DDL |
| J-4 | 5'-DLL |
| J-5 | 5'-LDD |
| J-6 | 5'-LDL |
| J-7 | 5'-LLD |
| J-8 | 5'-LLL |

In addition to the stereodefined compounds the study included compound F (unconjugated oligonucleotide) and compound G (GalNAc2 conjugated oligonucleotide).

Primary mouse hepatocytes were isolated from C57BL/6J female mice. The mice were anesthesized and the liver was perfused at a flow rate of 7 ml per min through the vena cava using Hank's balanced salt solution containing 15 mM Hepes and 0.38 mM EGTA for 5 min followed by collagenase solution (Hank's balanced salt solution containing 0.17 mg/ml Collagenase type 2 (Worthington 4176), 0.03% BSA, 3.2 mM $CaCl_2$ and 1.6 g/l $NaHCO_3$) for 12 min. Following perfusion, the liver was removed and the liver capsule was opened, the liver suspension was filtered through 70 μm cell strainer using William E medium. The cell suspension was centrifuged for 3 min at 50×g. Viable hepatocytes were further enriched by gradient centrifugation with 45% Percoll (Sigma cat. No. P4937) for 10 min at 50×g. The pellet was washed and resuspended in 25 ml William E medium (Sigma cat. no. W1878 complemented with 1×Pen/Strep, 2 mM L-glutamine and 10% FBS (ATCC #30-2030)), and seeded at 25.000 cells per well in collagen coated 96 well plates. After 3 hours the medium was exchanged and the oligonucleotides were added using 3 fold dilutions from 9 to 000.4 μM. Two different incubation regimens were used, one where the cells were incubated 4 hours with oligonucleotide following a medium exchange and continued incubation to a total of 72 hours. In the second regimen the cells were incubated for 72 hours with the oligonucleotides.

Figure 3:
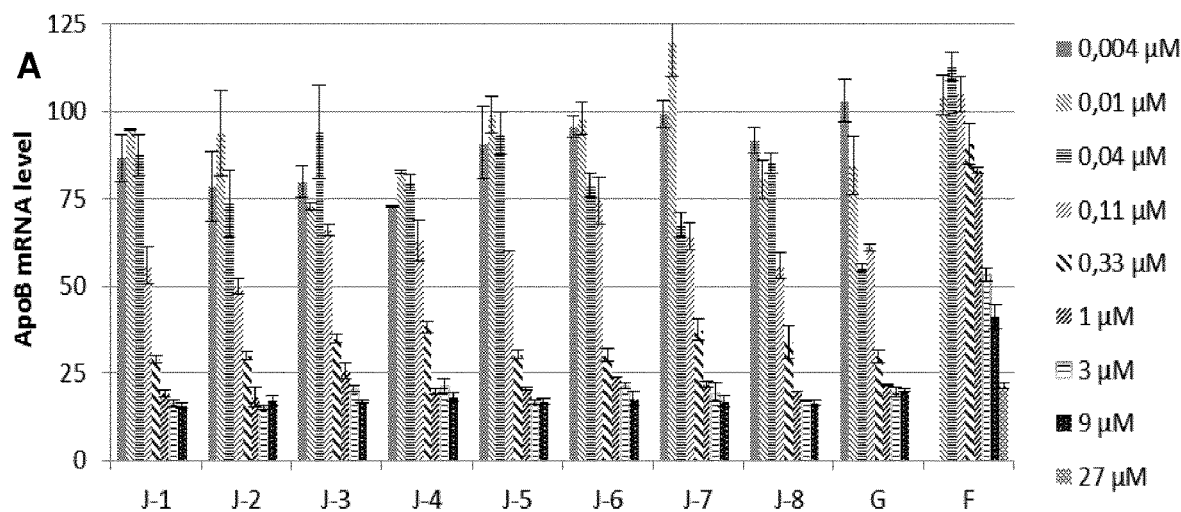
FIG. 3: Relative ApoB mRNA levels in primary mouse hepatocytes after A) 4 hours oligonucleotide compound treatment and total incubation of 72 hours or B) 72 hours oligonucleotide compound treatment. The J oligonucleotide compounds comprise stereodefined GalNAc moieties, G and F are GN2 conjugated and naked control compounds, respectively. Oligonucleotide compound concentrations were between 0.004 µM and 9 µM (3 fold dilutions) and for the naked compound and addition concentration of 27 µM was added.
Figure 3:
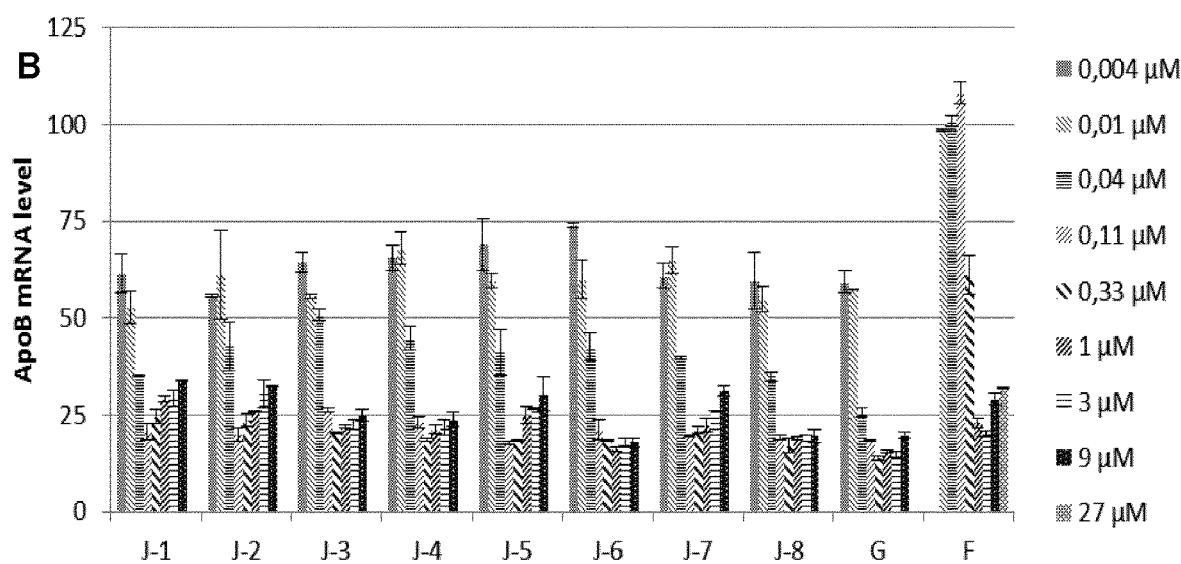

Total mRNA was extracted from the cells using the PureLink Pro 96 RNA Purification kit (Ambion), according to the manufacturer's instructions. For gene expressions analysis, qPCR was performed using qScript™ XLT One-Step RT-qPCR ToughMix®, Low ROX™ (Quanta Bioscience) in a duplex setup with the Taqman gene expression assay (mApoB, Mm01545150_m1 and mGAPDH #4352339E, Thermo Scientific) following the manufacturers protocol. The ApoB mRNA expression level relative to GAPDH is shown in FIG. 3 as percent of control (PBS treated cells) and the IC50 values are shown in table 19.

TABLE 19

| | IC50 values in μM, n = 2 | | | | | | | | | |
|---|---|---|---|---|---|---|---|---|---|---|
| Compound | J-1 | J-2 | J-3 | J-4 | J-4 | J-6 | J-7 | J-8 | G | F |
| 4 h pulse/72 h | 0.104 | 0.097 | 0.176 | 0.174 | 0.117 | 0.158 | 0.139 | 0.123 | 0.053 | 2.620 |
| 72 h | 0.004 | 0.004 | 0.006 | 0.017 | 0.008 | 0.012 | 0.006 | 0.006 | 0.006 | 0.331 |

Oligonucleotide content analysis was performed using ELISA (see for example Straarup et al 2010 Nucleic Acid Res Vol 38 pp 7100-7111), results are shown in table 20 and 21 below.

TABLE 20 oligonucleotide content (pmol/μg protein) in the cell culture after 4 h oligonucleotide treatment (pulse) and 72 hours total incubation, n = 2

| | Compound concentration | | | | | | | | | | | |
|---|---|---|---|---|---|---|---|---|---|---|---|---|
| | 9 μM | | 3 μM | | 1 μM | | 0.33 μM | | 0.11 μM | | 0.04 μM | |
| | Avg | std | Avg | std | Avg | std | Avg | std | Avg | std | Avg | std |
| J-1 | 2.3 | 0.2 | 1.5 | 0.1 | 1.5 | 0.0 | 0.9 | 0.1 | 0.3 | 0.0 | 0.1 | 0.0 |
| J-2 | 2.3 | 0.2 | 2.3 | 0.1 | 1.3 | 0.0 | 1.2 | 0.1 | 0.3 | 0.0 | 0.1 | 0.0 |
| J-3 | 2.3 | 0.0 | 1.6 | 0.1 | 1.6 | 0.1 | 1.1 | 0.1 | 0.3 | 0.1 | 0.1 | 0.0 |
| J-4 | 2.0 | 0.0 | 2.0 | 0.1 | 1.4 | 0.1 | 1.0 | 0.1 | 0.3 | 0.1 | 0.1 | 0.0 |
| J-5 | 2.4 | 0.1 | 2.3 | 0.0 | 1.8 | 0.1 | 1.4 | 0.0 | 0.4 | 0.1 | 0.1 | 0.0 |
| J-6 | 2.3 | 0.2 | 2.0 | 0.2 | 1.8 | 0.1 | 1.7 | 0.2 | 0.3 | 0.1 | 0.1 | 0.0 |
| J-7 | 3.2 | 0.0 | 2.3 | 0.1 | 2.1 | 0.2 | 1.9 | 0.2 | 0.4 | 0.1 | 0.1 | 0.0 |
| J-8 | 2.5 | 0.1 | 3.4 | 0.0 | 3.0 | 0.0 | 1.5 | 0.2 | 0.7 | 0.1 | 0.1 | 0.0 |

TABLE 20-continued oligonucleotide content (pmol/μg protein) in the cell culture after
4 h oligonucleotide treatment (pulse) and 72 hours total incubation, n = 2

| | \multicolumn{12}{c}{Compound concentration} | | | | | | | | | | | |
|---|---|---|---|---|---|---|---|---|---|---|---|---|
| | \multicolumn{2}{c}{9 μM} | \multicolumn{2}{c}{3 μM} | \multicolumn{2}{c}{1 μM} | \multicolumn{2}{c}{0.33 μM} | \multicolumn{2}{c}{0.11 μM} | \multicolumn{2}{c}{0.04 μM} |
| | Avg | std | Avg | std | Avg | std | Avg | std | Avg | std | Avg | std |
| G | 4.6 | 0.2 | 3.7 | 0.1 | 3.8 | 0.4 | 2.4 | 0.1 | 0.8 | 0.1 | 0.2 | 0.1 |
| F | 1.0 | 0.2 | 0.4 | 0.1 | 0.1 | 0.0 | n.d. | n.d | n.d. | n.d. | n.d | n.d. | n.d. = not detectable

Compound F (naked oligonucleotide) was also analyzed at a dose of 27 μM, at which the oligonucleotide content was 1.4+/−0.2 pmol/μg protein.

TABLE 21 oligonucleotide content (pmol/μg protein) in the cell culture
after 72 h oligonucleotide treatment, n = 2

| | \multicolumn{12}{c}{Compound concentration} | | | | | | | | | | | |
|---|---|---|---|---|---|---|---|---|---|---|---|---|
| | \multicolumn{2}{c}{9 μM} | \multicolumn{2}{c}{3 μM} | \multicolumn{2}{c}{1 μM} | \multicolumn{2}{c}{0.33 μM} | \multicolumn{2}{c}{0.11 μM} | \multicolumn{2}{c}{0.04 μM} |
| | Avg | std | Avg | std | Avg | std | Avg | std | Avg | std | Avg | std |
| J-1 | 10.6 | 0 | 9.8 | 0.1 | 12.8 | 0.4 | 8.9 | 0.3 | 3.3 | 0.1 | 2 | 0.1 |
| J-2 | 10.8 | 0 | 9.7 | 0.2 | 12.9 | 0.4 | 10.1 | 0.1 | 4.7 | 0.1 | 2 | 0.1 |
| J-3 | 13.9 | 0.1 | 14.4 | 0.5 | 11.3 | 0.1 | 9 | 0.2 | 5.4 | 0.1 | 1.5 | 0 |
| J-4 | 13.4 | 0 | 16 | 1 | 12.5 | 0.4 | 10 | 0.5 | 4.9 | 0.1 | 2.3 | 0.1 |
| J-5 | 15 | 0.6 | 16.5 | 0.6 | 12 | 0.4 | 6.8 | 0.2 | 6.7 | 0.1 | 1.9 | 0.1 |
| J-6 | 16.5 | 0.1 | 12.5 | 0.6 | 14.8 | 0.5 | 12.1 | 0.4 | 5.6 | 0.2 | 2.5 | 0.1 |
| J-7 | 16 | 0.6 | 17.1 | 0.8 | 14.3 | 0.6 | 11.3 | 0.4 | 4.8 | 0.1 | 2.2 | 0.1 |
| J-8 | 18.4 | 1 | 10.2 | 0.1 | 14.1 | 0.2 | 9.4 | 0.2 | 6.7 | 0.1 | 1.5 | 0 |
| G | 20.6 | 0.5 | 20.7 | 0.1 | 19.3 | 0.1 | 17.4 | 0 | 6.5 | 0.1 | 4.3 | 0.2 |
| F | 34.1 | 0.8 | 14.5 | 0.3 | 7.9 | 0.1 | 1.5 | 0 | 0.5 | 0 | n.d. | n.d. | n.d. = not detectable

Compound F (naked oligonucleotide) was also analyzed at a dose of 27 μM, at which the oligonucleotide content was 34.2+/−0.7 pmol/μg protein.

Conclusion:

The stereodefined GalNAc conjugates behave very similarly both in terms of target knock down and oligonucleotide content. When compared to compound G (prior art GalNAc construct—GalNAc2) the specific activity of the stereodefined GalNAc compounds seem a bit higher in that an equivalent knock down of ApoB is achieved with less oligonucleotide content in the cell. When comparing the two different incubation regimens it can be observed that a very efficient target knock down can be achieved after only 4 hours incubation with oligonucleotide, whereas for the naked oligonucleotide the uptake is slower and therefore more than 4 hours is needed to get sufficient oligonucleotide into the cell to achieve target knock down. With the 72 hour incubation with oligonucleotide the GalNAc conjugates achieve a higher knockdown of ApoB at doses below 0.33 μM compared to when the 4 h oligonucleotide incubation was applied.

The invention claimed is:

1. A nucleic acid molecule conjugate having the general formula (IV), including any salt thereof, wherein compound (IV) is represented by:

$$5'\text{-}R^7O\text{---}(Y^1)_p\text{---}NA\text{-}(Y^2)_q\text{---}OR^8\text{-}3' \quad (IV)$$

wherein NA is a nucleic acid molecule consisting of 7 to 50 nucleotides;

p and q are integers from 0 to 6, provided that p+q is at least 1, $R^7$ is H or a triphenylmethyl-based hydroxyl protecting group, $R^8$ is selected from H or a 3'-hydroxyl capping group, $Y^1$ is in each case independently represented by a compound of the general formula (V)

$Y^2$ is in each case independently represented by a compound of the general formula (VI)

wherein for each $Y^1$ and $Y^2$ independently $R^1$ is H or $C_{1-6}$ alkyl;

K' is represented by the general formula (II')

wherein L is a linker selected from the group consisting of $-(CH_2)_m-C(O)-$, wherein m=2-12;

$-(CH_2-CH_2-O)_n-CH_2-C(O)-$, wherein n=1-5;

$-(CH_2)_{m1}-CO-NH-(CH_2)_{m2}-NH-C(O)-$, wherein m1 and m2 each independently is 1-5;

$-(CH_2)_{m3}-CO-NH-(CH_2)_{m4}-C(O)-$, wherein m3 and m4 each independently is 1-5;

$-(CH_2)_{m6}-NH-C(O)-$, wherein m6 is 2-12, wherein in each case $C(O)-$ is attached to $NR^1$, and $Z^1$ and $Z^2$ are in each case independently selected from O and S, provided that at least one $Z^1$ is S.

2. The nucleic acid molecule conjugate of claim 1, wherein (i) p is 1 and q is 0, (ii) p is 2 and q is 0, (iii) p is 3 and q is 0, (iv) p is 4 and q is 0, (v) p is 0 and q is 1, (vi) p is 0 and q is 2, (vii) p is 0 and q is 3, or (viii) p is 0 and q is 4.

3. The nucleic acid molecule conjugate of claim 1, wherein the molecule is represented by formula (VII-XY) or formula (VIII-XY)

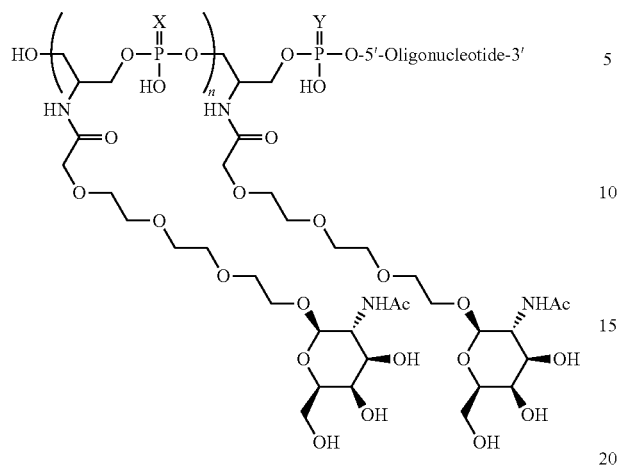

(VII-XY)

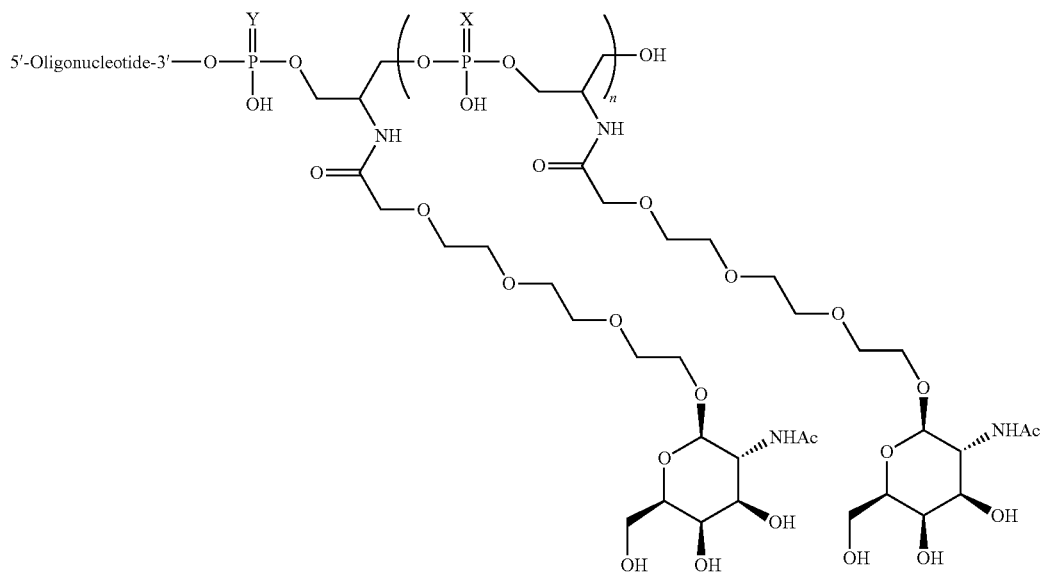

(VIII-XY)

where n is an integer from 0 to 3, and Y and X are independently selected from S and O, provided that at least one X is S.

4. The nucleic acid molecule conjugate of claim 3, wherein all X are S.

5. The nucleic acid molecule conjugate of claim 1, wherein the nucleic acid molecule comprises at least one modified nucleoside.

6. The nucleic acid molecule conjugate of claim 1, wherein the nucleic acid molecule comprises at least one modified internucleoside linkage.

7. The nucleic acid molecule conjugate of claim 1, wherein the nucleic acid molecule is capable of recruiting RNase H.

8. A pharmaceutical composition comprising the nucleic acid molecule conjugate of claim 1 and a pharmaceutically acceptable diluent, solvent, carrier, salt and/or adjuvant.

9. The nucleic acid molecule conjugate of claim 1 for use in medicine.

10. The nucleic acid molecule conjugate of claim 1, where L is selected from the group consisting of: —(CH$_2$)$_4$—C(O)—, —(CH$_2$)$_5$—C(O)—, —(CH$_2$)$_{11}$—C(O)—, —(CH$_2$)$_6$—NH—C(O)—, —(CH$_2$)$_{12}$—NH—C(O)—, —(CH$_2$)$_5$—CO—NH—(CH$_2$)$_5$—C(O)—, —(CH$_2$)$_4$—CO—NH—(CH$_2$)$_3$—NH—C(O)—, —(CH$_2$)$_4$—CO—NH—(CH$_2$)$_4$—NH—C(O)—, —(CH$_2$)$_5$—CO—NH—(CH$_2$)$_3$—NH—C(O)—, —(CH$_2$)$_5$—CO—NH—(CH$_2$)$_4$—NH—C(O)—, —(CH$_2$)$_6$—NH—CO—CH$_2$—NH—C(O)—, and —(CH$_2$CH$_2$O)$_2$—(CH$_2$)$_2$—NH—C(O)—.

11. The nucleic acid molecule conjugate of claim 1, wherein all $Z^1$ are S.

* * * * *